(12) United States Patent
Toth et al.

(10) Patent No.: US 11,185,361 B2
(45) Date of Patent: Nov. 30, 2021

(54) CONTROLLED AND PRECISE TREATMENT OF CARDIAC TISSUES

(71) Applicants: Landy Toth, Doylestown, PA (US); Robert S. Schwartz, Inver Grove Heights, MN (US)

(72) Inventors: Landy Toth, Doylestown, PA (US); Robert S. Schwartz, Inver Grove Heights, MN (US)

( * ) Notice: Subject to any disclaimer, the term of this patent is extended or adjusted under 35 U.S.C. 154(b) by 502 days.

(21) Appl. No.: 15/767,762

(22) PCT Filed: Oct. 10, 2016

(86) PCT No.: PCT/US2016/056256
§ 371 (c)(1),
(2) Date: Apr. 12, 2018

(87) PCT Pub. No.: WO2017/066121
PCT Pub. Date: Apr. 20, 2017

(65) Prior Publication Data
US 2019/0274746 A1  Sep. 12, 2019

Related U.S. Application Data

(60) Provisional application No. 62/239,974, filed on Oct. 12, 2015.

(51) Int. Cl.
*A61B 18/04* (2006.01)
*A61B 18/02* (2006.01)
(Continued)

(52) U.S. Cl.
CPC ............ *A61B 18/04* (2013.01); *A61B 5/4035* (2013.01); *A61B 18/02* (2013.01); *A61F 2/02* (2013.01);
(Continued)

(58) Field of Classification Search
CPC .. A61B 2018/0022; A61B 2018/00232; A61B 2018/00642; A61B 2018/1425;
(Continued)

(56) References Cited

U.S. PATENT DOCUMENTS

2005/0255039 A1  11/2005  Desai
2009/0163995 A1  6/2009  Shanley et al.
(Continued)

FOREIGN PATENT DOCUMENTS

EP       16856002    8/2019
WO       9503036     2/1995
(Continued)

*Primary Examiner* — Nathan R Price
*Assistant Examiner* — Melissa A Snyder
(74) *Attorney, Agent, or Firm* — Ryan, Mason & Lewis, LLP

(57) ABSTRACT

Compositions, systems, devices, and methods for performing precise chemical treatment of tissues are disclosed. Systems, devices, and methods for administering a chemical agent to one or more a precise regions within a tissue mass are disclosed. Compositions, systems, devices, and methods for treating targeted regions within a tissue mass are disclosed. Systems, devices, and methods for identifying, localizing, monitoring neural traffic in the vicinity of, quantifying neural traffic in the vicinity of, and mapping neural traffic near targeted regions within a tissue mass are disclosed.

23 Claims, 20 Drawing Sheets

(51) Int. Cl.
  A61K 9/06     (2006.01)
  A61K 31/045   (2006.01)
  A61K 47/38    (2006.01)
  A61K 49/00    (2006.01)
  A61L 27/20    (2006.01)
  A61B 5/00     (2006.01)
  A61L 27/54    (2006.01)
  A61F 2/02     (2006.01)
  A61L 27/50    (2006.01)
  A61B 17/00    (2006.01)
  A61B 18/00    (2006.01)
  A61B 18/14    (2006.01)
  A61N 7/02     (2006.01)
  A61B 5/287    (2021.01)

(52) U.S. Cl.
  CPC ............ *A61K 9/06* (2013.01); *A61K 31/045* (2013.01); *A61K 47/38* (2013.01); *A61K 49/0043* (2013.01); *A61L 27/20* (2013.01); *A61L 27/50* (2013.01); *A61L 27/54* (2013.01); *A61B 5/287* (2021.01); *A61B 5/4839* (2013.01); *A61B 5/7282* (2013.01); *A61B 18/1492* (2013.01); *A61B 2017/00566* (2013.01); *A61B 2018/0022* (2013.01); *A61B 2018/00041* (2013.01); *A61B 2018/00214* (2013.01); *A61B 2018/00267* (2013.01); *A61B 2018/00351* (2013.01); *A61B 2018/00577* (2013.01); *A61B 2018/00714* (2013.01); *A61B 2018/00839* (2013.01); *A61B 2018/0212* (2013.01); *A61B 2018/0293* (2013.01); *A61B 2018/046* (2013.01); *A61B 2018/143* (2013.01); *A61L 2300/256* (2013.01); *A61L 2300/40* (2013.01); *A61L 2300/414* (2013.01); *A61L 2300/416* (2013.01); *A61L 2300/432* (2013.01); *A61L 2300/436* (2013.01); *A61L 2400/06* (2013.01); *A61N 7/02* (2013.01)

(58) Field of Classification Search
  CPC ... A61B 18/1477; A61B 5/486; A61B 5/4839; A61M 25/0067; A61M 25/04; A61M 25/0032; A61M 2025/105; A61M 2039/0089; A61M 1/125; A61M 1/1072; A61M 2006/206
  See application file for complete search history.

(56) References Cited

U.S. PATENT DOCUMENTS

| 2011/0077628 | A1* | 3/2011 | Hoey | A61B 18/04 606/27 |
| 2011/0160648 | A1* | 6/2011 | Hoey | A61M 25/1002 604/26 |
| 2012/0109278 | A1 | 5/2012 | Sih | |
| 2012/0310140 | A1 | 12/2012 | Kramer et al. | |
| 2015/0011843 | A1 | 1/2015 | Toth et al. | |
| 2015/0119674 | A1* | 4/2015 | Fischell | A61B 5/24 600/381 |
| 2015/0342688 | A1* | 12/2015 | Wood | A61B 34/71 600/424 |
| 2016/0317621 | A1 | 11/2016 | Bright | |

FOREIGN PATENT DOCUMENTS

| WO | 2006007473 | | 1/2006 |
| WO | 2016014750 | A1 | 1/2016 |
| WO | PCT/US2016/056256 | | 3/2017 |

* cited by examiner

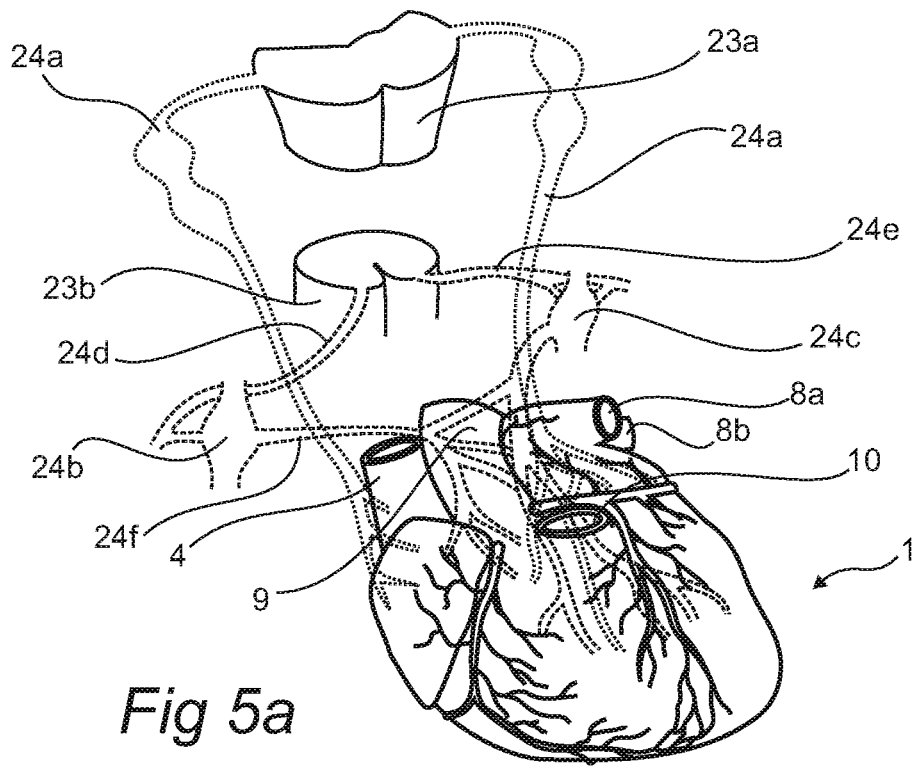
*Fig 5a*
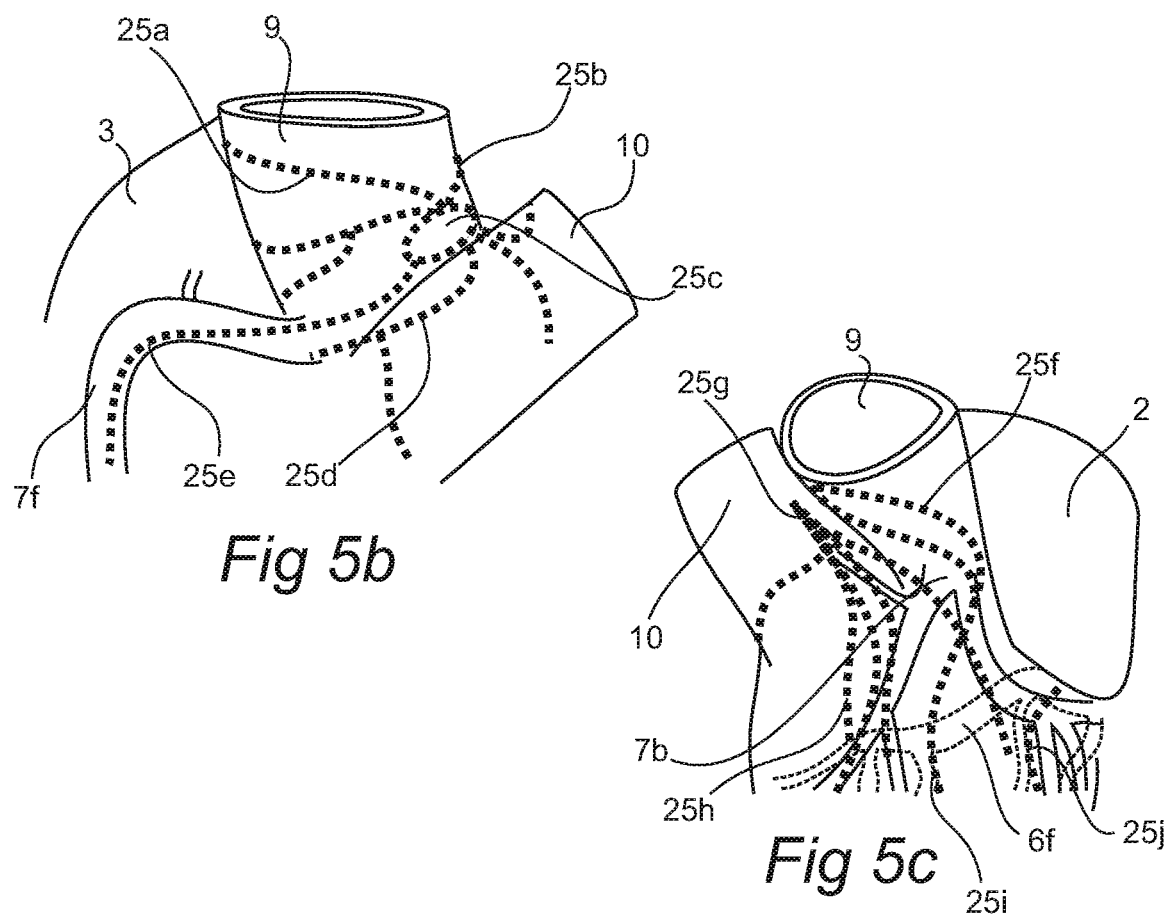
*Fig 5b*
*Fig 5c*

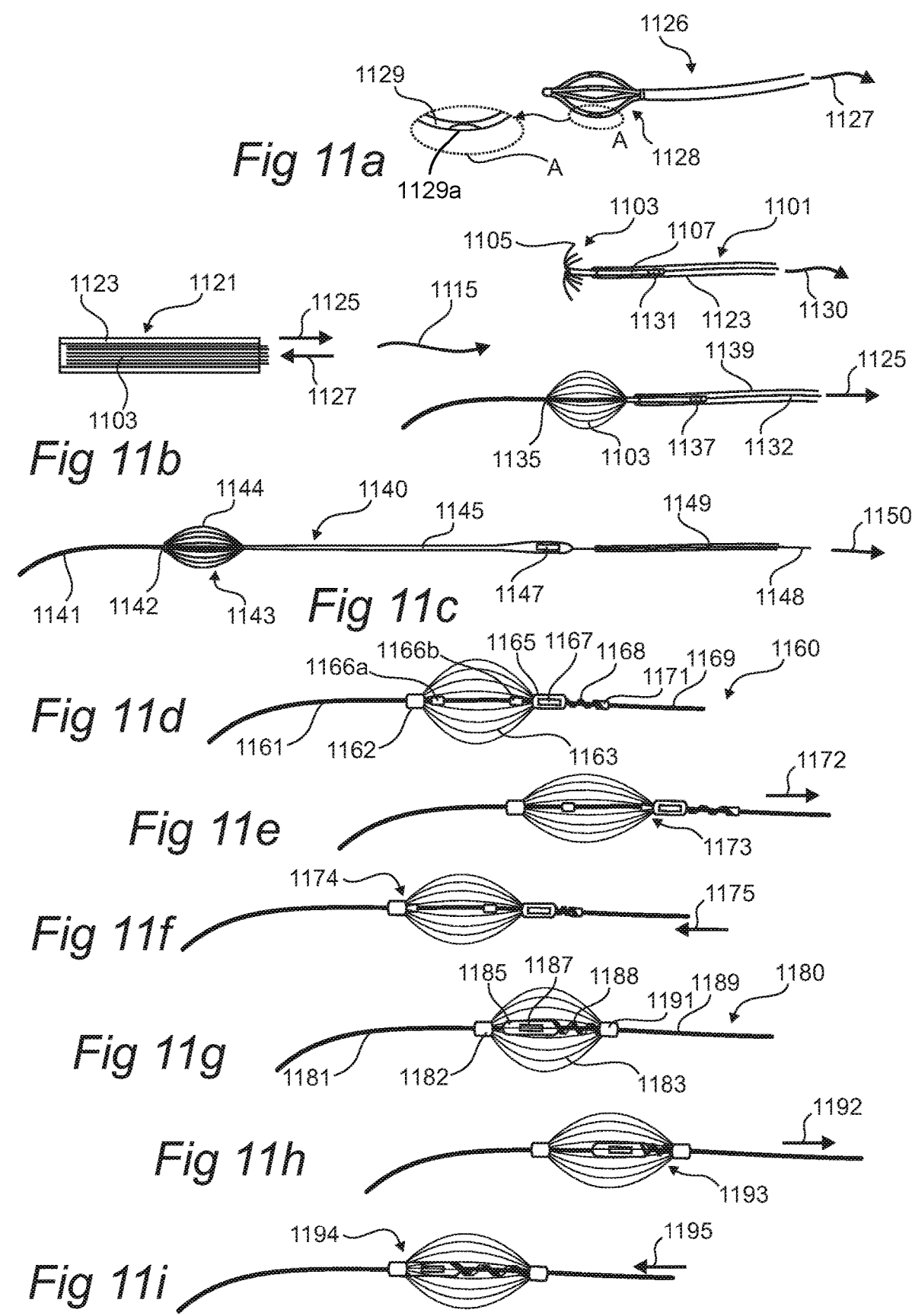

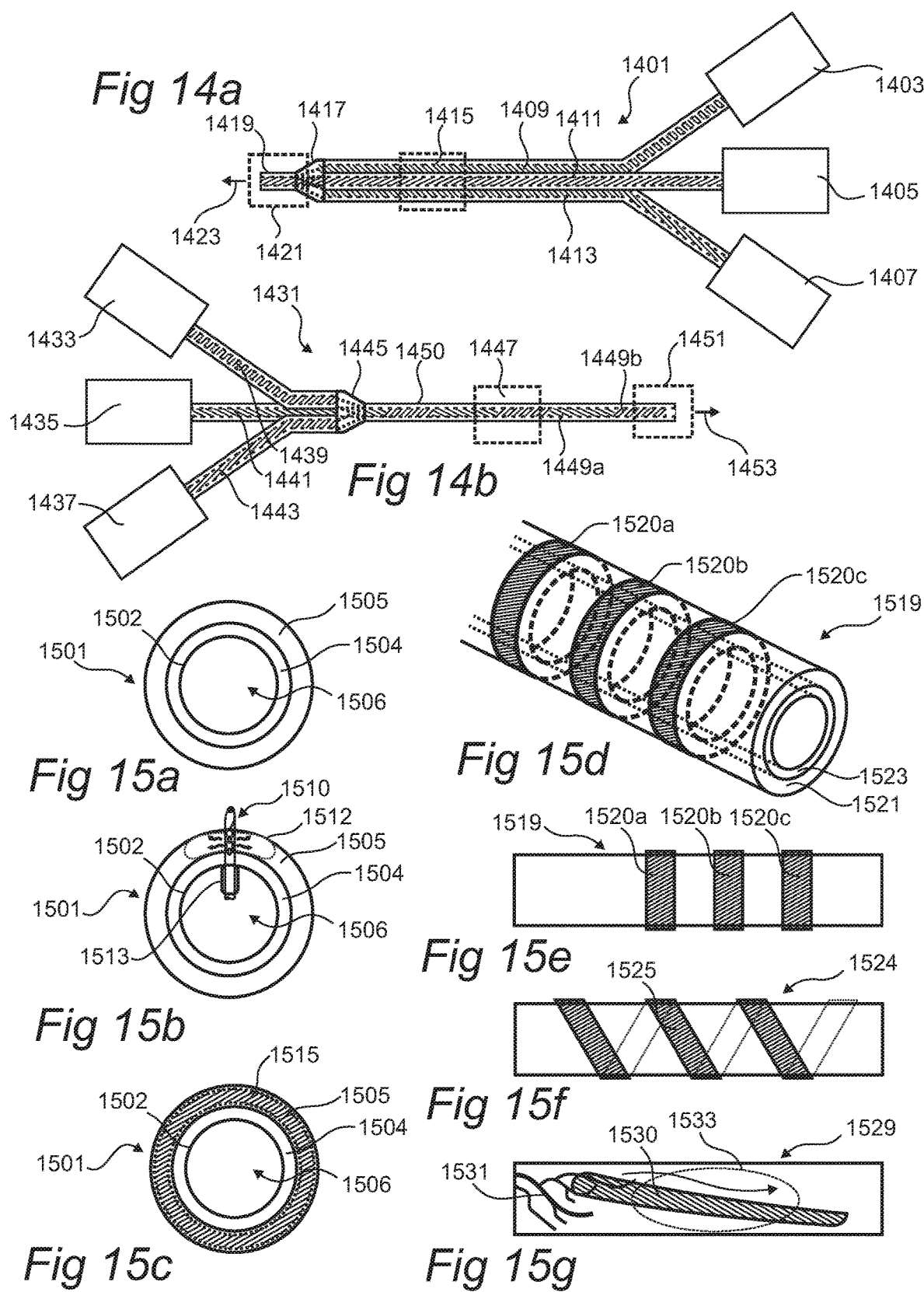

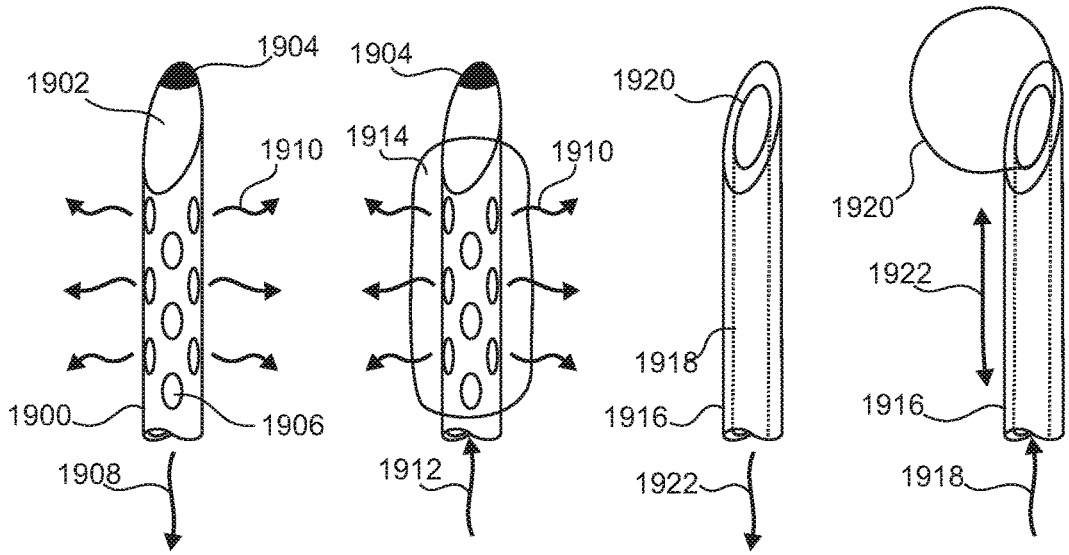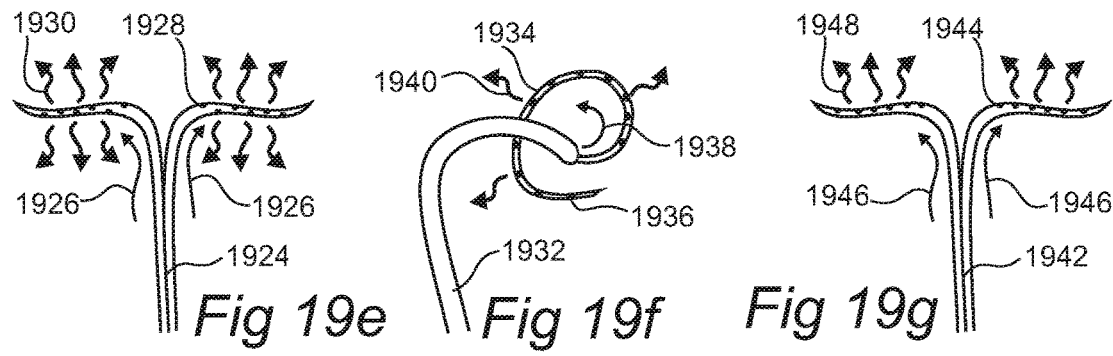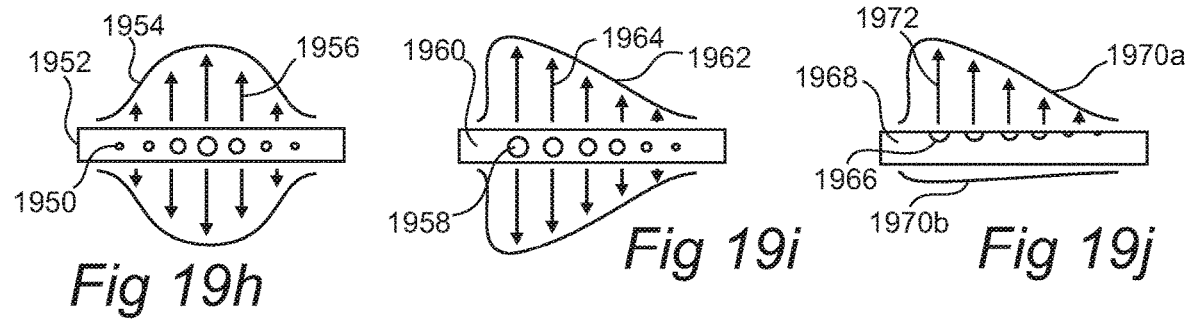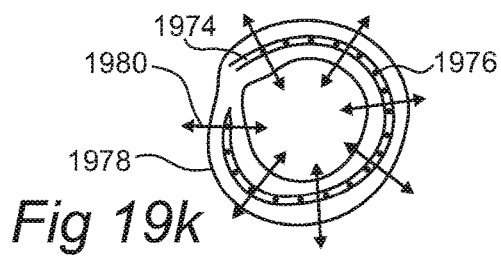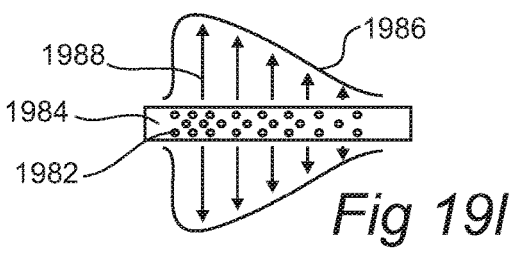

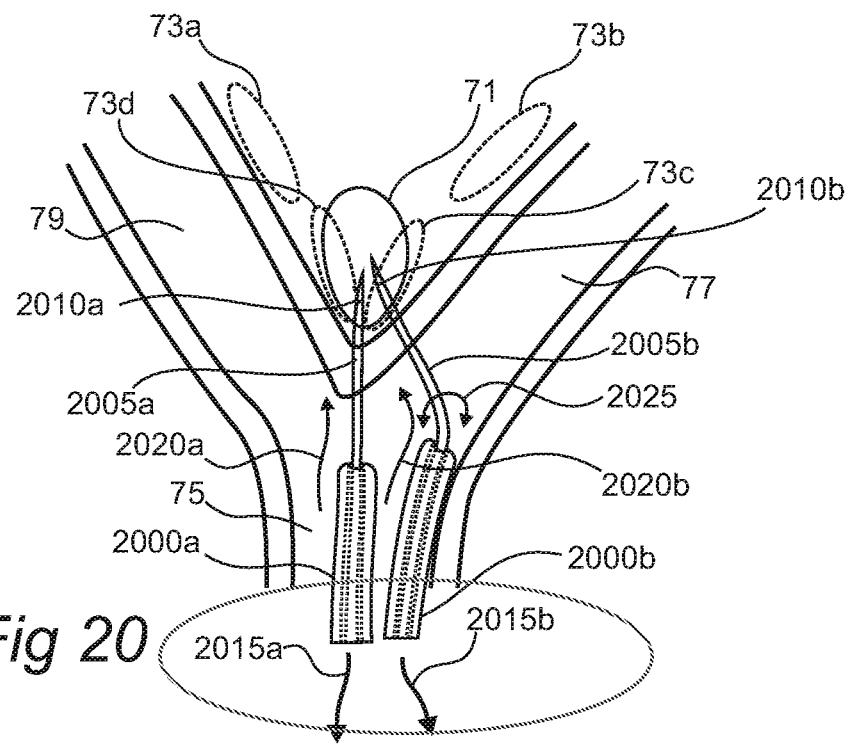
Fig 20
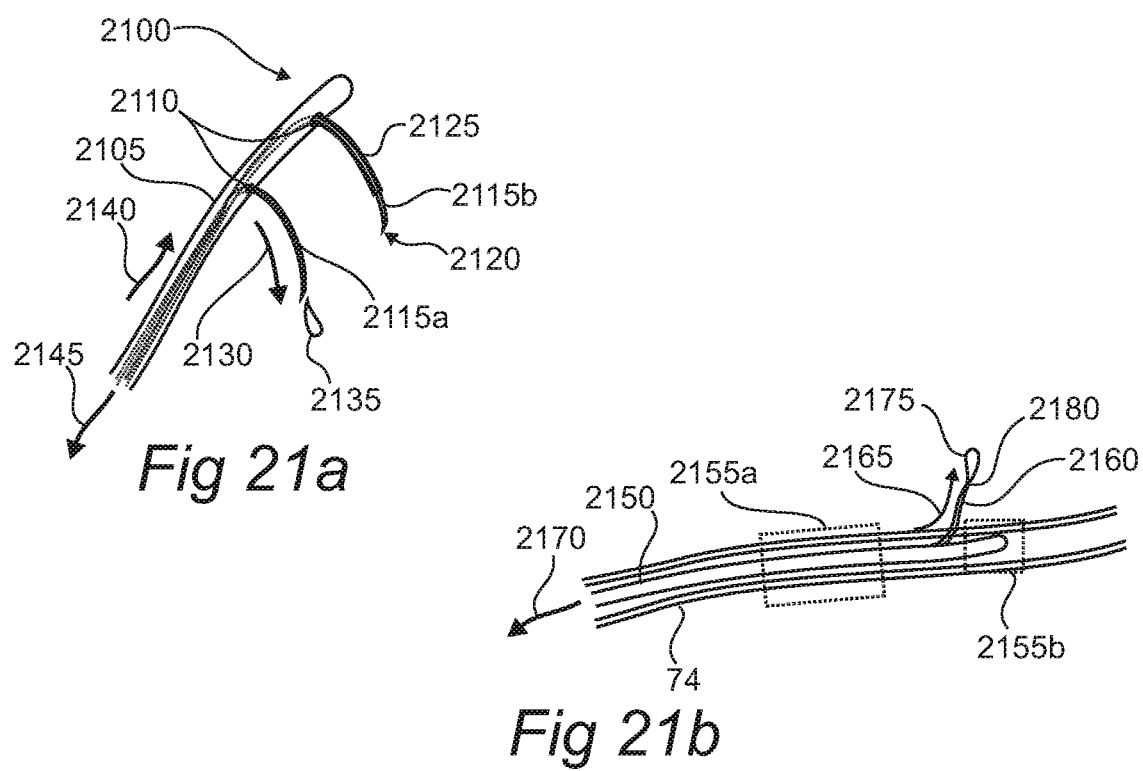
Fig 21a
Fig 21b

CONTROLLED AND PRECISE TREATMENT OF CARDIAC TISSUES

CROSS-REFERENCE TO RELATED APPLICATION

The present application is a national stage of International Application PCT/US2016/056256, which claims the benefit of and priority to U.S. Provisional Application Ser. No. 62/239,974, filed on Oct. 12, 2015 and entitled "Controlled and Precise Treatment of Cardiac Tissues," by Landy Toth et al., the entire contents of which are incorporated by reference herein for all purposes.

BACKGROUND

Technical Field

The present disclosure relates to the field of interventional modification of neurological or cardiac function of tissues. The present disclosure relates to interventional monitoring, detection, mapping, and diagnostic/therapeutic feedback of autonomic and cardiac electrophysiologic signals and function. The present disclosure relates to compositions, systems, devices, and methods for performing neuromodulation, denervation, and/or ablation of tissues.

Background

There are several disease states wherein ablation, neuromodulation, or functional change in a tissue is desired. Such disease states include pain management, arrhythmia treatments, neuroendocrine disorders, autoimmune disorders, lower urinary tract symptoms (LUTS), central nervous system disorders, and cancer.

Relating to cardiac diseases, the autonomic nervous system plays a major role in regulating and maintaining normal cardiac activity. However, it frequently also plays a major role in pathologic disease states.

A majority of cardiac disease is treated by sympathetic beta-receptor blockade. This includes ischemia (acute and chronic), angina (ischemic chest pain), arrhythmias (supraventricular or ventricular), heart failure including both systolic and diastolic dysfunction, coronary artery spasm and its pain.

Cardiac parameters as well govern blood pressure and hypertension which is an effect of the interaction between peripheral vascular resistance/impedance, myocardial contractility, cardiac stroke volume, and ventricular ejection time.

Beta receptor blockade by pharmacologic agents include specific, non-specific, and ISA agents, which by virtue of their systemic dosing affect all cells and cardiac structures (cardiac muscle, conduction tissues and tracts, pacemaker cells, cardiac stroma) indiscriminately and simultaneously.

The indiscriminate and global effects of systemic beta blockade leads to clinical problems whereby therapy of one function causes dysfunction of another. For example, beta blockade for heart failure (ventricular muscle cells) leads to severe bradyarrhythmias.

Systemic beta blockade as well affects all cells and organs of the body, often leading to unwanted and intolerable side effects (e.g., depression, impotence, lassitude, fatigue, etc.).

There is a need to treat such disease states with fewer complications.

SUMMARY

One illustrative, non-limiting objective of this disclosure is to provide methods for interventional treatment of cardiac muscle and coronary vessels. Another illustrative, non-limiting objective of this disclosure is to provide a tool for monitoring, evaluating the function of, mapping, and/or modulating electrophysiological activity in the vicinity of a lumen within a body. Yet another illustrative, non-limiting objective is to provide systems and methods for evaluating the extent of a neuromodulation procedure such as a neuromodulating ablation and/or stimulation. Another objective is to provide systems and methods for modifying lymphatic structures and the function or integrity thereof in a body.

According to a first aspect, there is provided an ablative composition for treatment of a site within a body of a subject including an ablative agent in accordance with the present disclosure for performing the treatment, and an excipient in accordance with the present disclosure for limiting migration of the composition and/or the ablative agent within the body after delivery to the site.

In aspects, the composition may include one or more components each in accordance with the present disclosure to facilitate the treatment, the delivery, the storage, the retention, and/or the stability of the composition.

In aspects, the ablative agent may include a neurotoxin, a cytotoxin, ethyl alcohol, phenol, botulinum toxin, a hypertonic solution, anon-aqueous solvent, combinations, derivatives, analogs, salts, thereof, or the like and the excipient may include a monosaccharide, a disaccharide, a polysaccharide, a starch, a glucan, a cellulose, combinations, copolymers, derivatives, modifications, analogs, tautomeric forms, stereoisomers, polymorphs, solvates, salts, nano/micro particulates, and metabolites thereof, or the like.

In aspects, the ablative agent may represent more than 85%, more than 90%, more than 95%, or more than 98% of the composition by mass. In aspects, a solvent may be added to the composition to adjust the low shear viscosity thereof.

In aspects, the excipient may have an average molecular weight of greater than 1,000, greater than 10,000, greater than 100,000, or greater than 1,000,000, or the like.

In aspects, the composition may be formulated so as to form a viscous thixotropic gel with a thixotropic index of greater than 1.25, greater than 1.5, greater than 2, or greater than 4, at 37° C. (degrees Celsius) and/or a Bingham plastic with a yield strength of greater than 5 Pa (Pascals), greater than 20 Pa, or greater than 100 Pa, at 37° C. In aspects, the composition may form a substantially low viscosity fluid at a temperature between 45 and 80° C., 45 and 60° C., 45 and 55° C., or the like, the low viscosity being less than 4,000 cps (centipoises), less than 2000 cps, less than 500 cps, etc.

In aspects, the excipient may include hydroxypropyl cellulose (HPC), hydroxypropyl starch (HPS), or a modified form thereof, a blend of HPC, HPS, or a modified form thereof, with one or more of ethylcellulose (EC), methylcellulose (MC), hydroxyethylcellulose (HEC), hydroxypropylmethylcellulose (HPMC), carboxymethylcellulose (CMC), cellulose gum, cellulose ether, a starch equivalent form, a modified form thereof, or the like.

In aspects, the composition may be formulated so as to form a gel-like skin when submerged into an aqueous medium and is substantially soluble in a solution of the active agent.

In aspects, the ablative agent may act as a vehicle for the composition, the viscosity of the composition substantially increasing as the active agent migrates into a volume of tissues surrounding the site, after delivery to the site.

In aspects, the composition may be formulated so as to limit migration of the active agent from an injection site to a distance of less than approximately 3 mm (millimeters), less than approximately 2 mm, less than approximately 1 mm, or the like from a margin of a bolus formed by the composition after delivery to the site within a timeframe comparable with the delivery of the composition to the site.

In aspects, the ablative composition may include a contrast agent selected from a fluorescent agent, a CT (computed tomography) contrast agent, an iodine based contrast agent, an MRI (magnetic resonance imaging) contrast agent, or a combination thereof.

In aspects, the ablative agent may include a chemotherapeutic agent, a cytotoxic agent, an antibody drug conjugate, an anti-neural growth factor, a mitotic inhibitor, a poison, a neurotoxin, a combination thereof, or the like.

According to aspects, there is provided a delivery system for delivering an ablative composition in accordance with the present disclosure to a treatment site within a volume of tissue, the delivery system including a delivery tool including a lumen, the lumen forming a fluid coupling between a distal end and a proximal end of the delivery tool, a reservoir for retaining the composition prior to delivery, the reservoir coupled with the proximal end of the delivery tool, an injector coupled to the reservoir, the injector configured to deliver a bolus of the composition into the delivery tool upon activation thereof, and a delivery tip coupled to the lumen, the delivery tip deploy-ably coupled to the delivery tool, shaped and dimensioned so as to penetrate into or bias against the volume of tissue upon deployment from the delivery tool, the delivery tip including one or more ports coupled to the lumen, the ports arranged upon the delivery tip so as to access the site.

In aspects, the delivery system may include a thermal regulating unit coupled to the lumen and/or the reservoir, the thermal regulating unit configured to maintain the composition at a predetermined temperature prior to and/or during delivery. The thermal regulating unit may include a heating band, braid, laser machined hypotube, or the like coupled with the lumen, the heating band configured to maintain the composition at a temperature during delivery through the lumen.

In aspects, the ports may be arranged along the delivery tip with a spatially changing density and/or diameter such that the bolus may be shaped when delivered from the delivery tip.

In aspects, the delivery tip may include or may be a needle, the needle shaped so as to penetrate into the volume of tissue upon deployment, the ports arranged along the length of the needle. The ports may be arranged such that the bolus is formed substantially in the shape of a cylinder, a sphere, an ellipsoid, a torus, a tear drop, a cone, or the like when delivered to the site.

In aspects, the delivery system may include a balloon coupled with the delivery tip, the balloon coupled to a fluid source so as to be expand-ably deployed during a procedure so as to interface the delivery tip with the wall of a vessel or the volume of tissue. The balloon may include one or more energy delivery elements, and/or sensing elements to interface with the wall of the lumen and/or the volume of tissue.

In aspects, the delivery tool and/or the delivery tip may include one or more sensing elements, or electrodes each in accordance with the present disclosure to interface with the volume of tissue. In aspects, the system may be configured to direct energy through the energy delivery elements based upon the information collected by the sensing elements or electrodes. The sensing elements may be configured to monitor and/or determine the signals relating to regions of abnormal electrophysiological activity, determine the direction of nerve traffic along nerves in the volume of tissue, sympathetic neural activity in the volume of tissue, determine the type of nerves situated near the sensing element, determine the effectiveness of the energy and/or composition delivery, determine the response of nerve traffic to a stress test performed on the body or the organ, determine the positioning of the sensing elements in the body, determine the transition of the sensing elements between anatomical features in the body (e.g. between a muscle and an adventitia, through a membrane, into a wall of an artery, etc.), a combination thereof, or the like.

In aspects, the volume of tissues may be coupled to one or more regions of a vessel wall, an artery, a vein, an arteriole, an adventitia of a vessel wall, an organ, a muscle mass, a ganglion, a diseased tissue, a tumor, combinations thereof, or the like.

In aspects, the delivery tip may have a characteristic diameter of less than 1 mm, less than 0.75 mm, less than 0.5 mm, or less than 0.3 mm so as to access the volume of tissue within the body.

In aspects, the system may include a tissue suction element, a deployable cup-like element, or the like in accordance with the present disclosure, coupled to the delivery tip, the suction element configured to retain the site against the delivery tip there against upon activation before, during, and/or after the delivery. In aspects, the suction element may be arranged so as to draw the site onto the delivery tip upon activation.

In aspects, the delivery tip may be arranged within the suction element so as to deliver the bolus into the drawn in site of the tissue.

According to aspects, there is provided use of a composition in accordance with the present disclosure and/or a system in accordance with the present disclosure to reduce, and/or prevent communication of pain signals originating within a tumor microenvironment or associated organ from traveling along a nerve in the volume of tissue.

According to aspects, there is provided use of a composition in accordance with the present disclosure and/or a delivery system in accordance with the present disclosure to treat a cardiac disease, a cardiac arrhythmia, to isolate a tissue site in a cardiac muscle, to treat a diseased tissue site in an organ, or a combination thereof.

According to aspects, there is provided use of a composition in accordance with the present disclosure and/or a delivery system in accordance with the present disclosure to form an embolism in a region of an organ, a kidney, a portion of a kidney served by an accessory vessel, or a combination thereof.

According to aspects, there is provided a method for treating a region in a volume of tissue including delivering a composition in accordance with the present disclosure to a tissue site within the volume of tissue, and monitoring the effect of the composition on the electrophysiological state of the region, and/or monitoring the migration of the composition in the region after delivery to the site. The monitoring of the effect may be advantageous for correlating an electrophysiological state of the neural structures coupled to the tissues with the physiological process altered by one or more components of the composition (e.g., such as correlating neural traffic changes with renin release in one or more regions of a kidney, etc.).

In aspects, the method may include forming a pattern of the composition in the region. The pattern may be formed in the shape of a ring around the perimeter of the region, so as to isolate the region from the surrounding volume of tissue, formed through deposition of a plurality of boluses at points over a three dimensional path within the volume of tissue.

In aspects, the region may include a tumor and the pattern may be formed over the margin of the tumor.

According to aspects, there is provided a method to ablate and/or assess a region of an organ coupled to an arterial tree including identifying a branch of the arterial tree that substantially exclusively provides blood flow to the region, and delivering a bolus of a composition in accordance with the present disclosure into the branch.

In aspects, the step of identifying may be facilitated by performing one or more contrast angiograms in one or more branches of the arterial tree, correlating an approach with a 3D (three dimensional) tomographic image, a CT image, an MRI image, etc.

In aspects, the method may include monitoring the effect of the composition on the electrophysiological state of the branch (e.g., so as to determine the state of nerve kill, nerve block, the completion of the ablation procedure, the electrophysiological response to a stress test, etc.).

In aspects, the method may include monitoring migration of the composition into the organ and/or a vascular tree coupled thereto.

In aspects, the organ may be a kidney, and the arterial tree may be coupled to an accessory artery.

In aspects, the method may include performing a stress test on the region of the organ, the stress test including injecting a drug, or a stressing agent such as a vasodilator, a vasoconstrictor, a neuroblocker, a neurostimulant, a diuretic, insulin, glucose, beta-adrenergic receptor antagonist, angiotensin-11 converting enzyme inhibitor, calcium channel blocker, an HMG-CoA reductase inhibitor, digoxin, an anticoagulant, a diuretic, a beta blocker, an ACE inhibitor, a steroid, a combination thereof, or the like into the branch, and/or organ and monitoring a physiological response of the subject to the stress test. Such a test may be advantageous for assessing the function of the region, so as for diagnostic purposes, to select one or more regions to ablate, to compare the performance of regions, to assess the suitability of a subject for a therapeutic procedure, etc.

In aspects, the delivery of the bolus may be directed into a lumen of the branch, an adventitia surrounding the branch, into a wall surrounding the lumen, and/or into an organ coupled thereto.

In aspects, the step of delivery may be performed by a delivery system in accordance with the present disclosure. In aspects, the method may include positioning at least a portion of the delivery system into the arterial tree via a main artery serving the tree. In aspects, one or more portions of the delivery system may be embodied within a catheter and/or guidewire in accordance with the present disclosure.

In aspects, the catheter or guidewire may be equipped with a substance eluting element, configured to deliver the composition, a substance, a medicament, a denervating substance, a combination thereof, or the like into the target organ, into a perivascular site surrounding the wall of the lumen, into the adventitia of the lumen, into a microenvironment of the tumor, into the lumen, into the tissues surrounding the wall of the lumen, into a region within the wall of the lumen, a combination thereof, or the like.

In aspects, the method may include treating and/or ablating one or more nerves coupled to the region, while substantially limiting damage to the tissues surrounding the region or the nerves, substantially limiting damage to the organ coupled to the region, substantially limiting local inflammation, or the like.

In aspects, induced necrosis will typically cause the corresponding cells to exhibit rapid swelling, lose membrane integrity, shut down metabolism, and release their contents into the environment. Cells that undergo rapid necrosis in vitro do not often have sufficient time or energy to activate apoptotic machinery and thus will often not express apoptotic markers. Rather induced apoptosis typically causes the corresponding cells to exhibit cytological and molecular events such as a change in the refractive index of the cell, cytoplasmic shrinkage, nuclear condensation, and cleavage of DNA (deoxyribonucleic acid) into regularly sized fragments.

In aspects, the composition may be selected so as to induce apoptosis in one or more neural tissues (i.e., axon, dendrite, cell body, myelin sheath, synapse, etc.).

According to aspects, there is provided use of one or more systems, methods, and devices each in accordance with the present disclosure for interventionally altering one or more homeostatic or neuroendocrine processes within a body.

Some non-limiting examples of homeostatic processes include production/release of renin, insulin, cholesterol, bile salts, testosterone, progesterone, prion, serotonin, endorphins, dopamine, monoamine neurotransmitters, histamines, noradrenaline, glucose, and the like, adjustment of blood pressure, anti-inflammatory activity, estrogen, uterine hemorrhaging, hunger, bowel movement, nutritional uptake in the bowel, bone density, a rate of bone remodeling, formation of osteoblasts and the like.

In aspects, a system in accordance with the present disclosure may include a substance delivery aspect, configured for elution of a substance into the vicinity of the target.

BRIEF DESCRIPTION OF THE DRAWINGS

Several aspects of the disclosure can be better understood with reference to the following drawings. In the drawings, like reference numerals designate corresponding parts throughout the several views.

FIGS. 5a-c illustrate the autonomic innervation into the heart and the innervation around the major vessels coupled with a human heart.

FIGS. 11a-i illustrate aspects of sensing devices in accordance with the present disclosure.

FIGS. 14a-b illustrate aspects of delivery devices in accordance with the present disclosure.

FIGS. 15a-g illustrate aspects of treatments on coronary vessels in accordance with the present disclosure.

FIGS. 19a-l show aspects of delivery tips in accordance with the present disclosure.

FIG. 20 shows application of a composition, delivery system, and delivery tip each in accordance with the present disclosure to treatment of a carotid body.

FIGS. 21a-b show aspects of a delivery system in accordance with the present disclosure for treating tissues along a vessel.

DETAILED DESCRIPTION

Figure 1A:
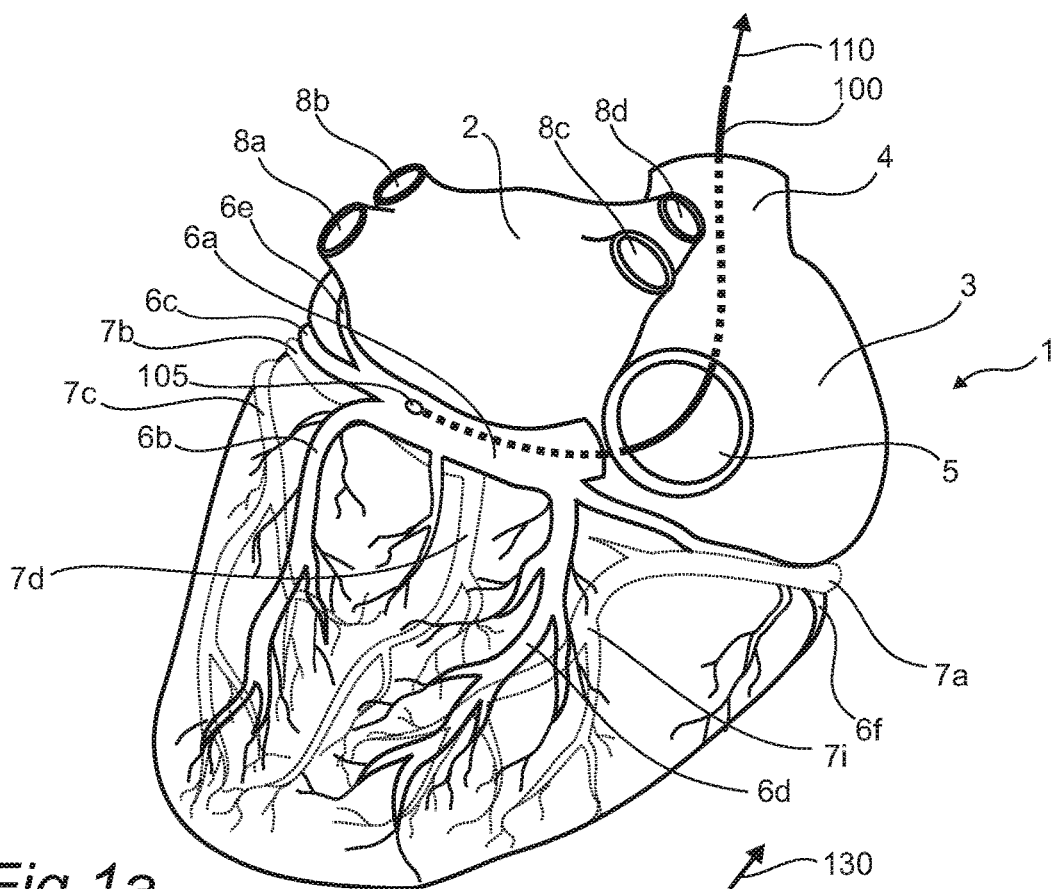
FIGS. 1a-b show catheter access routes into various coronary vessels of a human heart.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as an illustrative basis for the claims and as a representative basis for teaching one skilled in the art to variously employ the present disclosure in virtually any appropriately detailed structure. Like reference numerals may refer to similar or identical elements throughout the description of the figures.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Methods and techniques for cardiac tissue treatments, as well as cardiac denervation are described throughout this disclosure. In aspects, the anatomic relationships between the neural target sites and to coronary arteries and veins may be considered to access the targets with minimal collateral damage to the adjacent tissues. Autonomic nerve fibers and hence cardiac innervation anatomically co-locates with the coronary arteries and veins after leaving the cardiac ganglia. Such anatomic relationships are analogous to other organs such as the kidney whereby colocation of blood supply and neural traffic make for anatomic, evolutionary efficiency and simplicity (i.e., evolutionary simplification such that there is no need for separate bundles fulfilling different nourishment and regulatory function).

In aspects, specific local sites for targeting therapy are the coronary artery and coronary vein adventitia; the coronary arteries and veins lie on and within the heart muscle, and are very predictable in location and distribution.

In accordance with the present disclosure, cardiac and/or neural therapy, cardiac denervation, or the like can thus be selectively performed through the coronary arteries perfusing a specific cardiac region or the coronary veins receiving blood from a specific region. In aspects, a sensing element, sensing catheter, or the like in accordance with the present disclosure may sense cardiac autonomic neural activity at the inner-lumen of a coronary vessel, a cardiac chamber, etc. Some non-limiting examples of regions that may be targeted with a device and/or method in accordance with the present disclosure include, but are not limited to the atria (individual walls), the ventricles (e.g., ventricular septum, lateral, inferior, posterior, anterior walls), conduction tissue (e.g., SA node, AV node, His bundles, R/L bundles), combinations thereof, and the like.

In aspects, autonomic neural sensing may be achieved by antenna deployment (i.e., an array including a plurality of sensing elements and/or electrodes each in accordance with the present disclosure) at the luminal vessel surface. In aspects, a therapy, an ablation procedure, or the like may be performed as guided by luminal autonomic signals.

In aspects, cardiac denervation may also be performed on tissue that is abnormal, for example infarcted, partially infarcted, ischemic myocardium any of which can be detrimental as sources of arrhythmia or abnormal function. In aspects, denervation when performed procedurally in accordance with the present disclosure may be highly controlled and site-selective using a device or method in accordance with the present disclosure. In one non-limiting example, if the locus of an arrhythmia is identified, the myocardium responsible for arrhythmogenesis could be selectively denervated with a device or method in accordance with the present disclosure.

In aspects, to perform a localized, highly selective therapy to such cardiac tissues, a key component of the denervation may involve highly localized sensing in accordance with the present disclosure, a technique that will guide the ablation technology as the procedure is underway, and also determine when the desired ablation has reached its goal. This disclosure thus identifies sensing and ablation within the same device.

In aspects, denervation of tissues in accordance with the present disclosure need not be binary, either none or complete. It can be applied selectively and proportionally (e.g., incomplete, complete, neuro-selective, controlled so as to alter neural traffic or local nerve density by a given percentage, less than 95%, less than 75%, less than 50%, less than 25%, etc.). In one non-limiting example, incomplete denervation may find use, for example, in partially ablating neural drive to a cardiac pacemaker cell group, preserving some degree of natural regulation but decreasing its impact. Another non-limiting example may be found in dysautonomias such as the POTS syndrome (Postural Orthostatic Tachycardia), where a natural reflex is over-reactive. Yet another non-limiting example may be found in coronary vessel spasm, wherein local neural sprouting and aberrant traffic may lead to spasm instead of dilation. In such applications, a controlled, proportional denervation may be advantageous in terms of improved efficacy.

Aspects of the present disclosure may be directed to cardiac ganglion ablation and corresponding methods for sensory-aided catheter-based pre-ablation sensing. In aspects, sensing ganglion tissue prior to ablation would have substantial clinical benefit. A high fidelity sensing element in accordance with the present disclosure may be suitable for measuring ganglion tissue neural activity, generally in the frequency range of 0.01 Hz-5 kHz or 100 Hz-2 kHz, including 200 Hz-1 kHz, and over the voltage range of 1 μV-1 mV, including 1 μV-50 μV. The sensing element may be configured so as to measure neural activity as well as smooth muscle activity, movement artifacts, and the like, such that the frequency range may be extended to cover 0.01 Hz-5 kHz, including 1 Hz-3 kHz, or the like. For example, a neural ablation probe (regardless of ablation modality) brought into, within, or near a cardiac ganglion of the heart would permit partial or complete ganglion destruction. The sensed autonomic neural information may be utilized to localize the ganglion, diagnose the ganglion neural traffic, quantify the ganglion neural traffic, monitor the traffic during a procedure, after a procedure, etc. Furthermore, the neural sensing may be suitable for mapping changes in spatial neural traffic patterns around a ganglion before, during, and/or after an associated ablation procedure. Such mapping may be advantageous to locate other neural targets, monitoring neural traffic patterns in the vicinity of a ganglion, to/from a ganglion, changes in neural patterns during a local temporary neural block, traffic before, during, or after a plurality of local spatially distributed neural blocks, or the like.

Generally speaking, current methods cannot sense neural or muscular activity thus ablation is carried out in a "blind" manner. The sensing electrode or array of electrodes is used to sense neurologic or muscular activity consistent with the structure that is intended to be ablated.

In aspects, the sensing technology can be separated or integrated with the ablation technology. The present disclosure utilizes feedback of a neurologic or myogenic sensing technology in conjunction with the ablation technology to permit direct knowledge of what the procedure is being planned in an appropriate patient, whether the procedure is being performed correctly, and when the procedure can be terminated.

In another non-limiting example, a system, device, catheter, method, or a combination thereof each in accordance with the present disclosure may be configured to perform autonomic ablation via the coronary vessels (e.g. arteries or veins), via procedure based, highly focal cardiac denervation. Such procedures may be suitable for treating various disorders. Some non-limiting examples of such disorders include suppressing coronary plaque formation, limiting or eliminating chest pain, preventing or limiting coronary vessel spasm, myocardial infarction and unstable angina pectoris, cardiac arrhythmias, congestive heart failure, augmenting heart function, altering blood pressure, combinations thereof, and the like.

In aspects, local coronary treatment may be used for suppressing coronary artery plaque formation. Multiple histopathologic studies clearly show local inflammation as a major cause of coronary artery plaque formation. This includes vulnerable plaque (responsible for plaque size/growth, myocardial infarction, unstable angina, etc.), stable plaque, and restenosis following interventional procedures. The source of chronic plaque information is poorly understood. Focal inflammation in malignant tumors is enhanced or initiated by active sympathetic autonomic drive. Sympathetic denervation of the heart by reducing local inflammation may limit coronary artery plaque formation and hence coronary artery disease with a multitude of its consequences. Such an approach may be advantageous for treating subjects with fewer comorbidities, side effects, fewer cardiac events, and longer patient survival than existing therapeutic approaches.

In aspects, local coronary treatment may be used for limiting or eliminating chest pain. Angina pectoris can be debilitating and uncontrollable in a substantial number of heart patients. Refractory angina represents a significant clinical problem that is debilitating and has massive impact for a negative lifestyle and extremely poor quality of life since even minor activities are frequently accompanied by severe pain. In addition, angina at rest often prevents such patients from carrying on any semblance of a normal life. Afferent neural activity conveying pain response travels in part through the coronary arteries. Treatment, and/or ablation of these nerves may result in substantial, marked, or complete elimination of anginal pain in a subject.

In aspects, local coronary treatment may be used for preventing coronary vessel spasm. Spasm of the coronary arteries is a potentially lethal condition whereby neurologically mediated traction of the coronary arteries cause marked reduction or even cessation of blood flow through the coronary artery. Lack of blood flow in a corner artery can cause severe pain, ischemia, scar formation in muscle, lethal arrhythmias, and death. Affected individuals with recurrent coronary artery spasm are at very high risk for substantial morbidity and mortality. Even in normal individuals coronary artery spasm can play a role in the genesis of heart attack, ischemia, myocardial infarction and associated symptoms including chest pain arrhythmias and death. Autonomic innervation of the coronary vessels contributes to contraction, dilation, and spasm. Such spasm is particularly associated with neuroplastic changes in autonomic innervation (i.e., local neural sprouting associated with damage caused by trauma, local ischemia, plaque formation, receptor density changes, and the like). Local monitoring of associated neural traffic and/or treatment of coronary autonomic nerves may thus have substantial impact on vessel spasm, associated pain, and heart attack thus positively affecting patient life span, quality of life, and the like.

In aspects, local coronary nerve treatment may be used for treating myocardial infarction and unstable angina pectoris. Myocardial infarction and its mechanisms related to coronary artery initiation are poorly understood. It is well known that it is a capricious illness that may occur at any time whereby plaque on the coronary artery interacts with blood flow to cause the clot that obstructs the vessel. It is quite conceivable that coronary artery spasm induces or contributes to the formation of the clot by making an already plaque-narrowed lumen become completely or near-completely obstructed. Moreover, enhanced sympathetic tone locally and systemically is a source of enhanced platelet aggregation, a potent source of increased coronary artery thrombosis. Local identification of aberrant neural traffic and/or treatment of autonomic coronary nerves may thus have substantial impact on myocardial infarction thus positively affecting patient life span, quality of life, and the like.

In aspects, one or more devices, systems, and methods each in accordance with the present disclosure may be used to treat one or more cardiac arrhythmias. Sympathetic beta blockade is a well-known pharmacologic strategy to reduce or eliminate cardiac arrhythmias. These include atrial arrhythmias (e.g., atrial fibrillation, supraventricular ectopy, supraventricular tachycardia) and ventricular arrhythmias (e.g. ventricular ectopy, ventricular tachycardia, ventricular fibrillation). Local, feedback sensing based ablations for treating such arrhythmias may allow for treatment without the need for long term systemic medication, reduction in side effects, patient comorbidities, and the like.

In aspects, one or more devices, systems, and methods each in accordance with the present disclosure may be used to treat congestive heart failure. A mainstay therapy of congestive heart failure involves beta receptor blockade. Chronic sympathetic stimulation of the ventricular myocardium and heart failure results in a weakening of the heart muscle that very clearly reduces patient survival. Cardiac denervation in accordance with the present disclosure may provide a procedurally-based elimination of sympathetic stimulation which will more exactly, permanently and efficiently eliminate or markedly reduce sympathetic activity in the heart for patients with impending or advanced heart failure.

In aspects, one or more devices, systems, and methods each in accordance with the present disclosure may be used to treat hypertension or alter blood pressure waveforms. Hypertension is a detrimental mismatch between peripheral vascular resistance, cardiac stroke volume, and ejection period. Each of these are controlled in large part by a balance of sympathetic and parasympathetic neural drive. Early evidence also suggests feedback/crosstalk between the renal nerves and cardiac sympathetic nerves. Selective denervation of cardiac structures may thus substantively impact blood pressure. Such an approach may be combined with other therapies to provide a complimentary approach to reducing blood pressure, to cost effectively reduce blood pressure, or the like.

Thus, selectively sensing and ablating the cardiac autonomic nervous system at strategically located sites (such as may be identified with a high fidelity sensory feedback system, device, catheter, sensing tip, sensing element or the like in accordance with the present disclosure), may have a substantial impact toward disease limitation or elimination. A cornerstone of cardiovascular disease treatment utilizes autonomic neural inhibition in the form of sympathetic and parasympathetic neural inhibition. The sympathetic nervous system is inhibited by pharmacologic beta blockade, cornerstones of modern cardiology therapy. Beta blockade is a strategy used to treat chest pain (angina pectoris), congestive heart failure, coronary artery disease, hypertension, and multiple other sympathetic mediated ailments.

In aspects, ablation of nerves within the artery wall may require special design for certain vascular beds. Many vascular beds respond to luminal injury with prolific neointimal thickening, a process causing restenosis after the injury of percutaneous intervention and stenting. The reason for neointimal formation is vascular injury to the media and denotes physiologically by injury to the internal elastic lamina. Implications are significant in that attempted neural ablation in the coronary artery bed, for example, can easily injure the artery and result in unwanted effects of vascular compromise and stenosis. This will occur with heating, RF energy, cryotherapy, microwave, laser etc., and certain ultrasonic ablation that heat the medial wall.

The present disclosure describes systems, devices, delivery systems, tissue access systems, methods, and compositions in order to treat such coronary tissues with limited risk of vascular injury. Generally speaking, a valid ablation technology should kill only cells in the adventitia.

One non-limiting method disclosed herein includes delivery of a potent, viscous ablation fluid such as an ethanol gel in accordance with the present disclosure to the target tissue site. Technology described herein that selectively deposits (e.g. delivery tips and associated methods in accordance with the present disclosure), and confidently deposits (e.g. via dense spatial and high fidelity neural sensing by one or more sensing components in accordance with the present disclosure), the gel circumferentially within the adventitial region of autonomic neural axons is a method to accomplish these means.

In aspects, such a delivery system may include a needle with a fixed stop distally, equal to roughly the medial thickness so as to permit needle deployment whereby the distal needle penetrates into or near the adventitia. In such an arrangement, the proximal needle is without holes, so the ablation fluid deposition pattern is primarily into the adventitial region with minimal fluid delivered into the medial layer of the vessel wall.

In aspects, the pressure injection profile of holes along the needle tip may also be tailored to avoid medial gel deposition. In this approach, custom holes arranged distally in the needle in accordance with the present disclosure will allow for selective deposition of gel in a circumferential rather than a radial direction into the wall of the target vessel. In such an arrangement, the magnitude of applied pressure may govern the circumferential gel pattern. A multiplicity of needles (typically 3-6) may be constructed to create a completely circumferential ablation zone, depending on arterial diameter and pressure of injection.

In aspects, the patterns and size of holes in the needles may be arranged such that when 3 or more needles, when inserted into the media of the vessel wall, deliver a pressurized gel there through which may form a substantially complete circumferential linear lesion, and substantially ablate neural activity from crossing this linear lesion. In aspects, a pattern of highly precise and spatially distributed ablations may be formed in the wall of the vessel so as to treat a proportion of it, such as less than 90%, less than 75%, less than 50%, less than 25%, or the like. In aspects, a variable pressure magnitude applied during delivery of boluses of the therapeutic substance may be used to change the size/width of the resulting linear lesion, with more pressure, in general, resulting in a wider lesion.

Alternatively, longitudinal lesions along the length of the vessel may be generated by making exit holes in the needle along the vessel axis rather than perpendicular to it.

This method of making lesions is applicable to making lesions in various arterial supplies to organs within the body.

Some non-limiting examples of ablation applications include but are not limited to, heart based applications as listed herein, pancreas based applications (augmentation of pancreatic blood supply (Celiac/SMA) for treating cancer, to limit or eliminate pain, to favorably impact metastasis and/or tumor progression, etc.), lung based applications (e.g., treatment of pulmonary arteries, denervated to favorably impact vascular resistance (lessen), reduce pulmonary hypertension, etc.), treatment of bronchi (so as to reduce bronchospasm, asthmatic attacks/symptoms, etc.), treatment of the kidneys (to reduce hypertension, change glomerular filtration rates, etc.), treatment of the bladder (to treat neurogenic bladder, LUTs disorders, reduce overactive bladder spasm, pain, urge incontinence symptoms, etc.), treatment of the carotid body (to reduce blood pressure, limit activity, reduce sensitivity to blood pressure changes, etc.), treatment of the adrenal glands (to reduce corticosteroid sensitivity/secretion and the like), treatment of adipose tissue (to alter metabolic function, inflammatory function, etc.), treatment of the spleen (to influence inflammatory function, etc.), treatment of the extremities (to reduce ulcer formation, treat reflex sympathetic dystrophy, etc.), treatment of the stomach (reduce gastrin/stomach acid secretion, etc.), treatment of the gastrointestinal system, the duodenum, the colon, the small intestine (e.g. so as to affect receptor density distribution, to disrupt gastrointestinal signaling, to treat inflammatory bowel disease, autoimmune bowel disease, autoimmune ulceration, irritable colon, etc.), combinations thereof, and the like.

In aspects, a system, device, surgical tool, interventional tool, catheter, or guidewire in accordance with the present disclosure may be used to access, monitor, and/or to treat one or more neurological pathways, ganglia, and/or sensory receptors within a body: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. Such receptors may be associated with one or more organs and/or physiologic processes within the body (i.e., a regulatory process, feedback systems, pain receptors, etc.).

In aspects, a sensing device in accordance with the present disclosure may be used to interface with one or more neural structures, perform a diagnostic procedure, guide a therapeutic procedure, map neural tissues, map tissue responsiveness, identify tissues with abnormal neural activity, or the like. Several descriptions of such devices are included herein, as well as in the applications incorporated by reference below. An example of such a device is an interventional tool (e.g., a microsurgical tool) configured for monitoring electrophysiological activity within the vicinity of a lumen, the microsurgical tool including one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962, published as WO 2014/160832 and titled "Neurological Traffic and Receptor Evaluation and Modification: Systems and Methods," the disclosure of which is incorporated herein by reference. Other such devices for which sensing function is suitable for performing one or more of the procedures herein include, but are not limited to those devices described in: PCT application serial no. PCT/US2013/023157, published as WO 2013/112844 and titled "Controlled Sympathectomy and Micro-Ablation Systems and Methods"; PCT application serial no. PCT/US2013/042847, published as WO 2013/181137 and titled "Endoscopic Sympathectomy Systems and Methods"; PCT application serial no. PCT/US2013/045605, published as WO 2013/188640 and titled "Devices, Systems, and Methods for Diagnosis and Treatment of Overactive Bladder"; PCT application serial no. PCT/US2013/067726, published as WO 2014/070999 and titled "Systems, Methods, and Devices for Monitoring and Treatment of Tissues Within and/or Through a Lumen Wall"; and PCT application serial no. PCT/US2013/073844, published as WO 2014/089553 and titled "Systems and Methods for Regulating Organ and/or Tumor Growth Rates, Function, and/or Development," the disclosures of which are incorporated herein by reference.

In aspects, one or more systems in accordance with the present disclosure may be coupled with one or more imaging modalities including computer assisted imaging computed tomography (CT), magnetic resonance imaging (MRI), positron emission tomography (PET), magnetoencephalography (MEG), functional MRI, stereotactic surgery, or the like before, during, and/or after a surgical procedure. Such imaging modalities may be used to provide visualization of a target tissue, of advancement of one or more aspects of the system towards the target tissue, confirmation of placement of one or more aspects with respect to the target tissue or surgical site, etc. Use of such imaging modalities may be performed prior to/after surgery, and/or intraoperatively.

In aspects, one or more probes in accordance with the present disclosure may include a fiber optic coupled to a light source and/or a laser (e.g., fiber optic guided radiation to a target tissue), a cryotherapy unit, a heat circulation unit (i.e., a unit for heated wire thermal therapy), an ultrasonic generator, or the like for treatment and/or monitoring of target tissue. For purposes of discussion, the majority of non-limiting examples discussed herein are directed to electrical interfacing with tissues and chemical delivery aspects of such therapies.

A system and/or tool in accordance with the present disclosure may include an elongate member with a proximal end and a distal tip, at least a portion of which may be configured for placement within the lumen of a body, the elongate member including one or more conduits each conduit providing a channel for connecting a more distal aspect of the elongate member to a more proximal aspect thereof. The elongate member may include and/or interface with one or more probes, at least a region of one or more of the probes slide-ably coupled to the elongate member so as to advance from the elongate member in a direction towards an associated lumen wall (e.g., radially, circumferentially, axially, combinations thereof, or the like). At least one probe may include an electrode, a needle, a fluid delivery aspect, combinations thereof, or the like.

In aspects, one or more probes may be arranged so as to pass through one or more of the conduits. In aspects, one or more of the probes and/or conduits may be coupled to a fluid source at a proximal end thereof and configured to provide a fluid there through to a distal tip thereof, to one or more tissue sites in the vicinity of the distal tip, etc.

In aspects, a probe and/or elongate member may include one or more microelectrodes for monitoring local electrophysiological activity, one or more of the microelectrodes may have an area of less than 1 $mm^2$, less than 0.1 $mm^2$, less than 100 $\mu m^2$, or the like. In aspects, a probe and/or elongate member may include a stimulating and/or ablating electrode for stimulating and/or treating a local tissue site in the vicinity thereof. In aspects, one or more of the stimulating and/or ablating electrodes may have an area of more than 0.25 $mm^2$, more than 1 $mm^2$, more than 2.5 $mm^2$, more than 50 $mm^2$, or the like.

In aspects, one or more of the probes may include a plurality of electrodes (e.g., microelectrodes, stimulating electrodes, and/or ablating electrodes) each in accordance with the present disclosure. Such sensory elements and electrodes may be coupled with one or more delivery elements, the delivery elements configured to deliver one or more substances to a tissue site of interest within a subject.

According to aspects, there is provided a composition for ablation of a tissue site in a body, the composition including a tissue ablating agent for actively treating the tissues in the vicinity of the tissue site, and an excipient for regulating migration and/or a release rate of the tissue ablating agent away from the tissue site upon injection into the tissue site.

In aspects, the tissue ablating agent may include an alcohol, ethanol, isopropyl alcohol, benzyl alcohol, phenol, ethanolamine, athanolamine oleate, sodium tetradecyl sulfate, a chemotherapeutic agent, combinations thereof, or the like. In aspects, the tissue ablating agent may perform at least a portion of the function of a vehicle for delivery of the composition to the tissue site.

In aspects, the excipient may include silica, polyvinylpyrrolidone (PVP), glycerin, polyethylene glycol, chitosan, acelated monoglycerides, glycerides, oil, wax, collagen, bovine collagen, cellulose gum, Contigen®, Duraphere®, polyacrylic acid, polyvinyl alcohol, polyvinyl alcohol copolymer, calcium hydroxylapatite (CaHA), calcium acetate, polymaleic acid, polyvinyl methyl ether, silicone, polydimethylsiloxane, glycosaminoglycans, mucopolysaccharides, hyaluronic acid, hyaluronan, autologous fat, autologous ear chondrocytes, polytetrafluoroethylene, cellulose, combinations, copolymers, derivatives, analogs, tautomeric forms, stereoisomers, polymorphs, solvates, salts, nano/micro particulates, and metabolites thereof, or the like.

In aspects, the excipient may include a polysaccharide, a starch, a glucan, a glucose polymer, cellulose, combinations, copolymers, derivatives, analogs, tautomeric forms, stereoisomers, polymorphs, solvates, salts, nano/micro particulates, oxidated forms, esters, ethers, and metabolites thereof, or the like. Some non-limiting examples of cellulose derivatives include ethylcellulose (EC), hydroxypropylcellulose (HPC), methylcellulose (MC), hydroxyethylcellulose (HEC), hydroxypropylmethylcellulose (HPMC), carboxymethylcellulose (CMC), oxycellulose, cellulose ester, cellulose gum, cellulose ether, combinations thereof, or the like. In aspects, the cellulose may be selected from a group of cellulose derivatives that are at least partially soluble in the ablating agent or a vehicle (e.g., a solvent, dimethyl sulfoxide, ethyl acetate, an alcohol, a processing agent, etc.) included in the composition, and in an aqueous medium (e.g., water, saline, normal saline, hypertonic saline, etc.). In aspects, the cellulose may have a substantially higher solubility in the ablating agent or the vehicle than in the aqueous medium. In aspects, the cellulose derivative may have an ethoxyl content of between 45-52%, between 47-49.5%, etc.

In aspects, the cellulose derivative may have an average molecular weight of greater than 1,000, greater than 10,000, greater than 100,000, greater than 1,000,000, or the like.

Some non-limiting examples of starch derivatives include dextrin, acid-modified starch, alkaline-modified starch, bleached starch, oxidized starch, enzyme-treated starch, maltodextrin, cyclodextrin, monostarch phosphate, distarch phosphate, acetylated starch, hydroxypropylated starch, hydroxyethyl starch, starch sodium octenyl succinate (OSA) starch, starch aluminium octenyl succinate, cationic starch, carboxymethylated starch, phosphated distarch phosphate, acetylated distarch phosphate, acetylated distarch adipate, hydroxypropyl distarch phosphate, acetylated oxidized starch, monostarch phosphate, distarch phosphate, phosphated distarch phosphate, acetylated distarch phosphate, starch acetate, acetylated distarch adipate, hydroxypropyl starch, hydroxypropyl distarch phosphate, hydroxypropyl distarch glycerol, combinations, copolymers, derivatives, analogs, tautomeric forms, stereoisomers, polymorphs, solvates, salts, nano/micro particulates, and metabolites thereof, or the like In aspects, the composition may include one or more surfactants (e.g., an anionic, nonionic, cationic, amphoteric surfactant, sodium lauryl sulfate, ammonium lauryl sulfate, lauryl alcohol ether sulfate, trimethylcoco ammonium chloride, etc.), the surfactant configured so as to maintain the integrity of the composition over a wider temperature range, pH range, to compatibilize one or more components of the composition with a vehicle, to improve wetting of a tissue interface upon delivery thereto, or the like, than achievable without the surfactant.

In aspects, a thermal stabilizing agent may be added to the composition, such as an organic liquid, a surfactant, an alcohol, an aqueous glycol, or the like. Such thermal stabilizing agent may be advantageous to increase the temperature range over which the composition may remain stable at the tissue site, during storage, during delivery to a tissue site, etc. In aspects, the composition may be thermally stable over a temperature range of 10-60° C., 10-50° C., 10-45° C., or the like. In aspects, the composition may be formulated (e.g., with a cellulose derivative based excipient in accordance with the present disclosure) such that the viscosity of the composition at body temperature (approximately 37° C.), is substantially higher than the viscosity in the range of 45-50° C. In aspects, the composition is formulated such that the ratio between viscosities between 37° C.:50° C. is greater than 10:1, greater than 100:1, greater than 1000:1, etc.

In aspects, the composition may include a cellulose derivative, the thermal viscosity profile of the cellulose derivative and the vehicle including a high viscosity over a first pH range, and a low viscosity over a second pH range. In aspects, the first pH range may be near 7, near 7.4, etc. In aspects, the second pH range may be greater than 7.5, greater than 7.7, less than 5, less than 4, or the like.

In aspects, the composition may include an inorganic salt, a dissolved material, sucrose, glucose, combinations thereof, or the like.

In aspects, the composition may include a defoaming agent, a lauryl alcohol, octyl alcohol, etc.

In aspects, the composition may include a cellular therapeutic agent, a myoblast, a fibroblast, a stem cell (a muscle-derived, or adipose-derived stem cell, etc.), a multipotent hematopoietic stem cell (autogeneic, allogeneic, etc.), or the like. Such cellular therapeutic agents may be delivered to a tissue site in a body within a composition in accordance with the present disclosure so as to precisely retain the cells during the implantation stage into the subject, to prevent widespread migration of the cells into the blood stream, etc.

In aspects, the composition may include a polymerizing agent, a polymer, gelatin, pectin, xanthan gum, polysaccharide, polyvinyl alcohol, poly(lactic-co-glycolic acid) (PLGA), ethylene vinyl alcohol (EvOH), or the like. Such polymer forming agents may be advantageous to form a gelatinous, or solid-like bolus of the composition after delivery to a tissue site in the body.

In aspects, the composition may include a tissue adhesive agent, a tissue glue, a fibrin, a fibrin sealant, fibrinogen, thrombin, a cyanoacrylate, n-butyle-2-cyanoacrylate, combinations, derivatives, analogs, tautomeric forms, stereoisomers, polymorphs, solvates, salts, and metabolites thereof, or the like.

In aspects, the composition may include a contrast agent, a CT contrast agent, an iodine or barium based agent, an ionic iodinated medium, diatrizoate, metrizoate, ioxaglate, a nonionic iodinated medium, iopamidol, iohexol, ioxilan, iopromide, iodixanol, a barium sulfate, an MR contrast agent, a gadinolium based medium, omniscan, prohance, gadavist, optimark, magnevist, dotarem, primovist, an iron oxide based medium, a protein based agent, amino acid bound gadolinium media, combinations thereof, or the like.

In aspects, the composition may be formulated as a highly viscous fluid, or a gel, the composition including an excipient in accordance with the present disclosure, and the tissue ablating agent forming at least a portion of a vehicle for the fluid or gel medium.

In aspects, a composition in accordance with the present disclosure may be configured as a gel, the tissue ablating agent present in a proportion by weight of greater than 90%, greater than 95%, greater than 98%, greater than 99%, etc. of the overall composition. In aspects, the composition may include greater than 97% ethyl alcohol, greater than 98% ethyl alcohol, greater than 99% ethyl alcohol, etc.

In aspects, the tissue ablating agent may be present in a proportion by weight of from 5-80%, 30-70%, from 40-50%, etc. Such a configuration may be advantageous to augment local neural traffic or to defunctionalize the local nerves without inducing cell death.

In aspects, the composition may be formulated as a non-Newtonian fluid, a shear thinning medium (e.g., a thixotropic medium, a pseudoplastic medium, a Bingham plastic, etc.). In aspects, the composition may be formulated as a Bingham plastic, with a yield strength of greater than 5 Pa, greater than 20 Pa, greater than 100 Pa, or the like. The pseudo gel-like composition may behave as a plastic fluid having a high yield strength, high viscosity, and/or low gel strength. The yield strength may be independent of shear stress, shear rate, total work input, and time under stress. Plastic fluids were defined by Bingham as fluids having a yield strength that must be exceeded in order to initiate flow. In aspects, the yield stress of the pseudo gel-like composition may be configured such that the gel can flow freely through a delivery catheter under a high shear condition, but the flow substantially stops when the force applied is less than the force required to overcome the yield strength, forming essentially a pseudo solid-like gel.

In aspects, the composition may be formulated so as to behave as a thixotropic medium, thus flowing more freely once flowing has been initiated, the medium having a thixotropic index (as measured with a viscometer at two different shear rates, such as a first rate and 10× the first rate, with the same spindle and measurement temperature), of greater than 1.25, greater than 1.5, greater than 2, greater than 4, etc. Such a configuration may be advantageous for delivery of the composition to a tissue site through a delivery system in accordance with the present disclosure, while retaining a high degree of stability after delivery to the tissue site.

In aspects, the composition may be configured so as to exhibit a phase change property dictated by the local environment (e.g., local temperature, pH, humidity, salinity, etc.). The composition may include one or more environmentally, anion-responsive, organogels, or the like. The composition may include a first gelator molecule, configured to form a stable first fluid or gel state in a first solution (e.g., such as in the tissue ablating agent), over a first range of temperatures, pH, salinity, etc., the gelator molecule configured to form a second fluid or gel state over a second range of temperatures, pH, salinity, in the presence of a second solution (e.g., a surrounding aqueous medium, in the presence of an analyte, an enzyme, a protein, or the like). In aspects, the transition between the first fluid or gel state to the second fluid or gel state may be advantageous in expelling the tissue ablating agent, retaining the tissue ablating agent, releasing a medicament into the tissue site, increasing the viscosity or yield stress of the medium upon placement at a tissue site, etc. In aspects, the composition may include an anion-responsive organogel, a benzaldehyde based gelator, etc.

In aspects, the composition may be configured such that at a first temperature or environmental state, the composition has a low viscosity suitable for delivery through an elongate delivery catheter to a deployment site in a body at a second temperature or environmental state (e.g., pH, salinity, analyte presence, concentration, etc.). Upon delivery to the second temperature or environmental state, the composition transitions to a high viscosity state, a gel state, a thixotropic state, etc. so as to be more easily retained at the tissue site. In aspects, a composition including a cellulose derivative in accordance with the present disclosure may be configured such that the viscosity of the composition is less than 100 cps, less than 25 cps, less than 5 cps in a first temperature range of 45-50° C., and has a viscosity of greater than 500 cps, greater than 2000 cps, greater than 8000 cps in a temperature range of 35-40° C. In aspects, a composition including a polysaccharide, a starch, a cellulose, derivatives, combinations, or salts thereof in accordance with the present disclosure may be configured such that the viscosity in a tissue ablating medium in accordance with the present disclosure over a temperature range of 35-40° C. may be less than 100 cps, less than 50 cps, less than 5 cps, while the viscosity may be greater than 500 cps, greater than 2000 cps, greater than 8000 cps in the presence of an aqueous solution over the same temperature range. Such a configuration may be advantageous for quick delivery to the tissue site, while offering adequate retention at the site once delivered.

In aspects, the step of heating may be used to alter one or more properties of the composition selected from the adhesive tack, stiffness, bioavailability, hydrophilic properties, hydrophobic properties, anti-thrombogenic properties, antibacterial properties, combinations thereof, or the like. Such changes may be advantageous to provide increased flow during delivery, to adjust adhesion to the delivery catheter walls, to alter the affinity of the composition to the walls of the delivery catheter (i.e., such as to reduce the wall adhesion during delivery), to prevent or accelerate thrombogenic properties of the gel during delivery and/or after delivery, etc.

In aspects, the composition may include one or more of a non-reactive powder, gelatin, proteins, polysaccharides, corn starch, cane sugar, brown sugar, a salt, sodium chloride, potassium chloride, baking soda, silica, treated silica, nanoclay, rice flour, wheat flour, confectioners' sugar, combinations thereof, flow facilitating particles, blends, combinations thereof, or the like. Such additives may be used to adjust the flow characteristics of a composition in accordance with the present disclosure, to adjust the glass transition temperature, the viscosity temperature profile, etc.

In aspects, the composition may include one or more of fibers, a reactive specie, a non-reactive specie, colorants, powders, films, particles, dyes, proteins, biomarkers, conductive particles, antibacterial species, a linking molecule, a silane, a siloxane, a mucoadhesive molecule, a hydrophilic polymer, a polyethylene glycol, an isocyanate, poly(ethylene glycol)-adipic acid esters, combinations thereof, or the like.

In aspects, the composition may include a curable adhesive composition wherein the curing or thermosetting reaction occurs after delivery to the tissue site. Some non-limiting examples of curable gel adhesives include silicone gel adhesive, a polyurethane gel adhesive, an acrylic gel adhesive, a hydrogel adhesive, a hydrocolloid adhesive, a hydrogel adhesive, a fibrin adhesive, combinations thereof, and or the like.

According to aspects, there is provided a delivery system for delivering a composition in accordance with the present disclosure to a tissue site, the delivery system including a catheter (e.g., a fluid delivery catheter, a micro catheter, etc.) including a lumen connecting a distal end to a proximal end thereof in fluid communication, for delivering such fluids to a site in the body, and the like. The catheter may include a thermo-regulating element (e.g., a heating element, a fluid transfer reservoir, a magneto responsive (MR) material, etc.), arranged in intimate contact with the lumen therein (e.g., integrated into a reinforcing element, a reinforcing braid, a monolithic laser patterned hypotube, a lumen lining element, etc.), the thermo-regulating element configured to substantially maintain a first temperature of the composition during delivery thereof through the lumen. The catheter may include an insulating element, arranged around an outer diameter thereof, configured so as to thermally isolate the lumen of the catheter, and/or an included thermo-regulating element from a surrounding fluid, blood, etc.

The delivery system may include a thermally controlled reservoir, coupled to the catheter, the thermally controlled reservoir configured to maintain the composition at a first temperature prior to delivery of the fluid into the lumen of the catheter. In aspects, the thermally controlled reservoir may include a heating/cooling element configured and controlled to maintain the composition at the first temperature (e.g., 40-45° C., 45-50° C., etc.). In aspects, the reservoir may include an energy delivery element, an ultrasonic delivery element, etc., to agitate the composition prior to delivery, the agitation configured so as to reduce the viscosity thereof, prior to delivery into the catheter.

In aspects, the delivery system may include a power injector, a syringe pump, or the like, configured to interact with the reservoir so as to deliver the composition to the tissue site during use.

In aspects, the composition may include chemotherapeutic agent, a cytotoxic agent, an antibody drug conjugate, an anti-neural growth factor, a mitotic inhibitor, a poison, a neurotoxin, or the like.

In aspects, a composition in accordance with the present disclosure may include a toxic substance, ethanol, a small organic molecule, a protein, an enzyme, an amino acid, a bioactive agent (e.g., cells, matrix, viral vectors, DNA, RNA etc.), botulinum toxin (e.g., Botox®), cytokines, one or more growth factors, combinations thereof, or the like.

In aspects, the composition may include a spindle-cell poison (DM-1, DM-4, calicheamicin, monomethyl auristatin F & E), adriamycin, irinotecan metabolite SN-38, doxorubicin, a taxel, paclitaxel, docetaxel, combinations thereof, or the like.

In aspects, the composition may include one or more neurotoxins or neuroblockers, such as ethanol, glutamate, nitric oxide, botulinum toxin, tetanus toxin, tetrodotoxin, tetraethylammonium, chlorotoxin, conotoxin, bungarotoxin, anatoxin-a, curare, polybrominated diphenyl ether, isobutronitrile, hexachlorophene, metaldehyde, propoxur, hexane, styrene, bifenthrin, 251-NBOMe, JWH-018, aluminum, arsenic, ammonia, an NMDA receptor blocker, NSAIDs, an NK-1 receptor blocker, FAAH inhibitor, Na, Ca, K channel modulator (e.g., TRPV1, V3, V4, NaV1.7, NaV1.8, ASIC3, etc.), a cannabinoid receptor blocker (CB1, CB2, etc.), delta opioid agonists, P2X3 inhibitors, P38 kinase, CR845, and the like.

In aspects, the composition may include a nerve blocking agent, a sympathetic nerve blocking agent, a parasympathetic nerve blocking agent, an anticholinergic agent, an antimuscarinic agent, a ganglionic blocker, a neuromuscular blocker, combinations thereof, or the like.

Some non-limiting examples of anticholinergic agents include atropine, benztropine, biperiden, chlorpheniramine, dicyclomine, dimenhydrinate, doxylamine, glycopyrrolate, ipratropium, orphenadrine, oxitropiu, oxybutynin, tolterodine, trihexyphenidyl, scopolamine, solifenacin, tropicamide, bupropion, dextromethorphan, doxacurium, hexamethonium, mecamylamine, tubocurarine, etc.

Some non-limiting examples of cholinergic agents include acetylcholine, bethanechol, carbachol, methacholine, arecoline, nicotine, muscarine, pilocarpine, donepezil, edrophonium, neostigmine, physostigmine, pyridostigmine, rivastigmine, tacrine, caffeine, hyperzine A, echothiophate, isoflurophate, malathion, cisapride, droperidol, domperidone, metoclopramide, risperidone, paliperidone, trazodone, clonidine, methyldopa, propranolol, prazosin, oxymetazoline, and the like.

Some non-limiting examples of beta blockers include alprenolol, bucindolol, carteolol, carvedilol, labetalol, nadolol, oxprenolol, penbutolol, pindolol, propranolol, sotalol, timolol, eucommia, acebutolol, atenolol, betaxolol, bisoprolol, celiprolol, esmolol, metoprolol, nebivolol, butaxamine, ICI-118, ICI-551, SR 59230A, and the like.

Some non-limiting examples of alpha blockers include phenoxybenzamine, phentolaamine, tolazoline, trazodone, antipsychotics, alfuzosin, prazosin, doxazosin, tamsulosin, terazosin, silodosin, atipamezole, idazoxan, mirtazapine, yohimbine, carvedilol, labetalol, and the like.

Some non-limiting examples of antibody drug conjugates includes a conjugate of an antibody (e.g., CD30, CD20, CD19, CD74, GPNMB, Ley, PSMA, CD138, CD56, CD70, CA6, CanAng, SLC44A4, CEACAMS, AGS-16, Anti-Cripto, trastuzumab, rituximab, cetuximab, bevicizumab, etc.) with a cytotoxic agent (e.g., spindle-cell poisons (DM-1, DM-4, calicheamicin, monomethyl auristatin F & E, Adriamycin, irinotecan metabolite SN-38, doxorubicin, etc.).

In aspects, the composition may include an anti-nerve growth factor (NGF), anti-NGF monoclonal antibodies, tanezumab, fulranumab, REGN475, etc.

In aspects, the composition may include a cyclic oligosaccharide, a cyclodextrin (alpha, beta, gamma, etc.). The cyclodextrin may house one or more active agents, tissue ablative agents, antibody drug conjugates, anti-nerve growth factor, neurotoxin, nerve growth factor, poison, cytotoxic agent, or the like. After delivery of a bolus of the composition to a tissue site in a body, the cyclodextrin may facilitate delivery of one or more of the housed agents to the surrounding tissues, or a nearby organ, etc.

In aspects, the composition may include one or more kinase inhibitors or a steroid for treating a local inflammatory response. The composition may include an excipient that binds to the kinase inhibitor and/or steroid so as to regulate the release rate thereof into the surrounding tissues.

In aspects, the composition may include a crosslinking agent, a PVP (poly vinyl pyrrolidone), a functionalized PVP, etc., the crosslinking agent configured to crosslink with one or more components (e.g., a cellulose derivative, etc.) of the composition, when it is brought into contact with an aqueous solution.

In aspects, a composition in accordance with the present disclosure may include a toxin, a neurotoxin, paclitaxel, etc. The paclitaxel may interfere with axonal function and neural regrowth in the vicinity of the injection site, thus assisting with the durability of the therapy. In aspects, the composition may incorporate ethyl alcohol (or an alternative ablating agent), in combination with paclitaxel.

In aspects, a composition in accordance with the present disclosure may include one or more of amiodarone, hydralazine, perhexiline, drugs used to fight cancer, cisplatin, docetaxel, paclitaxel, suramin, vincristine, combinations thereof, or the like.

In aspects, a composition in accordance with the present disclosure may include chloroquine, isoniazid (INH), metronidazole (Flagyl), nitrofurantoin, thalidomide, combinations thereof, or the like.

In aspects, a composition in accordance with the present disclosure may include etanercept, infliximab, leflunomide, combinations thereof, or the like.

In aspects, a composition in accordance with the present disclosure may include an analgesic to affect local neural traffic during the delivery process.

In aspects, a composition in accordance with the present disclosure may include one or more of dapsone, an anticonvulsant (phenytoin), an anti-alcohol drug (disulfiram), a combination thereof, or the like.

In aspects, a composition in accordance with the present disclosure may include one or more of didanosine (Videx®), stavudine (Zerie), zalcitabine (Hivie), arsenic, colchicine, gold, combinations thereof, or the like.

In aspects, a system in accordance with the present disclosure may include a sensory subsystem in accordance with the present disclosure. In aspects, the sensory subsystem may include one or more microelectrodes mounted to the catheter, near the distal tip thereof (i.e., near to the tissue site during a delivery process). The microelectrodes may be configured to capture electrophysiological signals, neural traffic signals, chemical migration margin information, or the like from the delivery site.

In aspects, a system in accordance with the present disclosure may include a processor, the processor coupled to the sensory subsystem, or to signals generated therefrom, the processor configured to condition and/or display one or more signals associated with the delivery process (e.g., margin of the delivered bolus, migration of the composition over time, etc.), physiologic changes (e.g., changes in pH, salinity, water content, changes in a systemically measured surrogate marker for the procedure, blood pressure, glucose levels, renin levels, noradrenalin spillover, etc.), and electrophysiological changes (e.g., changes in neural traffic, changes in nerve function, changes in one or more nerve signals, changes in the character of nearby action potentials, changes in the phasic character of the action potentials, biphasic to monophasic transitions in such action potentials, etc.).

In aspects, the processor may include a function to determine the proportion of signals measured from the nerves associated with group I, group II, group III, and/or group IV nerve types. In aspects, the processor may be configured to deliver energy and/or the substance to the tissues until a significant drop in group IV traffic is determined by the function from one or more of the sensory signals.

In aspects, a method in accordance with the present disclosure may include determining the proportion of signals measured from the nerves associated with group I, group II, group III, and/or group IV nerve types, the ablating and/or defunctionalizing dependent upon the proportion. In aspects, the step of ablating and/or defunctionalizing may be adapted so as to stop based upon a substantial drop in group IV traffic (e.g., such as by halting delivery of the substance, by delivering a neutralizing substance, by delivering an antidote, by withdrawing the delivery element, etc.). In aspects, the determination of group traffic may include analyzing the shapes and/or propagation characteristics of action potentials as measured amongst a plurality of electrodes in accordance with the present disclosure.

In aspects, the method may include monitoring the extent of effect that a composition has on the group I, group II, or group III traffic as measured near to, or coupled to the tissue site. In aspects, the method may include halting delivery of the composition if the traffic changes are not as desired for the given therapy (i.e., if the changes in group I or group II traffic are sufficiently higher than accepted).

In aspects, the method may include ablating and/or defunctionalizing one or more nerves associated with group III or group IV, while substantially preserving one or more nerves associated with group I or group II. Such ablation and/or defunctionalization may be achieved through selection of active substances in a composition in accordance with the present disclosure, and precise delivery and optional monitoring of the effect of the composition to the tissue site in the body.

According to aspects, there is provided a system, a composition, and a method each in accordance with the present disclosure for treating one or more classifications of nerves, muscles, and/or receptors at sites within a body to alter a neuroendocrine, neural, or cardiac function thereof. The method includes selecting a composition in accordance with the present disclosure, the composition being selective to the target nerve, muscle, or receptors, delivering the composition to the sites within the body, and optionally monitoring one or more of nerve traffic, a physiologic surrogate parameter related to the nerve traffic, or the like to determine the extent of treatment. The composition may be delivered, and optionally the effects monitored with a system in accordance with the present disclosure.

According to aspects, there is provided a method for determining the extent of a treatment at a site within a body, the method including administering a composition in accordance with the present disclosure to the site, and monitoring a change in neural traffic in the vicinity of the site, the neural traffic changing with the extent of the treatment, and analyzing the change in neural traffic to determine if the treatment is substantially complete. In aspects, the analyzing may include analyzing one or more action potentials in the neural traffic to determine the type of nerves affected by the treatment, analyzing the action potentials to determine a change in spectral composition thereof as effected by the treatment, analyzing the propagation velocity of one or more action potentials to determine the extent of the change therein as caused by the treatment.

The step of analyzing the action potentials may include analyzing a change in the rise time of the action potential, a change in the pulse width of the action potential, a change in the spectral content of the action potential, a change in the periodicity of similar action potentials (as measured at a one or more monitoring sites around the treatment site), a change in the number of similar action potentials per unit of time, a change in the polarity of action potentials (e.g., a change in the number or percentage of positive polarity action potentials, a change in the number or percentage of negative polarity action potentials, a change in the polarity of the aggregate traffic measurement, etc.).

In aspects, the composition may be configured to form at least a partial collagen block at the delivery site. Such a collagen block may be formed by healing of tissues after a sufficiently disruptive ablation event, caused by an overexpression of a scar growth factor, caused by prolonged healing and inflammatory response around one or more constituents in the composition (such as an ink, a contrast agent, a filler, a silica micro or nano particle, etc.). Such formation of a fibrotic or collagen block may be advantageous to limit nerve regrowth after the treatment, to block cell migration along a pre-existing neural pathway, etc.

In aspects, the composition may include a poison, neurotoxin, or anti-nerve growth factor, configured to down regulate local nerve growth and/or limit local nerve regrowth at the delivery site. In aspects, the composition may include an anti-nerve growth factor, a microtubule disruptor, paclitaxel, or the like to limit nerve regrowth and/or neural sprouting in the vicinity of the delivery site. Such an approach may be advantageous to limit neuritis (nerve regrowth with heightened pain, often perceived as worse than before the surgery, which can occur during pain management treatments), anesthesia dolorosa (patient complaints of distressing numbness), and side effects associated with poorly controlled treatments (e.g., such as may be caused by migration of prior art therapeutic agents).

In aspects, the composition may include a polymer, a precipitating component, and/or gelating agent in accordance with the present disclosure. Such a polymer, precipitating component, or gelating agent may be configured to form a skin around a bolus of the composition after delivery to a treatment site. The skin may be configured with a permeability configured to provide a slow leakage of an active agent (e.g., a tissue ablating agent, an anti-nerve growth factor, a nerve growth factor, a toxic substance, a poison, a neurotoxin, etc.) into the surrounding tissues for a period of time following the delivery of the bolus thereto.

In aspects, the skin forming component may be biodegradable, metabolizable (e.g., a sugar, a carbohydrate, sucrose, a fatty acid, a starch, etc.), etc.

In aspects, a composition in accordance with the present disclosure may include, a cellulose derivative, the cellulose derivative (e.g., ethyl cellulose, a hydroxyethylcellulose, etc.) with limited solubility or being substantially insoluble in an aqueous solution. Upon delivery of the composition to a tissue site in a body, the cellulose derivative may form a skin around the bolus, thus creating a diffusion barrier. In aspects, the cellulose derivative may be configured so as to readily breakdown and metabolize in the body, such that only a temporary barrier is formed upon injection of the composition.

In aspects, the polymer, precipitating component, and/or gelating agent may be configured to form a substantially strong barrier in the presence of a first medium (e.g., blood, urine, air, lymph, bile, etc.), and a substantially weak barrier in the presence of a second medium (e.g., interstitial fluid, extracellular fluid, water, fatty tissue, etc.), such that release of the active agent is provided towards the second medium. In aspects, a cellulose derivative in accordance with the present disclosure may be configured to form a plug in the presence of a first medium (e.g., blood), and to remain within the solution of the composition in the presence of the second medium (e.g., interstitial fluid). Such a configuration may be advantageous to limit flashback along an injection pathway, to limit migration of the composition into a nearby blood vessel, etc.

In aspects, a delivery system and/or a catheter in accordance with the present disclosure may include a hollow stem delivery tube configured for placement into the wall of a vessel, and a composition, configured to form a sack-like bolus after passage through the stem, the delivery system configured to pierce the stem through and embed the stem into the wall of a lumen, the sack-like bolus to form a fluid reservoir on the other side thereof. After placement, the composition may slowly transfer from the fluid reservoir, through the hollow stem, and into the vessel. Such a configuration may be advantageous to slowly release an active agent into a vessel within a body.

In aspects, the delivery system may include an anchor, configured for placement into the wall, the anchor coupled to the hollow stem delivery tube, the hollow stem and/or the anchor providing fluid communication between the fluid reservoir and the vessel.

In aspects, the hollow stem, anchor, or the like may be biodegradable. The hollow stem, anchor, or the like may be formed from a biodegradable polymer (e.g., PLA, PLGA, polysaccharides, collagen, etc.), a magnesium or potassium based structure, or the like.

In aspects, the delivery system, hollow stem, anchor, or the like may be configured (such as via shape, composition, permeability, etc.) so as to slowly release a pattern of a medicament into a tissue, organ, lumen wall, etc. in the body.

In aspects, a composition in accordance with the present disclosure may be used to treat one or more of ablation, growth stimulation, cell or tissue sustenance, modification of cells, altering neural traffic, of a tissue or any other biological tissue present at a delivery site. The composition may be formulated to as to control the rate or release, migration, retain treatment at a delivery site, etc.

In aspects, the composition may be configured to form a complete ablation of adjacent tissues, growth stimulation, cell or tissue sustenance, or modification of cells, tissue or any other biological tissue present at the delivery site.

The composition may be biostable or bioerodable, biocompatible with minimal toxicity to surrounding tissues except for the targeted tissue type, configured so as to cause an inflammatory or otherwise cytotoxic response upon delivery.

In aspects, the composition may be configured so as to substantially minimize migration upon delivery to a tissue site in a body. An associated delivery system in accordance with the present disclosure may be configured to lay down, inject, etc. a composition in accordance with the present disclosure in one or more physical forms, configurations, sizes, or shapes on biological surfaces or within a three dimensional volume of tissue (e.g., to form a ring, a fence, a wall, to shape electrophysiological signal traffic throughout the volume of tissue, to target specific sites within the volume of tissue, to isolate a region of the tissue, etc.).

In aspects, a delivery system in accordance with the present disclosure may include a needle, through which a composition may be delivered to a tissue surface, or volume, the needle shaped, and configured to shape the composition (e.g., as a spherical shape, a line, a ring, along a pathway, a fence, bell shapes, elliptical shapes, etc.). In aspects, the needle may include one or more ports through which a composition may be delivered.

According to aspects, there is provided an injection device for delivering a composition in accordance with the present disclosure to one or more tissue sites in a body, the injection device including a needle, the needle including one or more lumens for delivering the composition. The needle may be configured with an occluded tip, or an open tip, may include one or more ports along a wall thereof, may be shaped so as to pattern the composition into a shaped pattern along a tissue surface, or into a three dimensional volume of tissue, shaped so as to adjust an injection rate, size, shape, dose, or distribution of the pattern, etc.

Such a configuration may be used to control a pattern of injection: spherical, linear, ellipsoidal, or other two-dimensional/three-dimensional shape, which may be advantageous for treating a tissue, a region of tissue, a pattern of tissue along a wall, to deliver a medicament to a specific site along a wall of an organ, through a vessel, into a region of tissue beyond a vessel, along a region of muscle, to isolate a region of muscle, to treat a neuromuscular interface, etc.

In aspects, a delivery system/an injection device in accordance with the present disclosure may include one or more sensing components, the sensing components configured to monitor one or more of neural activity, autonomic nervous system activity, afferent nerve traffic, efferent nerve traffic, sympathetic nerve traffic, parasympathetic nerve traffic, electromyographic activity, smooth muscle activity, cardiac muscle electrophysiological activity, intracardiac activity (myopotentials, His-Purkinje pathways), transition between different types of tissue (e.g., such as by impedance measurement, local stiffness measurement, light scatter measurement, etc.), combinations thereof, or the like. In aspects, the sensing component may include one or more electrodes, each electrode configured to sample the activity locally around the tip of an injection device, near to an injection site to determine the margins of the effect of the injection, at a remote site to determine the effect of a delivered composition, etc. One or more of the sensing components may be applied along a needle, a plurality of sensing components may be patterned along and around the needle, etc. In aspects, a plurality of sensing components may be applied along a length of a needle, the sensing components coupled with microelectronics so as to measure impedance, Nernst potentials, biopotentials, etc. there between. Such microelectronics may be configured to determine when one or more sensing components have passed into a lumen wall, is in contact with a fluid (such as blood), has passed from a first tissue type, into a second tissue type, etc. Such information may be used to help guide the needle towards a target site, to determine if the needle tip has left the lumen through which it has been guided to the target site, if the needle tip has been guided to a target neural structure, etc.

In aspects, a composition in accordance with the present disclosure may be configured to deliver a matrix of a tissue ablating agent into a volume of tissue. In aspects, the composition may be configured as an electrically insulating composition, the sensing component configured to determine the margins of the bolus (e.g., via monitoring conductivity between two or more electrodes in the vicinity of the delivery site, etc.).

In aspects, a composition in accordance with the present disclosure may include one or more electronic or ionic conducting components (e.g., a conjugated polymer, a salt, a conducting composite, etc.). In aspects, the composition may be configured such that the electronic or ionic conducting component may be polymerized in place after delivery to a treatment site, may be configured so as to interrupt local electrophysiological processes (e.g., interrupt signal traffic through a volume of cardiac tissue, along a nerve plexus, etc.). In aspects, the conducting component may be electropolymerized in place, using one or more electrodes in close proximity thereto, and/or a remote return electrode placed elsewhere on or in the body.

In aspects, the composition may be configured so as to limit migration from an injection site to a distance of less than approximately 3 mm, less than approximately 2 mm, less than approximately 1 mm, etc. In aspects, the composition may be formulated such that the migration is sufficient so as to link adjacently placed boluses, but not so much so as to limit collateral damage during the treatment process. In aspects, the composition may include one or more contrast agents (e.g., a radiological contrast agent, an ultrasound contrast agent, a MR contrast agent, a fluoroscopic contrast agent, etc.) in accordance with the present disclosure, such that the placement and/or migration of the boluses may be visualized during a procedure.

In aspects, the procedure may be used to treat one or more sites along an organ wall (e.g., a bladder, a urethra, a ureter, a prostate, a testicle, a heart, a liver, a stomach, a bowel, a biliary tract, a pancreas, a kidney, an artery, a vein, a vessel, a lymph node, a bone, a periosteal space, a lung, a bronchial tract, a gland, a ganglion, a region of the limbic brain, an ovary, a uterus, etc.). In aspects, the composition may include a contrast agent in accordance with the present disclosure, such that an operator may visualize where the composition has been delivered along the organ wall, where it has migrated to, etc.

In aspects, a composition in accordance with the present disclosure may include a salt, a hypertonic solution, or the like.

In aspects, a sensory component in accordance with the present disclosure may be used to determine the ischemic border zones/the isthmus for ischemic myocardium using one or more sensors on the tip of a delivery system or injection device in accordance with the present disclosure. Once the border zone is detected, the delivery system or injection device may deliver one or more boluses of a composition in accordance with the present disclosure to treat the border. Optionally, the sensory component may be configured to monitor the effect of the composition on the electrophysiological activity along the border, so as to determine when the treatment has been completed.

In aspects, the composition may be configured to perform a cryoablative procedure on tissues in the vicinity thereof (i.e., by delivery of a super-cooled composition, a composition for providing a localized endothermic reaction, etc.). In aspects, such cryoablative compositions may include one or more metal complexes, a metal complex in combination with a salt solution, etc. In aspects, the composition may be configured as a two part solution, the two parts mixed before, during, and/or after delivery to the tissue site.

In aspects, a composition in accordance with the present disclosure may include a phase change component, such as a polymerizing element, a gel forming element, a gelling agent, an ion exchange gel, etc. In aspects, the phase change component may be configured as follows. The composition may be delivered to the tissue site as a fluid, the fluid surrounding a neural structure of interest. Upon delivery, the phase change component of the composition transitions to a gel state, a polymerization reaction takes place, etc. and the phase change component transitions into a substantially solid mass, effectively surrounding the neural structure of interest (e.g., a ganglion, a nerve plexus, etc.). In aspects, the composition may include a hypertonic or hypotonic solution, a solvent, etc. such that exchange of the solution or solvent with the surroundings results in a net shrinkage of the substantially solid mass after placement around the neural structure. Such shrinkage may effectively compress the neural structure, thereby instilling a neural block thereto (i.e., effectively blocking traffic along the neural structures while otherwise minimizing necrosis and cell death of the neural structures). Such a configuration may be advantageous for affecting neurological function at a tissue site while minimizing associated nerve growth, which may occur in response to local inflammation, damage to the nerves, etc.

In aspects, the composition may include a gelling agent such as a hydrophilic polymer, a free radical forming component, a crosslinking polymer system, a 2 part gel system, or the like. In aspects, a delivery system in accordance with the present disclosure may include a mixing element, a static mixer, etc. in order to mix the parts prior to or during delivery to a tissue site in the body.

In aspects, a composition, a delivery system, or a method each in accordance with the present disclosure may be applied to treatment of several tissues or disease states within a body, such as the gastrointestinal system, the cardiac system, the neuroendocrine system, the renal system, the ANS (autonomic nervous system), the CNS (central nervous system), a peripheral nerve, a neuromuscular junction, a cancerous tumor, a cosmetic procedure (i.e., combined botox and bulking applications, etc.), and the like.

Some non-limiting examples of treatments for the gastrointestinal system include, treatment of electrical storm in a bowel, treatment of an autoimmune disorder, treatment of LUTS, overactive bladder (e.g., treatment of receptors in the bladder muscle, in the neural pathway between the bladder and local ganglia, along a muscle wall of a urethra, etc.), incontinence (e.g. urinary or fecal incontinence, adjustment of sphincter tone, etc.), treatment of ulcerations (e.g. via injection of growth factors, topical application thereof, etc.), or the like.

Some non-limiting examples of cardiac applications are for the treatment of atrial arrhythmias (AFib, SVT, APCs, AVNRT, WPW/Accessory tract, AVN Ablation), treatment of aFib in specific patterns (e.g., 'dots' or spherical patterns, linear patterns, two-dimensional or three-dimensional shapes, combined with contrast agent to visualize the injected pattern under fluoroscopy, x-ray, MR, or ultrasound-based imaging technologies, etc.). In MR applications, the composition may include one or more ferromagnetic components (e.g., an iron or iron oxide complex, a gadolinium complex, etc.), configured to assist with visualization of the placement of composition into a tissue site, etc.

Such applications may be further improved with combination of a sensing component in accordance with the present disclosure to assess/avoid regions of the esophagus (for example, induce a swallow and sense esophageal EMG (electromyography) within the heart wall prior to injection, to ensure adequate margins, etc.).

Some additional cardiac applications include treatment of ventricular arrhythmias (VT, VF, PVCs), such as may be accomplished by sensing regions of slowed conduction and ablate selectively with a composition in accordance with the present disclosure, follow this region with further sensing to ablate the entire affected zone. Such treatments may be enhanced with combination of a composition in accordance with the present disclosure and a sensory component in accordance with the present disclosure (such as may be unipolar, bipolar, multipolar, etc. configured to determine epicardial activity during treatment, to determine the extent of the composition treatment, to assist with determining the next site to treat, etc.).

Some additional cardiac applications include treatment of one or more autonomic plexi in the vicinity of the heart or coupled thereto. Such structures related to aFib and other arrhythmogenic foci that are autonomic dependent include ganglia, vagal (hypervagotonia, etc.) and dysautonomias, POTS, etc. Such structures may be targeted along/near a vein of Marshall, along the epicardium, along the pericardium, etc.

Some non-limiting applications related to neuroendocrine remodulation include renal nerve treatments, renal artery treatment, treatment of renal accessory vessels, adrenal arteries, carotid sinus, carotid body, autonomic ganglia (e.g., celiac, carotid, etc.), and the like.

Some additional non-limiting applications include treatment of one or more neuroendocrine aspects of congestive heart failure, hypertension, metabolic syndrome (MSx), hypogonadism, inflammatory diseases, infiltrative diseases, infection, chronic wounds, Sjogren's syndrome, Gaucher disease, Parkinson's disease, epilepsy, depression, tumors, stroke, diabetes, cancer, pancreatitis, islet cell tumors, nephrotic syndrome, kidney stones, lower urinary tract disorders, urinary incontinence, urinary tract infection, neurogenic bladder disorders, male or female fertility, impotence, premature ejaculation, prostate cancer, ovary cancer, uterine cancer, gastrointestinal ulcers, acid reflux disorders, celiac disease, irritable bowel syndrome, gastrointestinal cancers, tuberculosis, cystic fibrosis, pulmonary hypertension, chronic obstructive pulmonary disease, lung cancer, coronary artery disease, arrhythmias, and chronic renal failure. Treatment of abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and diabetes. Additional treatments may include augmentation of function or a disease state associated with a vessel, an artery, a vein, a tubule, a renal artery, an arteriole, a venule, a duct, a chamber, a pocket, a tubule, a bowel, a urethra, an organ, a combination thereof, or the like.

In aspects, applications include treatment or alteration of function of one or more organs, some non-limiting examples of which are a kidney, a prostate, a testicle, a pancreas, a liver, a lung, a bowel wall, a stomach wall, a gland, a neural body, a carotid body, a gall bladder, a small intestine, a large intestine, a spleen, a pancreas, a bladder, an adrenal gland, a uterus, lymph node, a ganglion, combinations thereof, and the like. Treatment of one or more symptoms, neurological, and/or neuroendocrine contributions to lower urinary tract symptoms (LUTS) secondary to benign prostatic hyperplasia (BPH), chronic prostatitis (CP), hypogonadism (HG), nocturia, prostate cancer (PrCa), and erectile dysfunction (ED), micturition, incontinence, frequency, pain, bladder capacity, and/or configured to modulate neural activity in at least a portion of the bladder wall, or the like.

Such compositions, delivery systems, and/or methods in accordance with the present disclosure may be used for treatment so as to affect the growth rate, hormone secretion rates, or development of an organ (e.g., a prostate, a testicle, etc.), or a tumor (e.g., a prostate cancer tumor, a perineural invading cancerous tumor, lymphatic invading tumors, etc.), lymphatic ducts, lymphatic nodes, or the like, to alter functions including a sensation (e.g., a hunger sensation, an urge to urinate, pain, etc.), a tremor, altering release/secretion of a chemical substance (e.g., acid, hormones, toxins, bile, enzymes, surfactants, sebum, renin, etc. from a secretory cell), altering smooth muscle tone, or the like. Such a composition, system, or method may be used to treat a disease of the gall bladder, renal system, metabolic functions, gastrointestinal function, to augment hunger sensation, reduce tone, combinations thereof, and the like.

In aspects, some non-limiting examples of medical conditions that can be treated according to the present disclosure include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, or abnormal malformational causes.

The present systems and methods also encompass enhancing the therapeutic effects of other therapies, such as methods and systems working in conjunction with a pharmaceutical agent or other therapies to augment, enhance, improve, or facilitate other therapies (adjunctive therapies) as well as reducing/minimize and counteracting side effects, complications and adverse reactions for any therapies involved in treating the above-mentioned medical conditions.

In aspects, liver function which may be augmented by a treatment and/or monitored in accordance with the present disclosure includes glucose storage/release, metabolic sensing (and related signal traffic to the brain related thereto), glucoregulatory function, afferent vagal activity reaching the brain, chemoreceptor function (or related signal traffic associated therewith), lipid sensing/synthesis, regulation of hepatic insulin sensitizing substance, afferent traffic augmentation associated with glucosensors (i.e., primarily in the region of the portal vein, etc.), protein sensing, GLP-1, leptin, CCK, FFA, PPAR alpha and gamma, glycogenolysis, gluconeogenesis, VLDL secretion, ketogenesis, hypoglucemia sensing, or the like.

In aspects, one or more compositions, delivery systems, and/or methods in accordance with the present disclosure may be used to treat cancer of the prostate, pancreas, breast, cervix, ovaries, bladder, bone, combinations thereof, pain associated therewith, or the like. Such applications may include delivery of compositions to slow, to reverse, and/or to prevent perineural and/or lymphatic vessel invasion of a cancerous tumor into a surrounding neural and/or lymphatic microenvironment, to interrupt, decrease, and/or stop neural communication to/from a cancerous tumor and/or the microenvironment surrounding the tumor to a remote site within a body, etc.

In aspects, one or more systems, methods, or compositions in accordance with the present disclosure may be used to treat one or more conditions of the central nervous system, the enteric nervous system, the limbic brain, etc. Some non-limiting examples include treatment of seizure foci, hyperactive neurological regions, neuroendocrine/GI structures, pancreas/b-islet cells for DM, production of ghrelin and other GI hormones, combinations thereof, or the like.

In aspects, one or more non-limiting applications in oncology include sensing and ablation of CNS tumors with chronic release (e.g., CNS tumor with absence of electrical signals indicative of a tumor region, etc.). In aspects, the tumor margin may be determined by monitoring the electrical signals associated with the electrophysiologic activity of nearby cells, the activity changing across the margin of the tumor. In aspects, the tumor margin may contribute to considerable neural sprouting, the electrical signals measured by a device in accordance with the present disclosure may change considerably (i.e., as compared with normal tissue electrophysiologic activity), in the vicinity of the neural sprouting region.

In aspects, one or more non-limiting cosmetic applications include the combination of neurotoxic function with a filler, chronic release of a neurotoxin (e.g., release of botulinum toxin, etc.), combination of bulking agents with neurotoxins (e.g., for treatment of sphincter spasm, sphincter bulking, wrinkle removal, denervation of the platysma muscle, etc.).

In aspects, a delivery system or injection device in accordance with the present disclosure may take the form of a guidewire or a catheter. The guidewire may be dimensioned and configured for placement within a lumen of a body at and/or beyond a surgical site and/or anatomical site of interest, so as to monitor one or more physiologic signals near the tip thereof. In aspects, the guidewire may provide a pathway for delivery of a second surgical device to the surgical site.

In aspects, a guidewire in accordance with the present disclosure may include one or more energy delivery means for delivering energy to an anatomical site within and/or beyond the wall of a lumen into which the guidewire tip has been placed.

In aspects, a guidewire in accordance with the present disclosure may include one or more sensors (e.g., as located on a micro-tool-tip, a clamp, a hook, a wire element, an electrode in a matrix, etc.) near to the tip thereof. One or more sensors may include a pressure sensor, a tonal sensor, a temperature sensor, an electrode (e.g., sized, oriented, and configured to interact with a local tissue site, provide a stimulus thereto, measure a potential therefrom, monitor current to/from the tissues, to measure, dependent on configuration and design, a bioimpedance, measure an evoked potential, an electromyographic signal [EMG], an electrocardiographic signal [ECG], an extracellular potential form a nearby neural structure, a local field potential, an extracellular action potential, a mechanomyographic signal [MMG], local neural traffic, local sympathetic nerve traffic, local parasympathetic nerve traffic, afferent nerve traffic, efferent nerve traffic, etc.), an acoustic sensor, an oxygen saturation sensor, or the like.

In aspects, the catheter or guidewire may be equipped with a substance eluting element, configured to deliver a composition in accordance with the present disclosure, a substance, a medicament, a denervating substance, or the like into the target organ, into the tissues surrounding the wall of the lumen, etc.

In aspects, the energy and/or substance is delivered to interrupt and/or augment neural traffic along one or more nerves coupled to the target organ. In aspects, the energy and/or substance is provided so as to block nerve traffic to and/or from the organ along the lumen into which the distal tip has been inserted.

In aspects, the substance may include a neural agonist or neural antagonist. The substance may be delivered to a site whereby the active agent (agonist/antagonist) may be released into the target neural structures, so as to augment neural function over a prolonged period of time. Such an approach may be advantageous to selectively treat neural structures without releasing significant amounts of the agonist/antagonist into the general blood stream of a subject (i.e., so as to treat a target sight with maximum efficacy while minimizing systemic levels of the agonist/antagonist).

In aspects, a system in accordance with the present disclosure may be used to treat pain, pain associated with perineural invasion of a cancerous tumor, or the like. Such a system may be advantageous for treating such pain durably and with minimal side effects. Furthermore, such a system may be directed to treat nerves in the vicinity of the tumor without affecting ganglia or CNS structures, thus reducing the chances of side effects, complications, and the like.

In aspects, a system, device, and/or method in accordance with the present disclosure may be used to treat and/or slow the progression of a cancerous tumor. Some non-limiting examples of such cancer that may be treated include cancer of the prostate, pancreas, breast, colon, skin, liver, esophagus, cervix, bone, urogenitals, lung, and the like. In aspects, the progression may be slowed by blocking of neural and/or lymphatic pathways as may otherwise provide conduits for metastasizing tumor cells.

In aspects, a system, device, and/or method in accordance with the present disclosure may be used to slow, hinder, and/or prevent perineural or pen-lymphatic invasion of a cancerous tumor into a surrounding nerve or lymphatic structure.

In aspects, a system, device, and/or method in accordance with the present disclosure may be used to interrupt, decrease, and/or stop neural communication to a cancerous tumor and/or the microenvironment surrounding the tumor (i.e., to interrupt nerve traffic to/from a cancerous tumor or the tissues thereby to the rest of the body).

In aspects, a system, device, and/or method in accordance with the present disclosure may be used to decrease pain signals communicated by nerves in the vicinity of the organ and/or tumor to one or more neural circuits, ganglia, etc.

In aspects, a system, device, and/or method in accordance with the present disclosure may be used to block, deaden, and/or destroy nerves in the vicinity of a tumor and/or surrounding tissues.

In aspects, a system, device, and/or method in accordance with the present disclosure may be used to slow or even halt tumorigenesis of cancerous tissue.

In aspects, a composition and/or delivery method in accordance with the present disclosure may be configured to form a physical barrier (i.e., lesion, a collagen block, etc.) along a neural structure and/or a lymphatic structure in a body.

In aspects, the composition may include an antibody drug conjugate (ADC), a chemotherapeutic agent, a toxin, a neurotoxin, etc. In aspects, the ADC may be configured to affect the function of a region or tissue type within the vicinity of the organ alternatively to the other tissues within the vicinity thereof. In aspects, the composition may include a sugar attached to a therapeutic agent to mask the therapeutic agent, such that it is to be taken up by the region of tissue (i.e., appear as a sugar, a friendly protein, etc.). Such a configuration provides a method for delivering a highly potent medicament directly to a tissue of interest (i.e., directly into a tumor), so as to enhance the bioavailability thereof, and to minimize the systemic dosage required in order to achieve significant therapeutic concentrations thereof within the region of tissue.

In aspects, the composition may be delivered at a rate of less than 1 mg/sec, 1 mg/min, 1 mg/hr, 0.01 mg/hr, less than 1 μg/hr, or the like. Such a configuration may be important so as to minimize local stress and damage caused by the introduction of the composition into the microenvironment of the tissue of interest.

In aspects, the composition may be formulated such that the ablative agent is released from a delivered bolus (e.g., such as a 100 mg bolus) into the surrounding tissues at a rate of less than 500 mg/sec, less than 50 mg/sec, less than 500 mg/min, less than 100 μg/hr, or the like. In aspects, a slow release formulation may be used so as to functionally disable a tissue site in a body without causing local cell death. Such a configuration may be advantageous for performing a substantially durable and reversible treatment of tissues in a body. In aspects, an active agent may include a phenol, an alcohol, etc. and the composition may include a metabolically cleavable bond (e.g., a sugar, a cellulose chain, etc.) to which the active agent may be bound. Such slow metabolic cleavage of the bonds may allow for exceptionally slow release of the active agent into the surrounding tissues. Such a configuration may be advantageous to control ethanol elution in time and space near to a target tissue site in a body over a period of seconds, minutes, hours, days, weeks, or even longer.

In aspects, a delivery system in accordance with the present disclosure may include a catheter and/or a guidewire configured for percutaneous access to the arteries, veins, or lumens, of a body, for delivery through one or more arteries of the body to the vicinity of the target organ.

In aspects, one or more energy delivery elements, sensing elements, a diameter of the catheter, guidewire, or the like may be sized and arranged such that it may be placed within an artery, vein in a region near the target organ, within the parenchyma of the target organ, into a vessel in the periosteal space of a bone, and/or through a foramen of a bone. In aspects, the delivery elements and/or sensing elements, catheter, guidewire, etc. may be sized and dimensioned such that a characteristic diameter thereof is less than 2 mm, less than 1 mm, less than 0.75 mm, less than 0.5 mm, less than 0.3 mm, or the like.

In aspects, a method in accordance with the present disclosure may be used to treat prostate cancer, pancreatic cancer, breast cancer, colon cancer, cervical cancer, ovarian cancer, bladder cancer, bone cancer, or the like.

In aspects, a system in accordance with the present disclosure may include a substance delivery aspect, configured for elution of a substance into the vicinity of the target.

In aspects, the micro-tool tip may include a substance delivery needle for providing a drug substance to one or more of the nerves to perform the ablation.

In aspects, the micro-tool tip may include an energy delivery means, for providing an ablating current, ultrasound energy, high intensity focused ultrasound (HIFU), MR guided HIFU, thermal energy, cryogenic change, etc. to one or more of the nerves.

In aspects, the delivery system may include a signal conditioning circuit and a processor for identifying the presence and/or characterizing one or more of the nerves, to generate a feedback signal therefrom, and to coordinate the energy or substance delivery based upon the feedback signal.

In aspects, the micro-tool tip may have a characteristic diameter of less than 2 mm, less than 1 mm, less than 0.5 mm, less than 0.25 mm, or the like to facilitate placement into the vessel.

In aspects, the micro-tool tip may include one or more electrodes in accordance with the present disclosure. One or more of the electrodes may be sized and dimensioned to measure the signal, and/or one or more of the electrodes may be sized and dimensioned to stimulate and/or ablate one or more of the nerves.

In aspects, the micro-tool tip may include a plurality of electrodes, each electrode configured for sensing an electrophysiological signal in accordance with the present disclosure in the vicinity thereof, the electrodes electrically isolated from each other such that the collection of locally collected signals may be used to determine activity over a region of tissues in the vicinity of the vessel.

EXAMPLES AND FIGURES

Figure 1B:
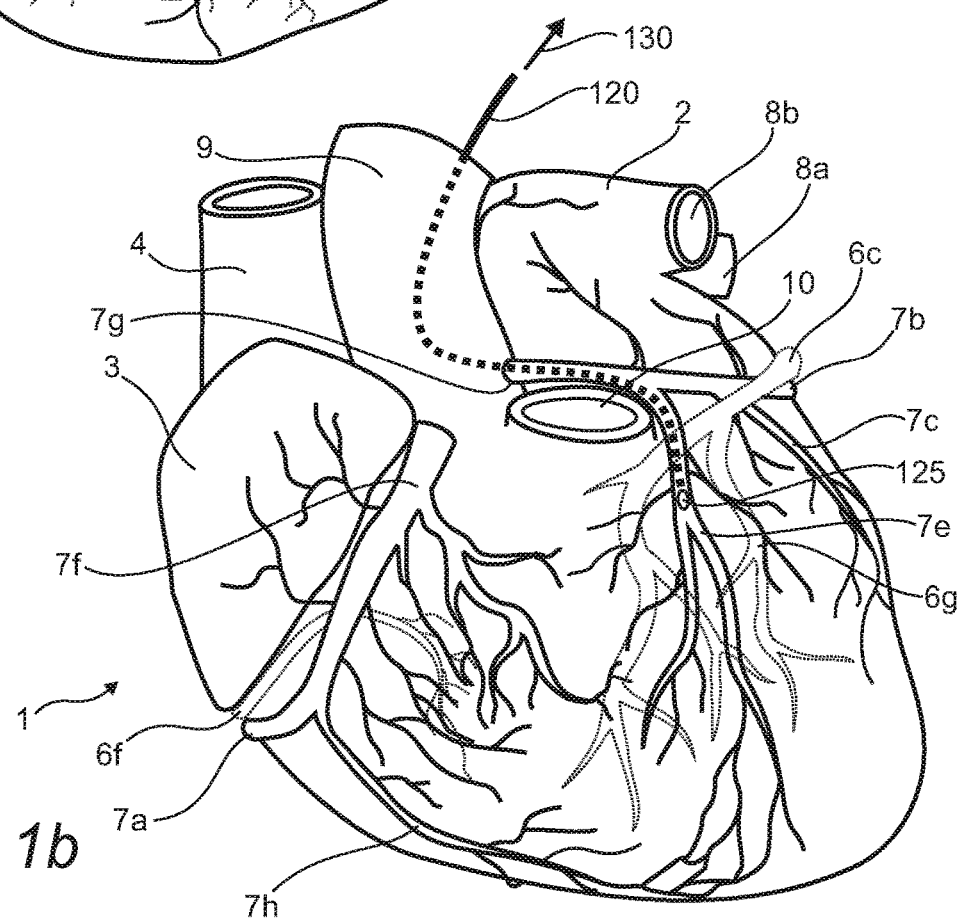

FIGS. 1a-b show catheter access routes into various coronary vessels of a human heart 1. The coronary vessels are arranged around the heart along with autonomic innervation, thus allowing access to the innervation for methods and devices in accordance with the present disclosure. Thus the coronary vessels may provide a pathway to reach diseased sites of innervation around the heart, so as to provide treatment with an associated interventional device. FIG. 1a shows the heart 1 with a left atrium 2 coupled to four pulmonary veins 8a-d, a right atrium 3 coupled with a superior vena cava 4 and an inferior vena cava 5. The coronary sinus 6a may be accessible through the right atrium 3 and connects to other coronary veins including a small cardiac vein 6f, a middle cardiac vein 6d, a left posterior ventricular vein 6b, a great cardiac vein 6c, an oblique vein 6e of the left atrium 2, and a left marginal vein 6g (shown in FIG. 1b). Also shown is the circumflex branch of the right coronary artery 7a, the posterior interventricular branch of the right coronary artery 7i, the posterior left ventricular branch of the left coronary artery 7c, the circumflex branch of the left coronary artery 7b, and the posterior interventricular branch of the left coronary artery 7d. A device 100 in accordance with the present disclosure (e.g., a sensing catheter, a delivery catheter, a combination thereof, etc.) is shown with an effector 105 placed within the coronary sinus 6a, and in communication with an external controller 110. The effector 105, may include one or more sensing elements, one or more delivery needles, one or more secondary sensors, etc. each in accordance with the present disclosure. The effector 105 may include one or more radiopaque markers to assist with locating the effector 105 in relation to other features on the heart 1.

In aspects, the effector 105 may include a delivery element in accordance with the present disclosure, the delivery element configured so as to be deployable through the wall of the coronary vein in which the effector 105 is placed, so as to deliver a substance, energy, etc. to a nearby tissue, a vein wall, adventitia around the vein, a region of tissue, a muscle, a region of tissue on the left atrium 2, a diseased region, a lesion, or the like.

In aspects the effector 105 may include one or more sensing elements in accordance with the present disclosure, each sensing element configured to measure a local electrophysiologic signal to assist in the localization of therapeutic targets, localize sympathetic, parasympathetic, or somatosensory nerves, assess local neural traffic, assess local smooth muscle function, assess local cardiac function, map functionality, map neural interconnectivity, assess interconnection of neural traffic, find local ganglia, apply signals, substances, form a blockage, or the like for one or more diagnostic tests, support therapy and confirm delivery of therapy, or the like. In aspects, the sensory catheter may be integrated with a therapeutic modality in accordance with the present disclosure to provide a full feedback integrated device.

Such a system may be advantageous for providing ultra-high spatial and spectral fidelity mapping of the local neural structures, and functional interface with the cardiac nerves for diagnostic, and therapeutic purposes.

In aspects, a coronary venous approach may be advantageous for accessing one or more sensory nerves, one or more parasympathetic nerves, or the like along the outer surface of the heart. Such nerves may be treated with a device in accordance with the present disclosure to reduce cardiac pain, augment local coronary vein vasoconstriction/vasodilation, assess local neural function, apply one or more stress tests to a local coronary vein, or the like.

FIG. 1b illustrates a heart 1 coupled with an ascending aorta 9, a left coronary artery 7b and a right coronary artery 7f coupled thereto. The left coronary artery 7b is shown coupled to the anterior interventricular branch 7e and the left marginal branch 7c coronary arteries. The right coronary artery 7f is shown coupled to the right marginal branch 7h and the posterior interventricular branch 7a. Also shown are coronary veins including the small cardiac vein 6f, and the great cardiac vein 6c. As shown, the left coronary artery 7b emerges from the aorta 9 and passes between the left atrium 2 and the pulmonary trunk 10. Alternatively, the right coronary artery 7f passes along the right atrium 3 before branching and heading down towards the ventricles. Access to one or more neural structures such as autonomic ganglia along may be made with one or more devices in accordance with the present disclosure through the walls of these vessels.

Also shown is a device 120 in accordance with the present disclosure, passing through the aorta 9 and into the left coronary artery 7b and down into the anterior intraventricular branch 7e thereof. The device 120 is coupled proximally with an operator 130, and includes an effector 125, the effector 125 including one or more sensory elements, sensing tips, delivery elements, electrodes, sensors, combination thereof, or the like in accordance with the present disclosure.

In aspects, the effector 125 may include a delivery element in accordance with the present disclosure, the delivery element configured so as to be deployable through the wall of the coronary vein in which the effector 125 is placed, so as to deliver a substance, energy, etc. to a nearby tissue, the artery wall, an adventitial space around the artery, nearby adipose tissue, functional tissues of the heart, a muscle, nearby sympathetic nerves, somatosensory nerves, a region of receptors, a diseased region of tissues, or the like.

In aspects the effector 125 may include one or more sensing elements in accordance with the present disclosure, each sensing element configured to measure a local electrophysiologic signal to assist in the localization of therapeutic targets, localize sympathetic, parasympathetic, or somatosensory nerves, assess local neural traffic, assess local smooth muscle function, assess local cardiac function, map functionality, map neural interconnectivity, assess interconnection of neural traffic, find local ganglia, apply signals, substances, form a blockage, or the like for one or more diagnostic tests, support therapy and confirm delivery of therapy, or the like. In aspects, the sensory catheter may be integrated with a therapeutic modality in accordance with the present disclosure to provide a full feedback integrated device.

Such a system may be advantageous for providing ultra-high spatial and spectral fidelity mapping of the local neural structures, and functional interface with the cardiac nerves for diagnostic, and therapeutic purposes.

Figure 2A:
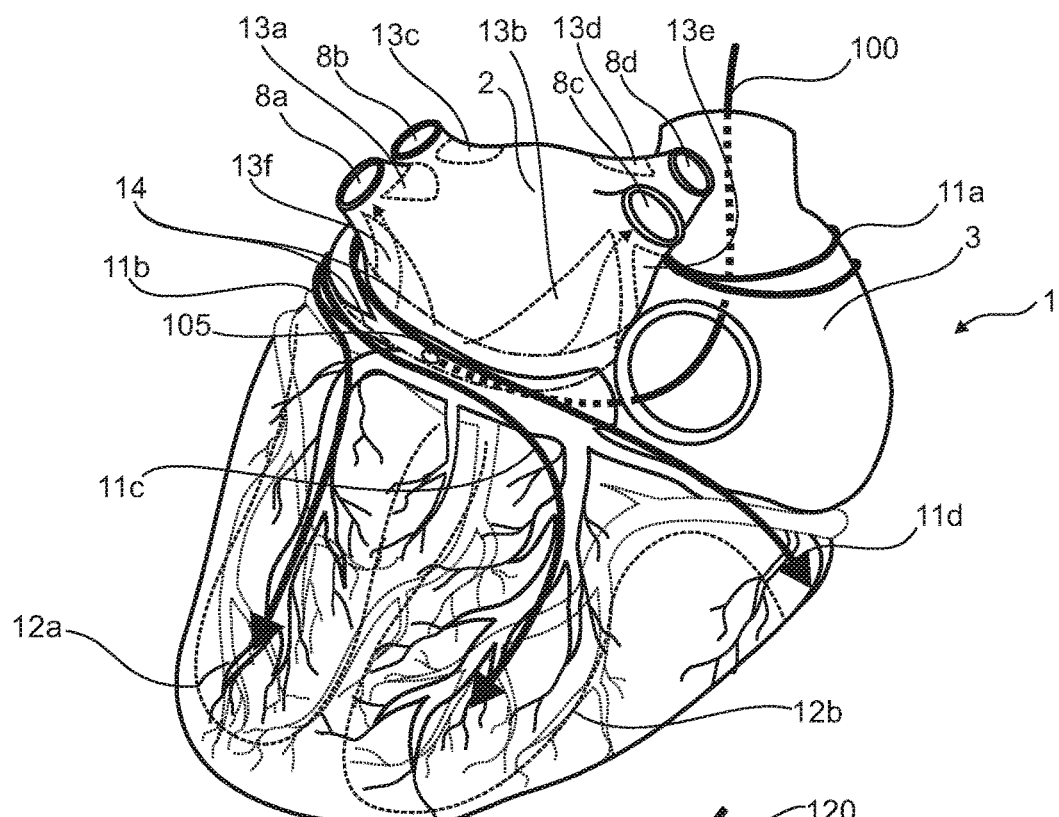
FIGS. 2a-b illustrate autonomic neural pathways overlaid on the coronary vessels and major anatomical features of a human heart.
Figure 2B:
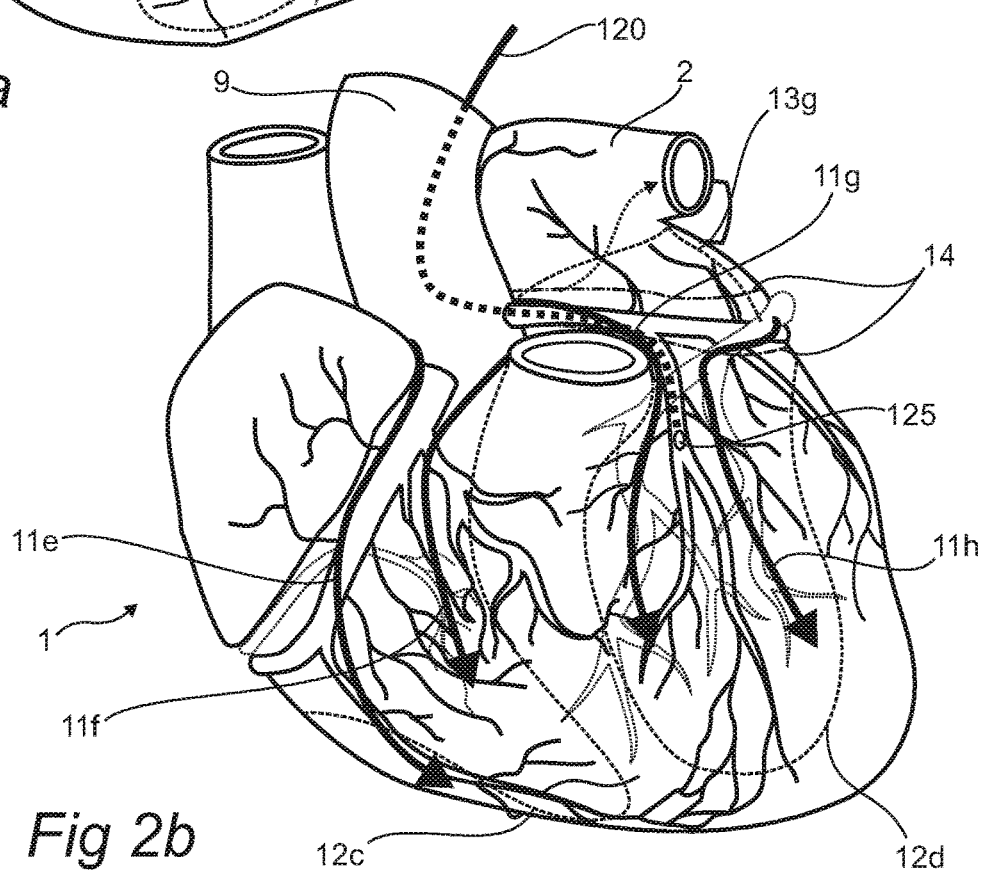

FIGS. 2a-b illustrate autonomic neural pathways overlaid on the coronary vessels and major anatomical features of a human heart 1. FIG. 2a illustrates pathways for various autonomic plexuses 11a, passing over the right ventricle 3, and other autonomic plexuses 11b-d passing along the coronary arteries and veins. The neural plexuses 11b-d generally continue along with the coronary vessels over the ventricles and spider outwards innervating the vessel walls, adipose tissue, and muscle. In aspects, access to various regions 12a,b of the autonomic innervation of the heart may be made via the corresponding coronary vessels. Networks of autonomic nerves also travel over various regions 13a-f of the left atrium 2 and to/from the pulmonary veins 8a-d.

In aspects, a method for isolating the left atrium 2 may include treating tissues in a zone 14 in the vicinity of the coronary arteries and veins traveling between the left atrium 2 and the ventricles of the heart 1. In aspects, isolation of other heart chambers may be achieved by treating tissues with a device in accordance with the present disclosure via access provided along one or more coronary arteries or veins. Such an approach may be advantageous to establish a durable left atrium 2 isolation without excessive damage or scarring to the heart tissues, or the need to dissect regions of the heart to access the target tissues, etc. In addition, one or more regions along the right/left atrium septum, along the inferior vena cava, the superior vena cava, and/or the ascending aorta may be targeted as part of such a therapy.

The device 100 shown in FIG. 2a is arranged in the coronary sinus 6a with the effector 105 positioned so as to interface with tissues of the left atrium 2, the walls of the coronary sinus 6a, or the like. The coronary sinus 6a is labeled in FIG. 1a but not labeled in FIG. 2a for clarity. In aspects, the effector 105 may include a delivery element configured so as to be oriented such that a therapeutic substance (e.g., a composition, a gel, an ablative gel, etc.) may be delivered locally into the walls of the left atrium 2 in accordance with the present disclosure. Such an approach may be advantageous to treat the tissues of the left atrium 2 while minimizing risk of damage to surrounding tissues, etc. The effector 105 may include one or more sensory elements to identify regions to be treated, monitor the treatment process, evaluate stress response of tissues, and evaluate the continuity of the treatment (e.g., gaps in the block, distance between an already treated site and the next site for treatment, etc.), a combination thereof, or the like.

FIG. 2b illustrates a anterior view of the heart 1 illustrating how various neural plexuses 11e-h pass along the aorta 9, around the coronary arteries and veins, and following the vessels down into the ventricles of the heart 1. As shown, a device 120 in accordance with the present disclosure, may be directed towards one or more target regions 12c,d of nerves via the corresponding coronary arteries, so as to perform one or more treatments in accordance with the present disclosure thereupon. As evident from FIGS. 2a-b, a range of vessels may be used by a device in accordance with the present disclosure to find diseased regions of the heart 1, assess regions of the heart 1, and to treat various regions of the heart 1 in a very spatially localized way.

In aspects, the effector 125 of the device 120 may include one or more sensory elements in accordance with the present disclosure, the sensory elements configured so as to monitor one or more electrophysiologic signals at a nearby region of the heart 1. In aspects, the sensory elements may be locally coupled with a high fidelity amplifier (i.e., arranged nearby in the body of the device 120), so as to extract one or more broadband neural signals, a region of interest, perform an ultralow noise recording of the nearby tissue, or the like. Such an approach may be advantageous to measure small neural signals, heterogeneously distributed neural signals, or the like, which may be masked by the larger myocardial action potentials, movement noise, or the like.

In aspects, the sensors or nearby amplifiers may be coupled with one or more movement artifacts, or spaced so as to help eliminate a large myocardial signal, such that the amplifier gain may be greatly increased. Further, the amplifier may be equipped with an analog to digital converter (ADC), optionally with oversampling functionality, the ADC configured so as to oversample the signal so as to further drop the noise floor thereof. In aspects, such a technique may be advantageous for dropping the noise floor more than 1 dB, more than 3 dB, more than 6 dB, more than 9 dB, more than 12 dB, or the like so as to enhance the quality of the captured signal (i.e., in circumstances wherein the signal is sufficiently small to warrant such resampling). Such an approach may be advantageous to simultaneously remove unwanted characteristics of a signal, while further dropping the noise floor so as to enhance the signal capture therefrom. In aspects, the ADC may be configured with greater than or equal to 8 bit precision, greater than or equal to 10 bit, greater than or equal to 12 bit, greater than or equal to 16 bit, or the like. The ADC may be configured with the oversampling function so as to effectively increase the precision by 1 bit, greater than 1 bit, greater than 2 bits, greater than 3 bits, or the like. Such an approach may be advantageous to reduce the size of the ADC while providing sufficiently high signal capture of neural signals in the vicinity of one or more of the sensing elements.

In aspects, the amplifier may be configured so as to amplify a broadband signal nearby a sensing element in accordance with the present disclosure. The amplifier may be configured with one or more stages, and with a pass band of greater than 1 mHz to 40 kHz, including 100 mHz-3 kHz, specifically 100 mHz-1 kHz, or the like. The amplifier may include functionality so as to be configurable in terms of gain and/or bandwidth. Thus during a measurement session, the amplifier may be first configured in a broadband mode, so as to capture as much of a signal as possible. Upon analysis of the captured signal, the amplifier may be adjusted so as to hone in on key information in the signal (e.g., such as high frequency content thereof, a movement artifact, a low bandwidth signal, so as to optimize the capture of a particular neuronal action potential train, to optimally capture a low frequency potential, to remove one or more components of a signal, etc.).

Figure 3A:
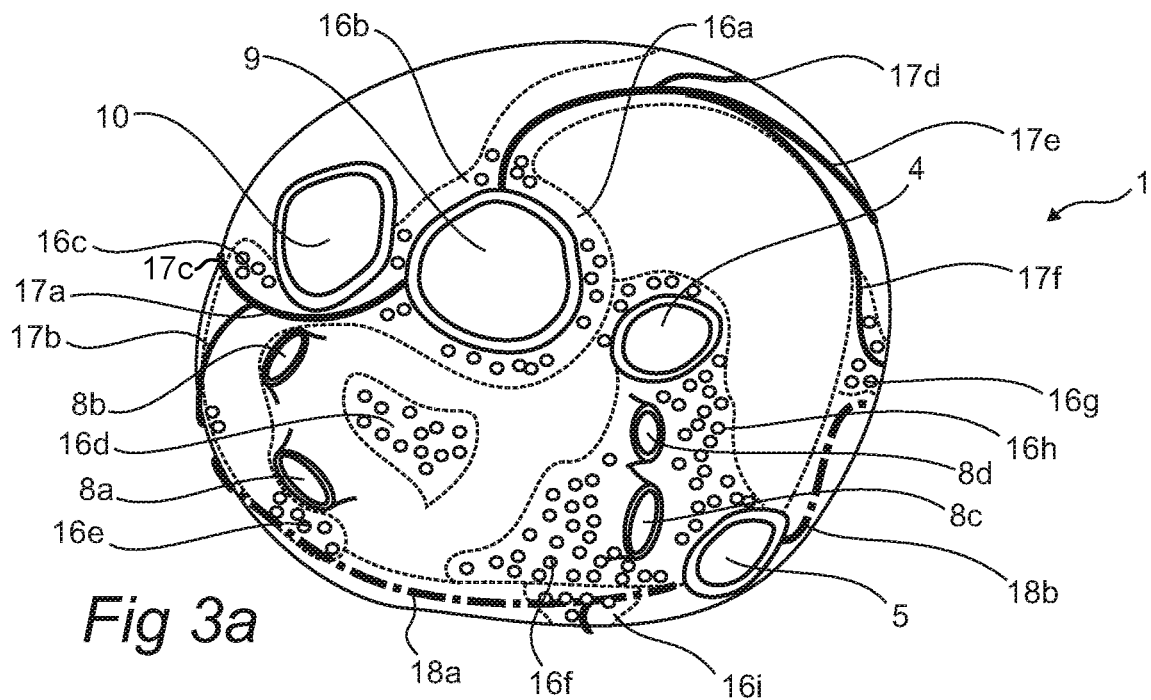
FIGS. 3a-b illustrate the approximate locations of various autonomic ganglia in relation to various coronary vessels and major anatomical features of a human heart.
Figure 3B:
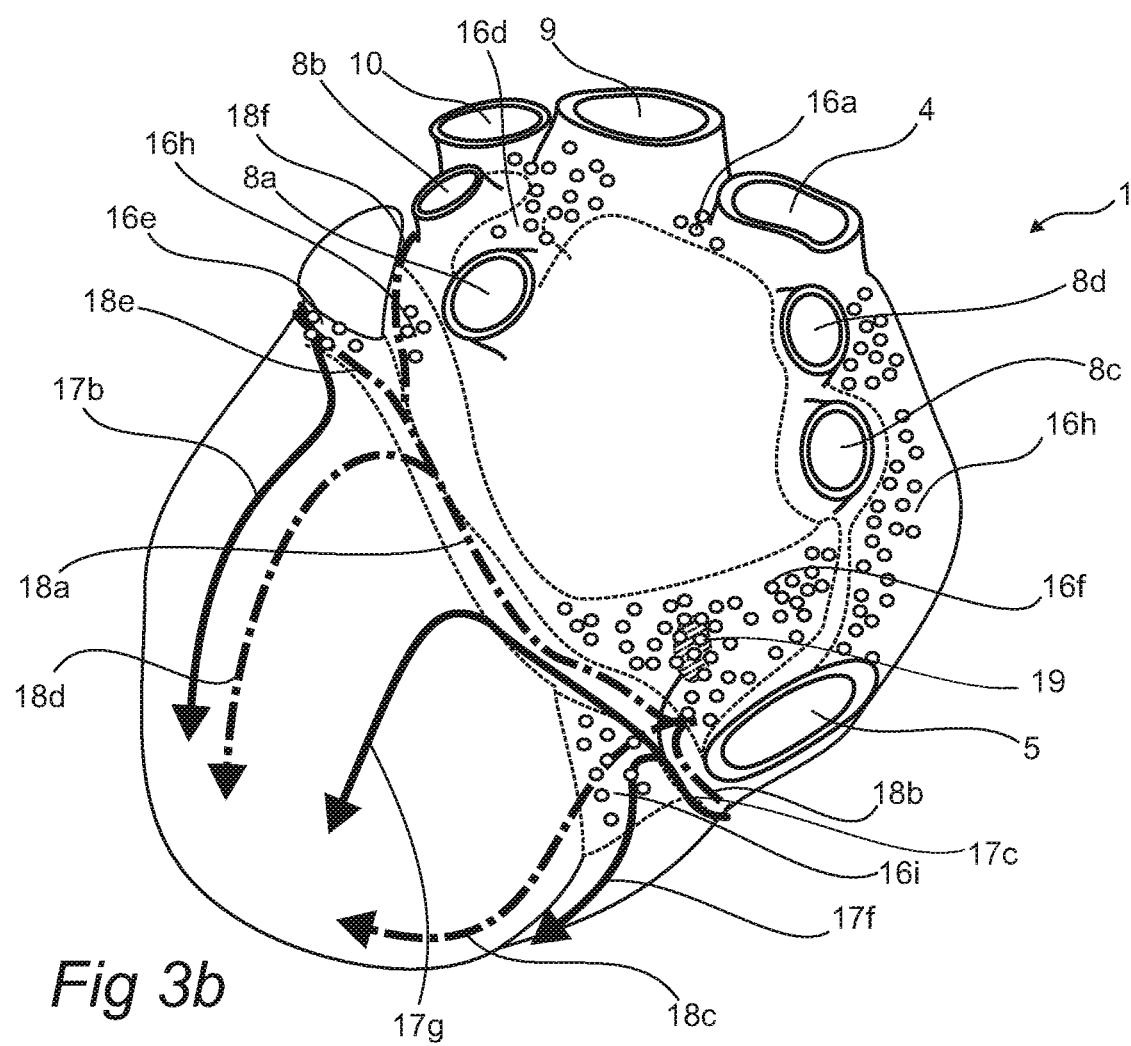

FIGS. 3a-b illustrate the approximate locations of various autonomic ganglia in relation to various coronary vessels and major anatomical features of a human heart. FIG. 3a shows a superior view of a heart 1, while FIG. 3b shows a posterior view, each illustrating a range of ganglia 16a-i arranged around the major vessels 4, 5, 8a-d, 9, 10 of the heart 1. As visible in the views, the ganglia 16a-i are generally situated around the regions around which the major vessels 4, 5, 8a-d, 9, 10 connect with the heart 1 and along the coronary arteries 17a-g and coronary veins 18a-f. Such arrangements and positioning of ganglia 16a-i are highly variable from subject to subject, and as such a sensing tool in accordance with the present disclosure may be configured to locate such ganglia, assess inter-ganglia connectivity, or the like during a procedure. In addition, a therapeutic tool, or diagnostic tool may be used to treat ganglia, to break up aberrant signal pathways, or the like alone or associated with one or more sensing elements in accordance with the present disclosure as providing procedural feedback or the like.

FIG. 3b also illustrates the location of the atrioventricular node (AV node) 19 located near the right coronary artery 17c. The sinoatrial node (SA node), not shown for clarity, is often provided with blood from the right coronary artery 17c as well but may be supplied via the circumflex branch of the left coronary artery (roughly 55% right coronary artery (RCA), 43% left coronary artery (LCA)). The AV node 19 is more often supplied by the right coronary artery (roughly 75% RCA, 25% LCA). In general, it has not been reported that such nodes are simultaneously supplied by both coronary arteries.

Figure 4:
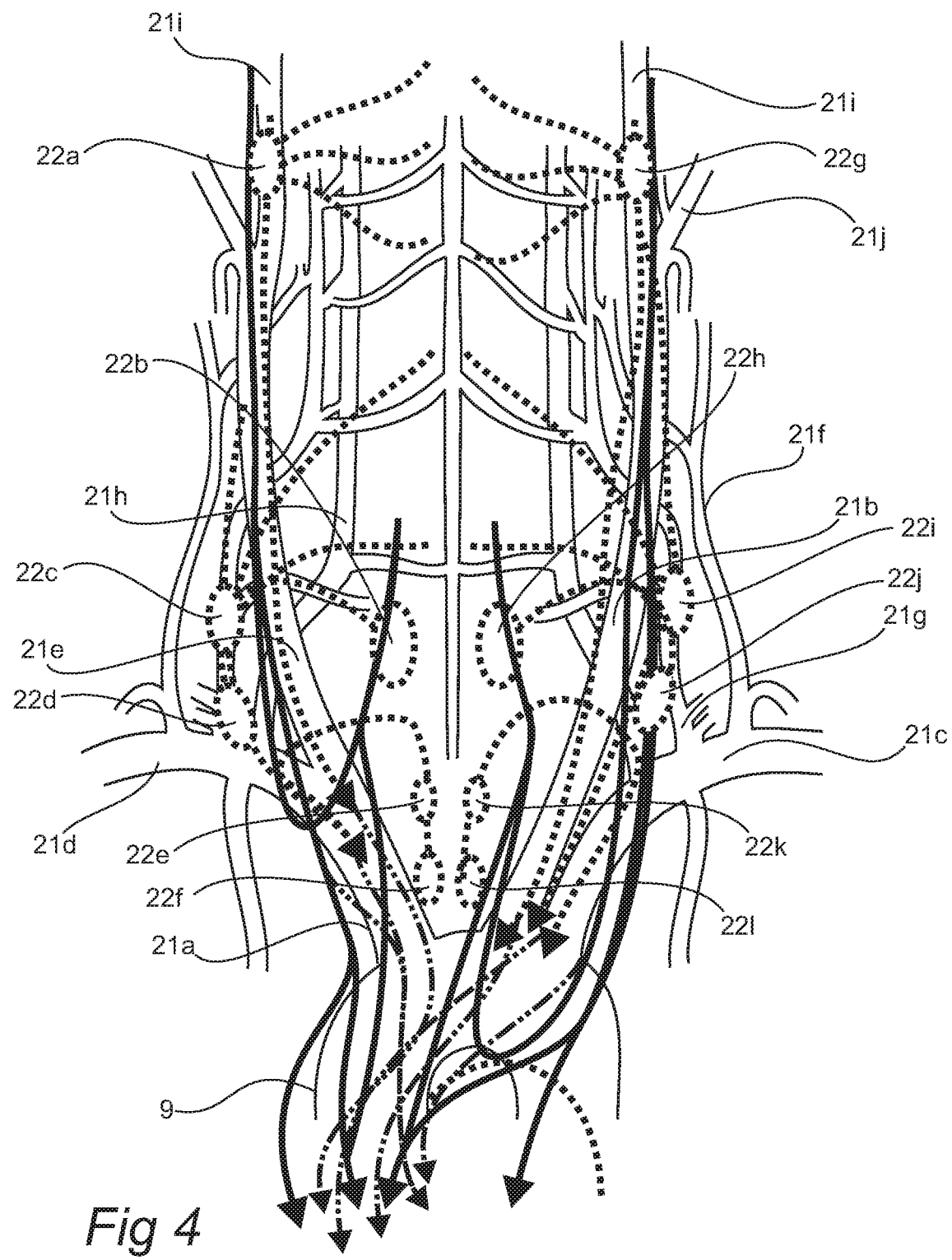
FIG. 4 illustrates the approximate positional relationships between the major arteries of the head, neck, and heart overlaid by autonomic neural plexuses innervating a human heart.

FIG. 4 illustrates the approximate positional relationships between the major arteries of the head, neck, and heart overlaid by autonomic neural plexuses innervating a human heart. The figure shows the ascending and descending aorta 9 coupled with the brachiocephalic trunk 21a, the left common carotid artery 21b, and subclavian arteries 21c, which are in turn coupled with the right subclavian artery 21d, the right common carotid artery 21e, the cervical arteries 21f, the thyroid arteries 21g, the vertebral arteries 21h, the internal carotid arteries 21i, the external carotid arteries 21j, and the like. Overlaid on the arteries are segments illustrating innervation traveling from ganglia 22a-1 and the central nervous system to the heart. Shown are plexuses primarily including parasympathetic nerve fibers (solid lines), plexuses including primarily sympathetic nerve fibers (dotted lines), and mixed plexuses (dot-dash lines). As can be seen, as the plexuses travel along the arteries to the heart, the plexuses become more mixed, such that as the plexuses travel to the heart, primarily entering along the major vessels (including the ascending and descending aorta), they are often of mixed variety.

Generally afferent and efferent fibers are collocated in plexuses. A sensing system in accordance with the present disclosure may be used to locate plexuses along one or more of the arteries shown, engage with one or more nerves or ganglia for purposes of analysis, etc. One or more therapeutic systems, delivery systems, ablation systems, or the like may be configured so as to engage with one or more nerves, plexuses, ganglia, etc. along one or more of the arteries in the head and neck, so as to treat the nerves locally, perform a block, a durable, block, or the like in accordance with the present disclosure.

As seen in FIG. 4, many of these nerves are arranged around arteries connecting the region of the aortic arch to the spine. Such pathways provide natural access to therapeutic targets, such as the carotid body one or more plexuses, etc.

Also shown are nerve plexuses entering along the ascending aorta 9. Thus a plurality of sensory catheters each in accordance with the present disclosure may be configured to map locations along the arterial walls that correspond to aberrant traffic as measured in and around the aorta 9 near the heart. Such nerves also pass along the pulmonary artery, pulmonary veins, etc.

FIGS. 5a-c illustrate the autonomic innervation into the heart and the innervation around the major vessels coupled with a human heart. FIG. 5a illustrates the basic CNS cardiac control centers and the interconnection between those centers and the heart 1. FIG. 5a shows various parasympathetic plexuses primarily extending from the medulla oblongata 23a, via the vagus nerve 24a, towards the heart 1. The preganglionic sympathetic plexuses 24d,e couple nerves in the spinal cord 23b to sympathetic ganglia 24b,c generally cervical ganglia and superior thoracic ganglia (T1-T4). Sympathetic post ganglionic plexuses 24f generally travel along with the cardiac nerve (along 24d, through 24b and 240, toward the heart 1. Shown are the superior vena cava 4, the pulmonary trunk 10, and the aorta 9 along which many of the plexuses travel as they couple to the heart 1.

FIG. 5b shows a close up illustration of various plexuses along the ascending aorta 9, the pulmonary trunk 10, and the right atrium 3, at the base of the heart 1. The plexuses 25a-e are seen traveling around and among the large vessels, down along the right coronary artery 7f, and the like. One or more methods or devices in accordance with the present disclosure may be configured to access such nerves directly and locally at these sites, for purposes of mapping, treating, ablating, etc. A ganglion 25c is shown among the neural plexuses.

FIG. 5c shows a close up of the ascending aorta 9, the left atrium 2, and the pulmonary trunk 10 illustrating the plexuses 25f-j traveling among the major vessels and into the left coronary artery 7b, and the great vein 6f. Such vessels may be ideal access points for treating target nerves in the vicinity of these locations on the heart 1. Treatment of such nerves may be performed so as to treat a range of rhythm disorders, re-route neural pathways, disconnect one or more local ganglia, isolate a ganglion, limit neuroplastic growth, perform a local sympathetic neural blockade, or the like in accordance with the present disclosure.

Figure 6:
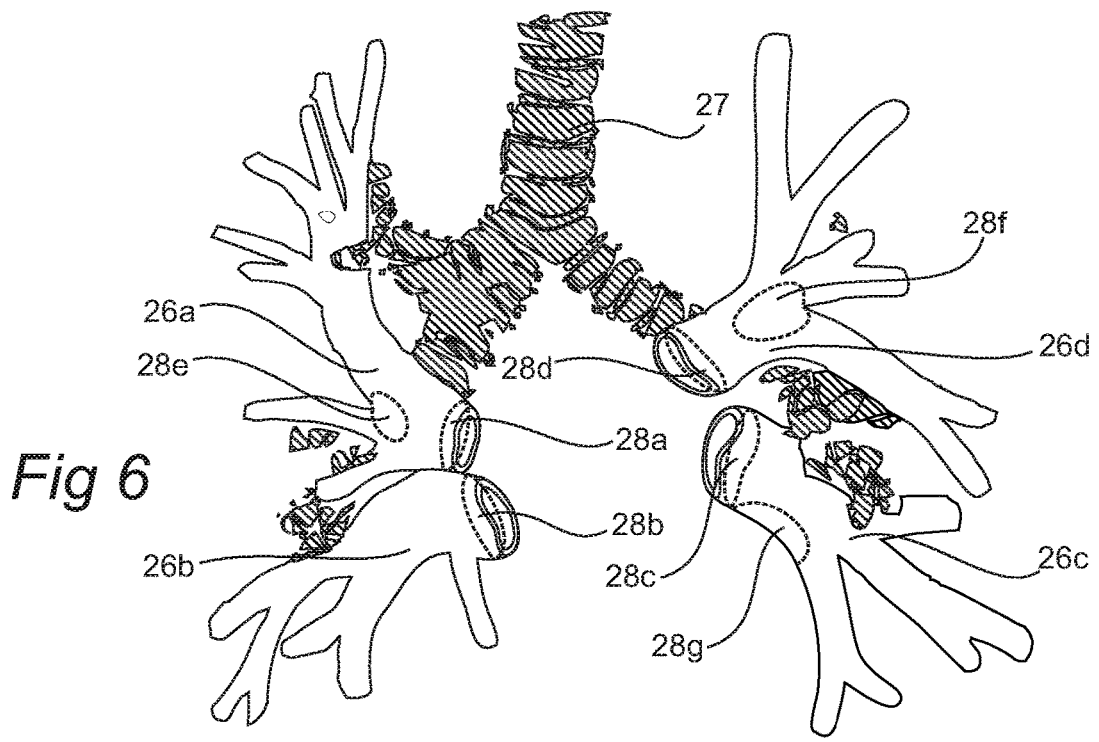
FIG. 6 illustrates regions of the pulmonary veins and target therapeutic zones.

FIG. 6 illustrates regions of the pulmonary veins and target therapeutic zones. FIG. 6 shows pulmonary veins 26a-d and the bronchial tree 27. Overlaid on the pulmonary veins 26a-d are some non-limiting examples of target treatment zones 28a-g. The treatment zones 28a-g may be the targets of a neural ablation procedure, a neural block, a parasympathetic block, a stem cell therapy, a neural growth factor therapy, or the like in accordance with the present disclosure. Such procedures may be used to regenerate damaged tissue, repair damaged tissue, isolate diseased tissues, remodel diseased tissues, perform a pulmonary vein isolation procedure, a combination thereof, or the like. A sensing system in accordance with the present disclosure may be suitable for accessing, locating, functionally evaluating, testing, coordinating therapy, confirming therapy, confirming therapy extents, confirming therapy efficacy, or the like on one or more of the target sites (or one or more alternative sites). The pulmonary veins 26a-d may be accessed via the heart (left atrium), via an external approach, or the like.

In aspects, one or more treatment zones may be out in the pulmonary vein ostium 28e-g, where a diseased tissue site, aberrant neural plexus, or positive neural feedback loop is located. Furthermore, a therapy for causing a continuous ablation for pulmonary vein isolation without excessive tissue damage, charring, necrotic tissue, or the like is present, thus allowing for treatment without as many adverse events, etc. The treatment zones 28a-d show a formed continuous ablation around the bases of the pulmonary veins 26a-d, left atrium 2 interfaces. In aspects, a high fidelity neural sensing system in accordance with the present disclosure may be used to detect the regions in need of treatment 28a-g. In aspects, an ultra-precise chemical ablation system in accordance with the present disclosure may be used to treat the regions in need of treatment 28a-g. In aspects, the high fidelity sensing system may be used to determine the extent of ablation, determine if finished, identify other targets, and monitor changes in the neural traffic flow and neural feedback after completion of an ablation/neural block, combinations thereof, or the like.

Figure 7A:
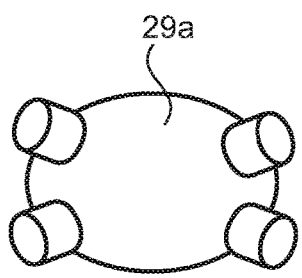
FIGS. 7a-f illustrate the human left atrium and common anatomical variations encountered in practice.
Figure 7B:
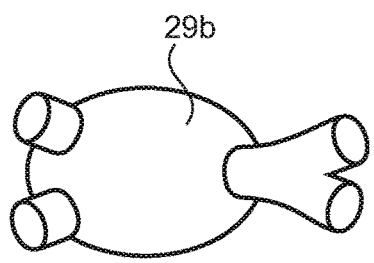
Figure 7C:
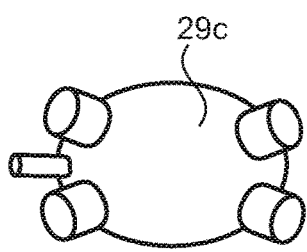
Figure 7D:
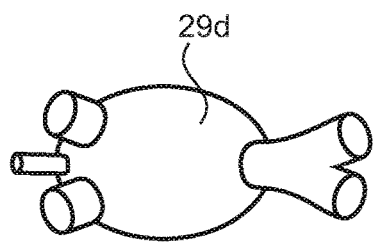
Figure 7E:
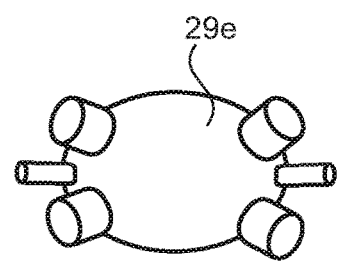
Figure 7F:
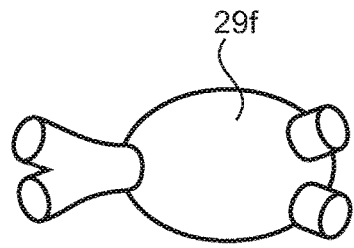

FIGS. 7a-f illustrate the human left atrium and common anatomical variations encountered in practice. A treatment may be directed to one or more sites along the left atrium wall 29a-f, along the perimeter of the left atrium, along the interface between the atrium and one or more vessels, at sites out into the vessel ostia, etc. FIG. 7a illustrates the most common human anatomical variant, while FIGS. 7b-f illustrate other common anatomical variants that may be encountered during a treatment, mapping, or diagnostic procedure in accordance with the present disclosure.

In aspects, one or more electrodes may be used to stimulate tissues during monitoring, after ablation, to test a temporary block, etc.

Figures 8A, 8B:
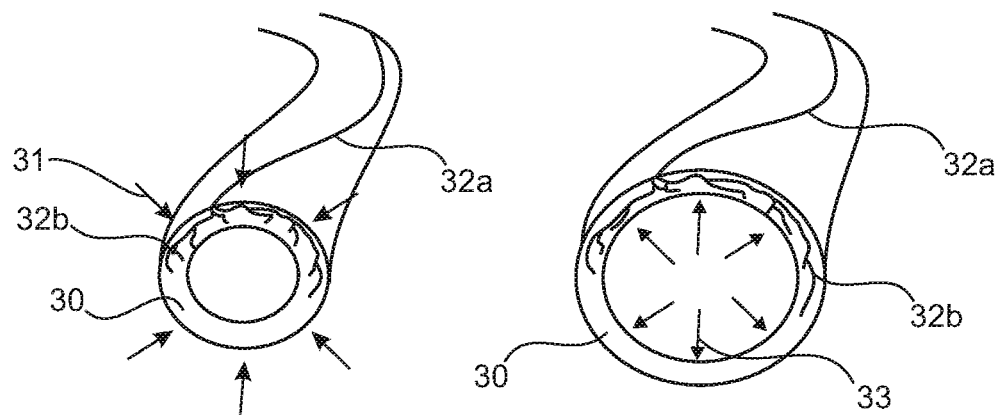
FIGS. 8a-b show a coronary vessel during contraction and dilation.

FIGS. 8a-b show a coronary vessel during contraction and dilation. FIG. 8a shows a coronary vessel 30 contracting 31 in response to neural traffic from fibers 32a,b located in the walls and surrounding adventitia thereof. Such nerves 32a,b may be directly innervating the smooth muscle of the vessel 30 directly, may interface with one or more sites in the adventitia (i.e. surrounding adipose tissue), may be related to neuroplastic changes in sensitivity, receptor quantity, etc. in the vicinity of the site, etc. FIG. 8b shows the coronary vessel 30 dilating 33 in response to neural traffic from fibers 32a,b innervating the vessel 30. In states of health, such innervation contribute to healthy tone of the coronary vessels, contraction, dilation, receptor function, sensitivity, long-term tone, and the like. In states of disease, such neural circuits may be damaged contributing to aberrant activity of the vessel (e.g., spasm, plaque growth, etc.). Monitoring and/or treatment of this traffic may allow for highly localized treatments, without the systemic side effects of pharmacologic treatment options.

Such contraction and dilation are at least partially influenced by autonomic innervation and neural traffic. Furthermore, the functional relationships between neural traffic and vessel response is complicated by inter-functional relationships between circulating hormone levels, circulating peptides, circulating neurotransmitters, and neuroplastic changes in local tissue receptor density, changes in neural ingrowth to the region, neural sprouting in response to damage, denervation caused by ischemia, neural ingrowth after ischemia, and the like. Thus a sensing system in accordance with the present disclosure may be suitable for testing the local functional relationships in a region, and determining the state of the functionality, whether a therapy is needed or not, what type of therapy will be most effective, etc. In aspects, a delivery system in accordance with the present disclosure may be used to apply a therapy to tissues in the vicinity of the coronary vessel, within the walls of the coronary vessel, along the coronary vessel, to drive neural regrowth to a vessel wall, to adjust the receptor density in the vicinity of a region of the vessel, to stop a neural sprouting process, to alter local neural growth factor levels, to denervate local tissues, to prevent restenosis of a vessel, etc.

Figure 9:
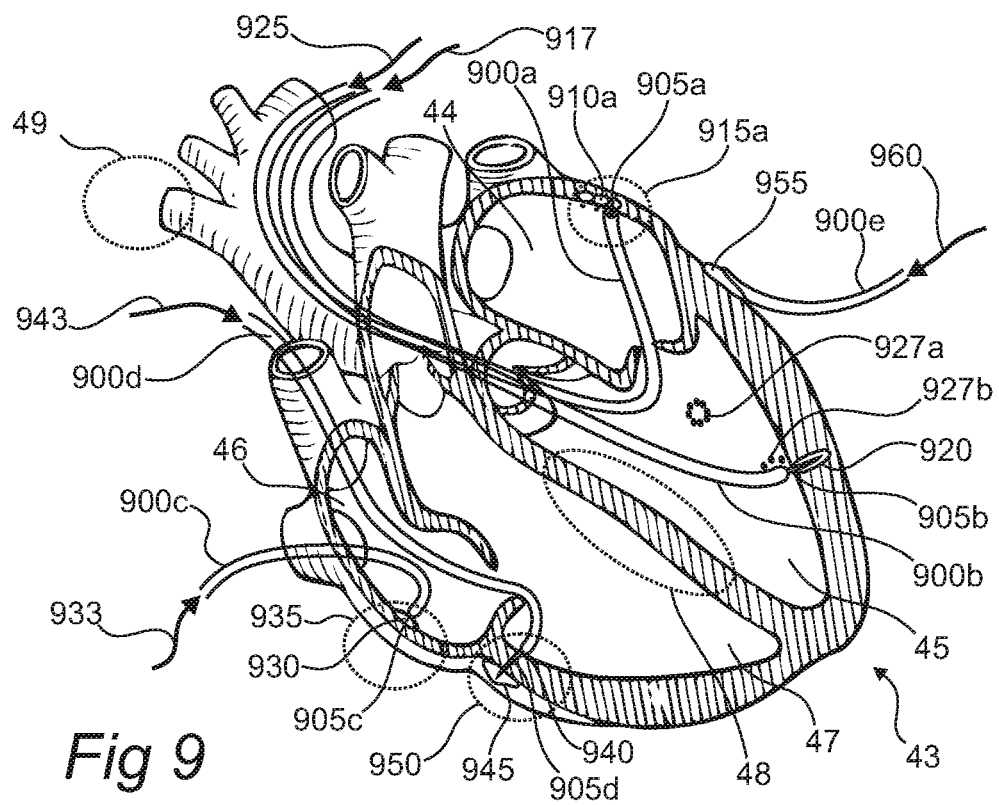
FIG. 9 illustrates internal structures of a human heart and systems and methods for accessing and treating regions thereof in accordance with the present disclosure.
Figure 22A:
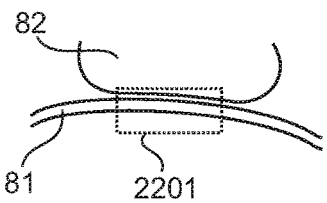
FIGS. 22a-n show aspects of a delivery system and method for treating tissues in a thin walled structure.

FIG. 9 illustrates internal structures of a human heart and systems and methods for accessing and treating regions thereof in accordance with the present disclosure. FIG. 9 illustrates a heart 43 of a subject, and the placement and interaction of delivery tools 900a-e with cardiac tissues of the heart in accordance with the present disclosure. A delivery tool 900a in accordance with the present disclosure is shown accessing the left atrium 44 of the heart 43 through the aorta, the delivery tool 900a coupled to the wall of the left atrium 44, a needle-like delivery tip 905a in accordance with the present disclosure interfacing with the wall, a plurality of boluses 910a of a composition in accordance with the present disclosure delivered 917 through the delivery tool 900a and deposited into the wall of the left atrium 44 around a desired treatment zone 915a. In aspects, the delivery tool 900a may include tissue capture means such as illustrated in FIGS. 22a-n so as to limit the treatment zone 915a to just the wall of the left atrium 44 (so as to limit collateral damage to nearby organs, to prevent perforation of the esophagus, etc.).

A delivery tool 900b is shown coupled with the wall of the left ventricle 45 of the heart 43, the delivery tool 900b including a delivery tip 905b penetrating into the wall of the left ventricle 45, a bolus 920 of a composition in accordance with the present disclosure delivered 925 through the delivery tool 900b and into the wall of the left ventricle 45 (such as forming a pattern in accordance with the present disclosure). A plurality of previously injected delivery sites 927a,b are shown in the left ventricle, demonstrating patterning of the boluses so as to treat zones of the tissue in accordance with the present disclosure. In aspects, the delivery tip 905b may be advanced into the pericardium of the heart 43 so as to treat neural structures, cardiac muscle, etc. in that region (i.e., passing from the interior of the heart through the wall and into the external tissue sites).

A delivery tool 900c in accordance with the present disclosure is shown interfacing with the right atrium 46 of the heart 43, the delivery tool 900c advanced through the inferior or superior vena cava (entering the body through the basilic vein, the femoral vein, etc.), a delivery tip 905c biased against the wall of the right atrium 46, a bolus 930 of a composition in accordance with the present disclosure having been delivered 933 to the wall, the composition dwelling against the wall so as to treat a site thereof within a treatment zone 935 along the wall.

A delivery tool 900d in accordance with the present disclosure is shown interfacing with the right ventricle 47 of the heart 43, the delivery tool 900d advanced through the inferior or superior vena cava (entering the body through the basilic vein, the femoral vein, etc.), the tip thereof biased against the wall and a delivery tip 905d advanced into the wall, such that a tip is placed near to the pericardium of the heart, so as to interact with an autonomic nerve, a pericardial site, etc. One or more sensing elements 940 (sensors, electrodes, etc.) may be incorporated into the delivery tool 900d, or delivery tip 905d, in accordance with the present disclosure, to guide the tip for delivering 943 a bolus 945, to monitor electrophysiological activity before, during, and/or after delivery of the bolus 945, to assess the margin of the bolus 945, etc. in the vicinity of a treatment zone 950.

A delivery tool 900e in accordance with the present disclosure may be delivered to the pericardial sac or space of the heart 43 (e.g., such as endoscopically, transcutaneously, during surgery, etc.). The delivery tool 900e may be aligned with a treatment site and a bolus 955 of a composition in accordance with the present disclosure may be delivered 960 thereto to treat one or more tissues sites on or near the pericardium of the heart.

In aspects, a delivery tool 900a-e in accordance with the present disclosure may be used to access one or more treatment sites along, into, or in the vicinity of the vein of Marshall, the septum 48, a carotid sinus 49, a carotid body, the posterior left atrium, the great cardiac vein, the coronary sinus, the left superior cardinal vein, the oblique vein, the venous valve of Vieussens, etc.

A delivery tool 900a-e may include a sensor, an electrode, etc. in accordance with the present disclosure to assess the effect of the treatment, to assist with guiding the delivery tool 900a-e to the neural targets (e.g., via measuring local neural traffic, via stimulation of local tissues, etc.), assist with the assessment of margins of the bolus (e.g., by assessing impedance changes around the sensors, assessing the neural, and/or epicardial traffic around the sensors, etc.).

In aspects, a delivery tool in accordance with the present disclosure may include a plurality of tips, one or more deployable tips or tip arrays, etc. so as to treat a wide swath of tissues, to rapidly form a treatment pattern, etc. in the tissues.

In aspects, a device in accordance with the present disclosure may be placed at one or more sites in the heart 43 to generate a pacing signal (one or more pacing signals, at one or more sites in the heart 43) so as to alter overall heart function, as a stress test, a method for evaluating one or more regions of the heart, to evaluate a partial inter chamber block, or the like. In aspects, a simple pacing algorithm for lowering blood pressure may include direct A-V stimulation at a very low P-R interval (e.g., around 50 msec or so, etc.). Such an approach may also be applicable to covering early premature ventricular beats, or the like.

Such an approach may be advantageous to alter local sympathetic, peripheral sympathetic, MSNA, activity, or the like. Such pacing may be advantageous for testing the response of the sympathetic nervous system to heart stress, etc. In aspects, a first pacing electrode may be placed in the right atrium and a second pacing electrode in the left ventricle. Upon pacing, an altered operational characteristic of the heart may be established, thus changing blood pressure, systolic blood pressure, pressure waveforms, etc. Such changes may have a strong influence on afferent and thus efferent sympathetic outflow, and may be useful in determining the functional activity of one or more regions of the sympathetic nervous system, determining the ideal degree of ablation needed to treat a local site in the heart, etc.

In aspects, a reference electrode may be placed in the coronary sinus for sensing and electrocardiac mapping applications. Other locations for a reference may also be used and apparent to one skilled in the art upon reading this disclosure.

Other such methods for multi-chamber pacing of the heart which may be suitable for performing stress tests, altering heart function, or the like in accordance with the present disclosure herein include, but are not limited to those methods, approaches, and devices described in U.S. Pat. No. 8,428,729 titled "Cardiac Stimulation Apparatus and Method for the Control of Hypertension," United States Patent Application Publication No. 2005/0222640 titled "Heart Muscle Stimulator and Pacing Method for Treating Hypertension," and U.S. Pat. No. 8,086,315 titled "Cardiac Stimulation Apparatus and Method for the Control of Hypertension", the disclosures of which are incorporated herein by reference.

Figure 10A:
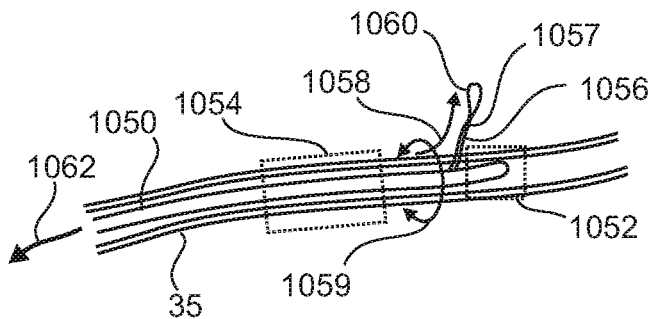
FIGS. 10a-c illustrate aspects of delivery devices in accordance with the present disclosure.
Figure 10B:
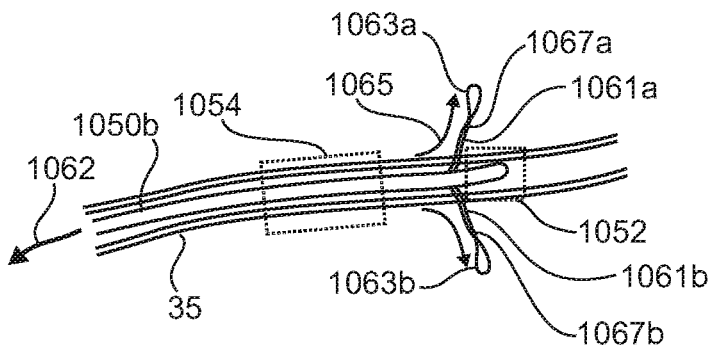
Figure 10C:
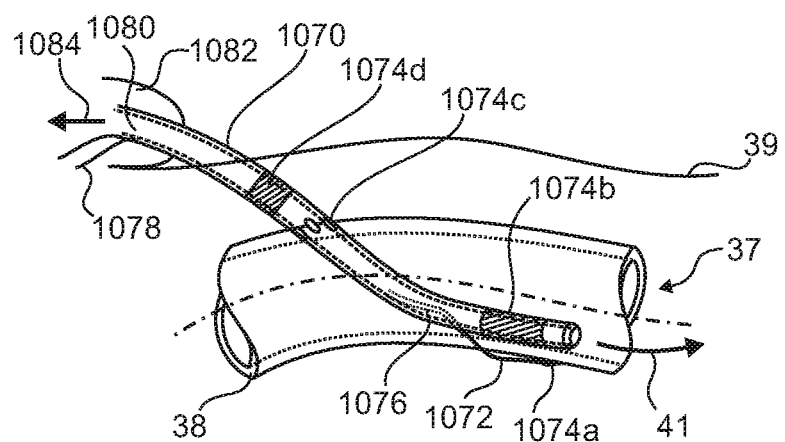

FIGS. 10a-c illustrate aspects of delivery devices in accordance with the present disclosure. FIG. 10a illustrates aspects of a guidewire 1050 in accordance with the present disclosure placed within a lumen 35. The guidewire 1050 may be sized with a sufficiently small tip diameter so as to reach a substantially small coronary vessel, with a diameter of less than 2 mm, less than 1.5 mm, less than 1 mm, less than 0.75 mm, less than 0.5 mm, less than 0.35 mm, or the like. The guidewire 1050 may include one or more zones 1054, 1052 in accordance with the present disclosure. The guidewire 1050 includes a sensing zone 1054 located along the length thereof for interfacing with the lumen wall proximally to a treatment site. The guidewire 1050 includes a sensing tip in sensing zone 1052 located at the distal tip thereof for interfacing with the lumen distally to a treatment site. The guidewire 1050 includes one or more microneedles 1056, which may be advanced from the body of the guidewire 1050 into the wall of the lumen 35 into which it has been placed as part of a procedure. Such needle advancement or retraction 1058 may be coordinated by an operator, a controller 1062, etc. In aspects, the microneedles 1056 may provide a means for delivering a chemical agent 1060 into the tissues surrounding the lumen 35. In aspects, the microneedles 1056 may include one or more electrodes 1057 to monitor and/or interface (e.g., stimulate, ablate, etc.) the local tissues upon deployment therein. In aspects, the guidewire 1050 may be configured so as to deliver the microneedles 1056 into the adventitia of the lumen 35, or optionally directly into the parenchyma of an organ to be treated. Such a configuration may be advantageous to provide a substance, a composition, a neurotoxin, a cancer treating agent, a neuroblocking agent, a neurostimulating agent, etc. into the target tissues as part of a treatment procedure in accordance with the present disclosure.

In aspects, the guidewire 1050 may be torque-able 1059 so as to orient the microneedle 1056 with respect to a target site within the wall of the vessel 35, or a nearby target tissue site. Once oriented in the desired direction, the microneedle 1056 may be deployed into the target tissue. Such an arrangement may be advantageous to treat tissues in a wall of a chamber (such as the left atrium), from within an adjacent vessel (such as a coronary artery or vein), while minimizing tissue damage thereto and limiting damage to tissues between the access vessel and the target site.

In aspects, the guidewire 1050 may include a plurality of microneedles 1056 arranged along a length thereof, the microneedles 1056 arranged to one side such that upon deployment, a linear region along the length of the lumen 35 may be treated simultaneously. Such an arrangement may also be advantageous to form a controlled wall with substantially continuous treatment zone without causing excessive damage to surrounding tissues (such as for performing an atrial isolation from a coronary vessel access point).

In aspects, one or more of the microneedles 1056 may include a stop, such that the depth of the penetration of the needle tip into the surrounding tissues may be easily controlled.

FIG. 10b shows a guidewire 1050b with similar structure to guidewire 1050. The guidewire 1050b includes a plurality of microneedles 1061a,b arranged such that multiple boluses of a substance 1063a,b may be substantially simultaneously delivered to tissues in the vicinity of the lumen (i.e. in a circumferential pattern). In aspects, the microneedles may be deploy-ably 1065 pushed through the lumen wall to access one or more target sites, to form a thin ring of treatment around the lumen 35, etc. In aspects, the microneedles 1061a,b may be fashioned with one or more sensing tips 1067a,b in accordance with the present disclosure.

FIG. 10c shows aspects of a system for monitoring electrophysiological signals in the wall 38 of a lumen 37 in accordance with the present disclosure (e.g., such as within a coronary vessel wall, through a major vessel wall, or the like). In aspects, one or more probes 1072 in accordance with the present disclosure may be embedded into a sheath introducer. The sheath introducer may include a cannula 1070, along which electrical wiring 1078 and/or one or more of the probes 1072 may be arranged. The cannula 1070 may include one or more channels 1076 to accommodate one or more of the probes 1072, electrical wiring, or the like. The cannula 1070 may include one or more electrode bands 1074b,d and/or microelectrodes 1074c, configured for measurement within the wall 38 of the lumen 37, and/or for use as reference electrodes. The sheath introducer may include an embedded circuit and/or connector for interfacing with one or more of the electrodes 1074a-d, probes 1072, etc.

In aspects, one or more of the probes 1072 may include one or more electrodes 1074a in accordance with the present disclosure.

In aspects, one or more probes 1072 may be inserted into the lumen 37 of the subject, one or more of the probes 1072 may be inserted into the wall 38 of the lumen. In aspects, one or more of the probes 1072 may be anchored to the lumen wall 38, and/or one or more readings may be made from an electrode 1074a situated on the probe 1072 and/or on the cannula 1070 of the sheath introducer, to assist with placement, to read electrophysiological activity from the wall 38 of the lumen (i.e. to read activity within the smooth muscle of the media of the lumen wall), etc.

As part of a surgical procedure, the sheath introducer may be placed into the lumen 37 of a vessel through a skin 39 of a subject. The sheath introducer may provide a path for additional surgical tools to be introduced into the lumen 37 and progressed 41 there along to a target site (optionally remotely positioned from the entry point into the lumen). In aspects, one or more surgical tools (guidewires, catheters, balloon catheters, ablation catheters, etc.) may be introduced into the lumen 37 of the vessel via the sheath introducer.

In aspects, the sheath introducer may include a housing 1082 for placement against the skin 39 of the subject. The housing 1082 may include a valve coupling 1084 connected to the channel 1080 within the cannula 1070 of the sheath introducer, through which one or more tools may be advanced, removed, or exchanged during a surgical procedure. In aspects, the housing 1082 may include one or more connectors for interfacing electrically and/or mechanically with one or more of the electrical wiring 1078, electrodes 1074a-d, the probe 1072, or the like. In aspects, the connector may include an actuation mechanism (e.g., a sliding mechanism, a rotary mechanism, etc.), movement of which may be used to deploy the probe 1072 from within the channel 1076 into the lumen wall 38.

Such a configuration may be advantageous for use during a surgical procedure, to monitor electrophysiological activity from the vessel, for monitoring of smooth muscle activity before, during, and/or after the procedure, etc. Such a configuration may be advantageous for conveniently monitoring such activity while providing an access port for one or more of the surgical tools introduced during the procedure.

FIGS. 11a-i illustrate aspects of sensing devices in accordance with the present disclosure. FIGS. 11a-i show aspects of sensing tips, and/or zones associated with a sensing guidewire in accordance with the present disclosure. Generally speaking, the figures show non-limiting examples of sensing guidewires each including one or more sensors or electrodes located at the distal tip thereof. In aspects, the electrodes may be arranged in patterns around the circumference of the tip so as to contact a lumen wall if the guidewire is introduced deep enough into the lumen so as to bottom out (i.e., as the lumen diameter shrinks distally heading into the organ). The electrodes may be connected to a controller, a preamp (optionally embedded in the guidewire near the electrodes), a microcircuit (optionally embedded in the guidewire near the electrodes), a connector, or the like in accordance with the present disclosure. Such interconnection may be provided by one or more lead wires arranged along the length of the guidewire. In aspects, one or more of the lead wires may be integrated into the walls or jacket of the guidewire. In such configurations, the lead wires may be helically integrated, and/or braided into the walls or jacket, or equivalently threaded, coextruded, plated, shrink wrapped, or pultruded within the walls of the guidewire (or equivalently threaded through one or more microlumen within the wall of the guidewire).

The electrodes may be formed in accordance with the present disclosure. In aspects, the electrodes may be formed directly from the tips of the one or more lead wires. The tips of the lead wires may be formed into microelectrode elements, with predetermined exposed areas and tip profiles, suitable for monitoring electrophysiological activity at the site of interest. In aspects, the predetermined exposed areas may be designed so as to lean towards single unit recordings (e.g., electrode area less than 250 $\mu m^2$, less than 150 $\mu m^2$, less than 100 $\mu m^2$), multi-unit recordings (e.g., electrode area of greater than 500 $\mu m^2$, greater than 1000 $\mu m^2$, greater than 2000 $\mu m^2$), and large area or reference field recordings (e.g., electrode area greater than 10,000 $\mu m^2$, or the like). In aspects, the electrodes may be treated so as to alter the impedance thereof during use. In aspects, the electrodes may be processed so as to increase the capacity thereof such as via conversion to, plating of, or augmentation with an electric energy storage (EES) material, an intercalating material, surface area increasing process, a plating process, combinations thereof, or the like. In aspects, each electrode may be configured with a profile suited for accessing the anatomy of interest (e.g., a needle-like structure, an embossed structure, a whisker like structure, a dendritic structure, etc.).

FIG. 11a shows aspects of a sensing tip of a guidewire 1126 in accordance with the present disclosure. The guidewire 1126 includes a microbasket electrode array 1128 including an array of microfingers 1129, each arranged in a bowed shape so as to extend out from the axis of the lumen into which the device is placed. Aspects of a single microfinger 1129 in the array is shown in the detailed view A. The microfinger 1129 includes one or more sensors or electrodes 1129a, each in accordance with the present disclosure. In the example shown in FIG. 11a, the electrode 1129a is shown patterned so as to face radially outwards from the center of the lumen into which the sensing tip is deployed (so as to embed and optionally isolate the electrode 1129a from the blood upon deployment). The electrode 1129a may be formed in accordance with the present disclosure. One or more regions of the microfinger 1129 may be isolated from the surroundings with an insulating layer (e.g., a passivated layer, a dielectric layer, a polymer, PTFE, parylene, etc.). In aspects, the microfinger 1129 may be configured so as to deploy to reach the shape shown in FIG. 11a during a predetermined procedure (e.g., actuation, sheath retraction, core extension, biodegradation of a restraint, etc.). In aspects, the microbasket electrode array 1128 may be deployed during use so as to interface with the walls of a lumen, in accordance with the present disclosure. One or more microfingers 1129 and/or sensors or electrodes 1129a may be coupled with a connector or a controller 1127, preamp, microcircuit, circuit, a connector, or the like each in accordance with the present disclosure.

FIG. 11b shows aspects of flexible multi-electrode guidewire tips 1121, 1101 in accordance with the present disclosure. FIG. 11b shows monolithic guidewire tips 1101 including one or more tines 1103, each tine including one or more sensors and/or microelectrodes 1105 each in accordance with the present disclosure configured for interfacing with an anatomical site of interest within a body. The guidewire tip 1101 may be at least partially formed or coupled to a flexible substrate in accordance with the present disclosure configured and dimensioned to interface with the tines 1103 as well as provide electrical interconnection of components placed there upon, or integrated into the substrate.

In aspects, the substrate may include a flexible polymer, polyimide, PET, PEN, an elastic material, a silicone, an elastomer, an electroactive polymer, or the like known in the field of flexible electronics.

In aspects, the guidewire tip 1101 may include one or more microcircuits in accordance with the present disclosure. The microcircuits may be configured to perform one or more functions such as signal routing, multiplexing, demultiplexing, preamplification, signal amplification, filtering processes, differential coupling to a reference electrode, signal conditioning function, analog to digital conversion, communication, power management, combinations thereof, and the like. The substrate may include one or more conducting traces placed so as to interconnect the sensors and/or electrodes with the microcircuits. In aspects, the microcircuit may have a width of less than 2 mm, less than 1.5 mm, less than 1.1 mm, less than 1 mm, less than 0.75 mm, less than 0.5 mm, less than 0.36 mm, or the like. In aspects, a plurality of microcircuits may be embedded into the guidewire tip 1101 so as to interface with a large number of electrodes 1105, etc.

In aspects, the substrate may include one or more of the conducting traces, the conducting traces may include a metal, a meandering metal trace (i.e., so as to improve the flexibility or stretch capability thereof), an organic conductor, a printed structure, a physically deposited structure, or the like.

In aspects, one or more microelectrodes 1105 may be formed at the extreme tip of a tine 1103. Such formation may be achieved by routing one or more traces to the tip and severing the tip so as to expose only the most distal part of the trace so as to form the interconnect for the microelectrode 1105. The interconnect may be plated with an interfacing material, such as a metal, platinum, a composite, a conjugated polymer, etc. so as to form the microelectrode 1105 and so as to enhance coupling between the microelectrode 1105 and a surrounding anatomical site of interest.

The substrate may include interconnects for coupling with power and signal lead wires. The microcircuit may be configured to communicate with an outside communication module, a controller, or the like (not explicitly shown). In aspects, communication may be in the form of a bus protocol such as I$^2$C, 1-wire, SPI, serial, etc. In aspects, the lead wires may be configured and interconnected to power management hardware configured so as to provide power and signal communication along the same leads. Such a configuration may be advantageous to minimize the number of lead wires within the guidewire.

After attachment of components (e.g., sensors, microcircuit(s), lead wires, etc.) the substrate may be rolled to form a completed guidewire tip. A non-limiting example includes a guidewire tip with an integrated jacket coupled to the tip so as to reinforce the electrical interconnection of the substrate, the lead wires, and/or the microcircuits. In aspects, the jacket may also provide increased electrical isolation between the microcircuits, the traces, the lead wire interconnects, and the surroundings.

FIG. 11b illustrates a non-limiting example of a guidewire tip 1121 with deployable tines 1103. The tines 1103 may be deployed from within a jacket 1123 by retraction 1127 of the jacket 1123, advancement 1125 of the tines 1103 or a combination thereof. Such action will lead to deployment 1115 of the tines 1103 so as to monitor a physiologic parameter during a procedure in accordance with the present disclosure.

Two non-limiting examples of deployed configurations are shown in FIG. 11b, a configuration where the tips of the tines 1103 are free and the set shape of the tines 1103 results in a flower like formation upon deployment from the jacket 1123. In aspects, the interconnects 1131 on the substrate 1107 may be dimensioned and/or encapsulated so as to form a soft seal against the jacket 1123. Such a configuration may be advantageous to minimize fluid ingress to the guidewire during a procedure.

In aspects, the lead wires 1131 may be coupled with a controller 1130 in accordance with the present disclosure.

Another example of a deployed configuration is shown in FIG. 11b, a configuration where the tips of the tines 1103 are held together with a restraining tip 1135 so as to form a basket shape upon deployment 1125. The basket may be retained in a jacket 1139 of the device before deployment 1125. In aspects, the restraining tip 1135 may include an additional pull wire 1132 configured such that relative movement of the pull wire may provide the forces necessary to deploy 1125 the tines 1103 (i.e., to convert the tines 1103 from a collapsed shape to a basket-like shape).

In aspects, one or more of the tines 1103 may be coupled with a microcircuit 1137 in accordance with the present disclosure. The microcircuit 1137 may be embedded into the device substantially near to the tines 1103, within 400 mm thereof, 100 mm thereof, within 20 mm thereof, within 5 mm thereof, etc.

FIG. 11c shows a guidewire 1140 in accordance with the present disclosure. The guidewire 1140 includes a tip for interfacing with target tissues in a vessel, the tip including a cage 1143, the cage including a plurality of electrodes 1144 coupled to an embedded microcircuit 1147 in accordance with the present disclosure via substrate 1145. The guidewire 1140 includes a bridge 1148 coupled with the microcircuit 1147 and a controller 1150, so as to provide proximal communication between the microcircuit 1147 and external hardware of the controller 1150 during use. The guidewire 1140 also includes an optional thin flexibility adjusting sheath 1149 configured so as to adjust the stiffness of the bridge 1148 (e.g., so as to adjust the push ability of the tip, allow for deployment of a spiral based ablation catheter over the bridge 1148 during use, etc.). The guidewire 1140 further includes a guide tip 1141 coupled with the cage 1143 via a guide ring 1142, the guide ring 1142 optionally connected or slidingly coupled to the guide tip 1141 so as to allow for diameter adjustment of the cage 1143 during use. Such an arrangement may be advantageous for engaging the electrodes 1144 of the guidewire 1140 with the walls of a small vessel, threading the cage 1143 through a tortuous vessel, or the like. In aspects, such a catheter may be suitable for accessing a coronary vessel, coronary artery, coronary vein, artery, vein, or the like in a subject in accordance with the present disclosure. The deployed cage 1143 diameter may be generally in the range of 0.5-8 mm, particularly 0.5-2 mm, including 0.5-1.5 mm, or the like.

FIGS. 11d-f illustrate a non-limiting example of a guidewire 1160 in accordance with the present disclosure illustrating floating cage 1163 embodiment. The floating cage 1163 includes one or more sensory elements, sensors, electrodes, etc. in accordance with the present disclosure. The floating cage 1163 is coupled with a guide ring 1162 and an electronics housing 1165 which are both configured so as to slidingly engage with a guide tip 1161. The guide tip 1161 is fastened to one or more stops 1166a,b, which define a range 1173, 1174 over which the floating cage 1163 may travel during pull back 1172 or push forward 1175 operations of the bridge 1169. In this non-limiting example, the guidewire 1160 includes a coupling 1171 arranged so as to physically and electrically attach the bridge 1169 to an embedded microelectronic circuit 1167 via flexible interconnect 1168. The arrangement may be advantageous to minimize wall stress against the deployed floating cage 1163 during movement along an associated vessel wall. Such an arrangement is suitable for ensuring that the cage 1163 is always in a self-reducing arrangement during such movements (i.e., so as to limit wall stresses during advancement 1175 or withdrawal 1172 of the cage during use). FIG. 11e shows the guidewire 1160 during pullback 1172, and FIG. 11f shows the guidewire 1160 during advancement 1175 along a lumen axis.

FIGS. 11g-i illustrate a non-limiting example of a guidewire 1180 in accordance with the present disclosure illustrating floating cage 1183 embodiment. The floating cage 1183 includes one or more sensory elements, sensors, electrodes, etc. in accordance with the present disclosure. The floating cage 1183 is coupled with two guide rings 1182 and 1191 both configured so as to slidingly engage with a guide tip 1181. One of the rings is arranged so as to be electrically coupled to one or more sensing elements in the cage 1183 with an associated electronics housing 1185 via a flexible interconnect 1188, the electronics housing 1185 coupled with the guide tip 1181 and associated bridge 1189 so as to communicate with an externally located controller. The arrangement allows for the cage 1183 to float along the guide tip 1181 during pull back 1192 or push forward 1195 operations of the bridge 1189. During such movements, the limits of the cage 1183 movement are generally determined by the size and positioning of the electronics housing 1185. In this non-limiting example, the electronics housing 1185 is arranged so as to physically and electrically attach the bridge 1189 to an embedded microelectronic circuit 1187 embedded there within. The arrangement may be advantageous to minimize wall stress against the deployed floating cage 1183 during movement along an associated vessel wall. Such an arrangement is suitable for ensuring that the cage 1183 is always in a self-reducing arrangement during such movements (i.e., so as to limit wall stresses during advancement 1195 or withdrawal 1192 of the cage during use). FIG. 11h shows the guidewire 1180 during pullback 1192, the cage 1183 movement limited 1193 during the maneuver, and FIG. 11i shows the guidewire 1180 during advancement 1195, the cage 1183 movement limited 1194 during the maneuver, along a lumen axis.

The structures shown in FIGS. 11a-i may be used for in vessel and through vessel sensing, for chemical delivery, etc. in some embodiments. The structures shown in FIGS. 11a-i may be used, for example, in neural sensing along arteries, coronary arteries, veins, coronary veins, etc.

Figure 12A:
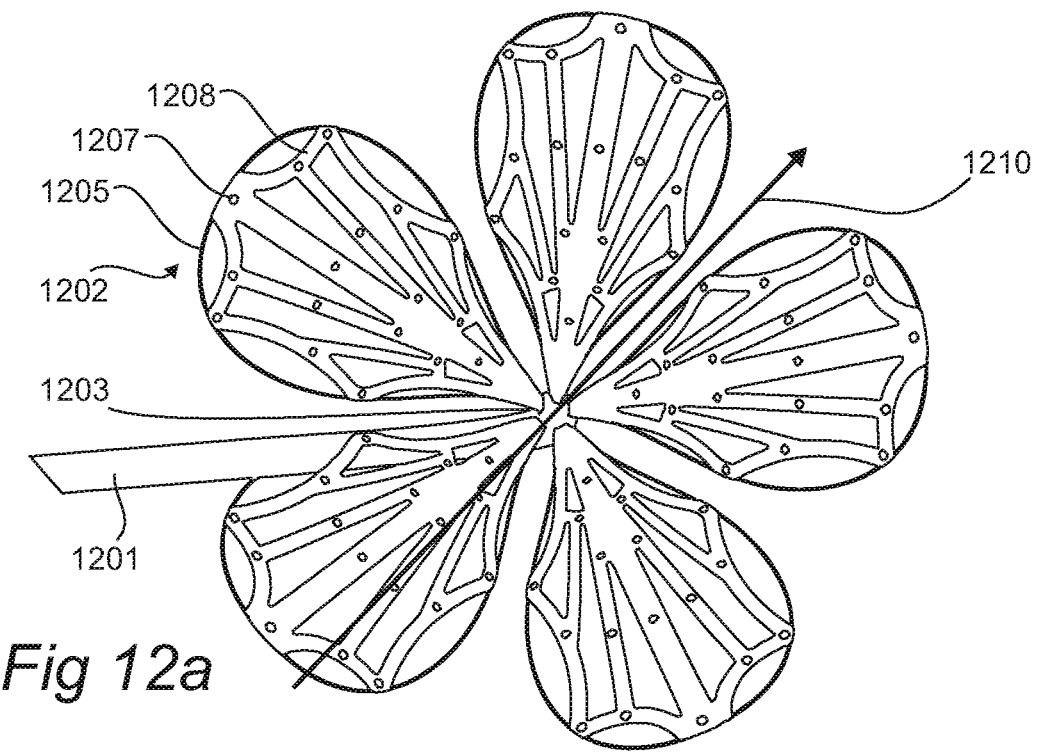
FIGS. 12a-b illustrate aspects of sensing devices in accordance with the present disclosure.
Figure 12B:
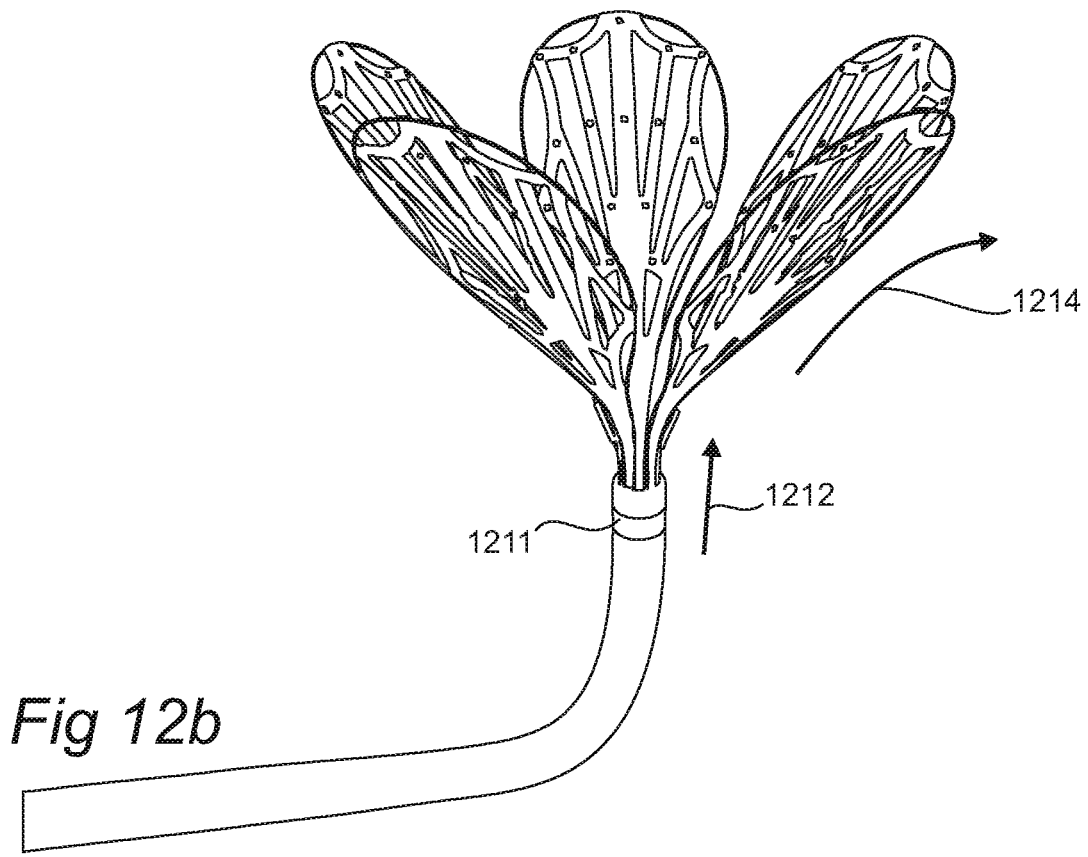

FIGS. 12a-b illustrate aspects of sensing devices in accordance with the present disclosure. FIG. 12a shows a view of a pedal based sensing device 1201 with the pedals 1202 deployed (such as against the wall of a large vessel, against a chamber wall of a heart, etc.). Each pedal 1202 is configured so as to softly and confidently bias against the wall of a target region upon deployment from a body 1203 of the catheter 1201. The pedals 1202 may be arranged so as to bias one or more sensing elements, electrodes 1207, or the like against the lumen wall during deployment 1214. As shown, each pedal 1202 includes a framing band 1205 (in this non-limiting example formed from a flexible wire element), and a substrate 1208 webbed around the framing band 1205 so as to form a surface upon which a plurality of sensors 1207 are arranged. In aspects, the substrate 1208 may be formed from a flexible material, a polymer, a liquid crystal polymer, a non-woven, a mesh, a woven wire arrangement, etc. In aspects, the substrate 1208 is formed from a non-woven, the electrodes 1207 connected with a proximally embedded microcircuit in accordance with the present disclosure, via micro wires embedded in the substrate 1208 (not explicitly shown for clarity). In aspects, each pedal 1202 may include a microcircuit coupled with the corresponding substrate 1208. Thus the catheter 1201 may include a plurality of microcircuits so as to manage a large number of sensing elements, electrodes 1207, etc. In this non-limiting example, each pedal 1202 is equipped with 17 electrodes 1207, thus the 5 pedals 1202 include 85 electrodes 1207 to generate an ultra high density spatially distributed sensing region defined by the boundary 1210 of the deployed pedals 1202. In aspects, the boundary 1210 diameter may be adjusted by altering the deployment depth 1212 of the pedals 1202, altering the length of the pedals 1202, etc. In aspects, the number of electrodes per petal may be considerably higher than shown in the Figure. In aspects, one or more of the electrodes in each petal may be configured as reference electrodes.

By embedding the microcircuits locally to the recording site, a seemingly limitless number of electrodes may be incorporated into the catheter tip. In one non-limiting example, each petal or equivalent electrode supporting structure may include tens to hundreds of electrodes (i.e. greater than 10 electrodes, greater than 15 electrodes, greater than 63 electrodes, greater 127 electrodes, etc.), so as to obtain exquisite spatial acuity during mapping, sensory recording, characterization of a rotor, of a neural or cardiac ablation target, mapping of changes in electrical activity during an ablation event, etc.

FIG. 12b illustrates how the pedals 1202 may be flexibly biased 1214 against a lumen wall during deployment 1212. Thus the electrodes 1207 may be controllably maintained against the lumen wall during use, thus improving the quality of the recordings derived therefrom, reducing movement noise artifacts, etc. FIG. 12b also shows a markerband 1211, which may be used to assist with positioning of the catheter in the subject. In aspects, the markerband 1211 may double as a reference electrode for one or more electrodes coupled to the catheter.

In some embodiments, the pedals 1202 shown in FIGS. 12a-b are used to interface with walls or other end-on surfaces such as the ventricles and atria of a heart from within the chamber, or on the outside of the heart.

Figure 13A:
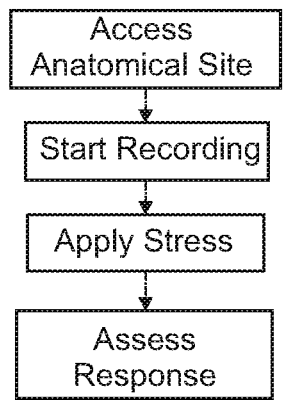
FIGS. 13a-c illustrate methods for sensing neural traffic and treating tissues in accordance with the present disclosure.
Figure 13B:
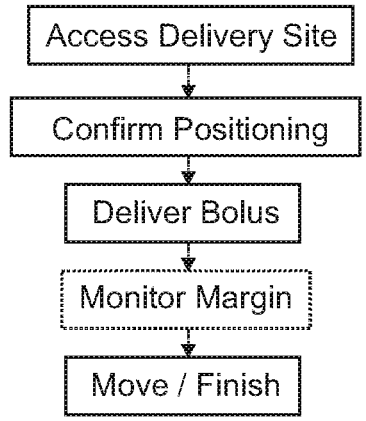
Figure 13C:
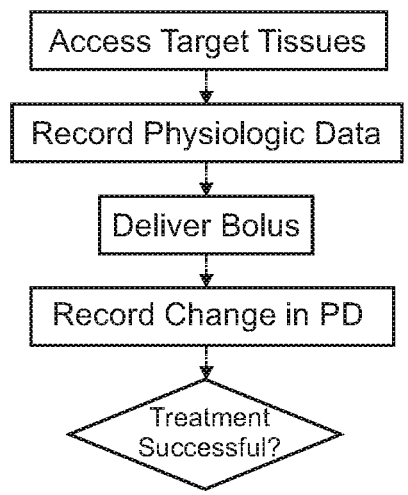

FIGS. 13a-c shows aspects of methods in accordance with the present disclosure. FIGS. 13a-c shows aspects of methods for using a delivery system in accordance with the present disclosure. The method of FIG. 13a includes accessing an anatomical site, starting recording of signals, applying a stress and assessing the response. The method of FIG. 13b includes accessing a delivery site, confirming positioning, delivering a bolus, monitoring margin, and moving the delivery system or finishing the method. The method of FIG. 13c includes accessing target tissues, recording physiologic data (PD), delivering a bolus, recording changes in PD and determining if a treatment is successful. Although the methods of FIGS. 13a-c include aspects for assessing response, monitoring margin, confirming treatment, etc. they may be applied to treatment scenarios without substantial feedback steps.

The method of FIG. 13b includes accessing a delivery site within a body, such as the parenchyma of an organ, a site along or through a vessel wall, or the like. By accessing the delivery site is meant coupling a tip or region of a delivery tool in accordance with the present disclosure with one or more anatomical sites within the body, so as to provide fluid communication between a reservoir and the anatomical sites for which treatment is desired. Such access may include delivery of a tool tip to a desired treatment site, deployment of one or more delivery needles towards the desired treatment site, to penetrate the wall of a lumen to access the treatment site, etc.

The method of FIG. 13b may optionally include confirming placement near the anatomical site, such as by recording physiologic activity from tissues in the vicinity thereof (e.g., with a sensor or electrode, a guidewire, a delivery tool, etc. each in accordance with the present disclosure), and monitoring a trend in the physiologic signal (e.g., during a stimulation event, during a stress test, etc.), making a diagnosis or prognosis based upon the recorded signal (e.g., a diagnosis of a disease state associated with local physiologic activity in the tissues, making a prognosis relating to an outcome of a disease state associated with activity in the tissues or tissues associated therewith, etc.), via direct imaging of the tissues with an imaging system in accordance with the present disclosure, etc. The method of FIG. 13b may include delivering a bolus of a composition in accordance with the present disclosure to the tissues, in the form of a pattern, etc. The method of FIG. 13b may include optionally monitoring the margin of a tissue target near the delivery site, and/or monitor the migration of the composition or a component thereof upon delivery to the tissues. The method of FIG. 13b may include moving the delivery tool, retracting a delivery needle, or otherwise finishing the treatment by decoupling the delivery tool from the treatment site.

In aspects, the method may include one or more additional steps in accordance with the present disclosure. In aspects, the method may include placing an additional tool including one or more sensors and/or electrodes at a remote location (with respect to the organ) in the body and stimulating the local anatomy at either the remote site or within the parenchyma of the organ and monitoring an evoked response within the target tissues or at the remote site respectively. Such a configuration may be advantageous for elucidating information about the connectivity between the two sites (i.e., relevant to determining if a neuromodulation procedure applied there between has been successful, etc.).

FIG. 13c illustrates an additional method including accessing the target tissues (alternatively an anatomical site of interest, a vessel, an artery, a vein, an arteriole, a venule, etc.), and recording and/or mapping the electrophysiological activity in the vicinity of the anatomical site of interest. The mapping may be provided by sweeping a sensory tip in accordance with the present disclosure over the anatomical site of interest, inserting and then withdrawing the sensory tip, deploying the sensory tip and then dragging and/or rotating the deployed tip along/around the lumen wall, combinations thereof, and the like. In aspects, the method may include displaying the mapped physiologic information for a user, constructing an anatomical model therefrom, directing a surgical robot to perform a treatment therefrom, comparing the map with a previously determined map (e.g., as a means for monitoring the outcome of a procedure, tracking a therapy, etc.), combinations thereof, or the like. In aspects, the method may include providing one or more directions to a surgeon and/or a surgical robot to access one or more regions of the mapped anatomy, overlaying the present map with previously generated maps (so as to evaluate changes in functionality, activity, etc.), combinations thereof, and the like.

The method of FIG. 13c may include delivering a bolus of a composition in accordance with the present disclosure to the target tissues, and optionally assessing an anatomical site of interest within the vicinity of the target tissues or coupled thereto, stimulating one or more physiologic systems in the body, and/or monitoring the evoked response at the anatomical site of interest to determine the effect of the bolus on the target tissues. The method of FIG. 13c may include recording a change in PD. The method of FIG. 13c may include assessing the functionality of the anatomical site of interest, the site of stimulation (i.e., if the stimulation is of a localized type), the target tissues, or an anatomical site there between. The method of FIG. 13c may include assessing if the treatment was successful, such as via recording a marked change in neural traffic from affected tissues, a change in the proportion of neural response to a stress test, etc.

In aspects, the method may include ablating one or more anatomical sites within the body.

In aspects, one or more methods in accordance with the present disclosure may be completed, at least in part, with a delivery tool in accordance with the present disclosure.

Additional method targets include: ganglion sites; innervation along PV and target sites; methods for each procedure; ganglion access; recordings for ganglia localization; methods for each of the therapies; mapping of atria, ventricles, etc.; internal and external approaches; smooth muscle innervation in arteries; treatment of smooth muscle and adjustment of smooth muscle innervation in arteries, vessel walls, etc.; ablation or growth factors; platelet enriched plasma based growth factor injection; valves; biventricular stimulation methods as a stress test; etc.

FIGS. 14a-b illustrate aspects of delivery devices in accordance with the present disclosure. The non-limiting examples of delivery devices shown in the figure are arranged so as to provide a sequence or selection of substances to a treatment region in accordance with the present disclosure. Some non-limiting examples of the use of such devices include providing alternating sequences of ablative agents, delivery of a sequence of ablative agent, sealant, ablative agent, and inflammatory agent, etc. provision for delivery of an antidote, a diluting agent, etc. for collection of a sample, an analyte sample, etc. or the like. FIG. 14a shows a non-limiting example of aspects of a delivery device 1401 in accordance with the present disclosure. The delivery device 1401 includes a plurality of conduits 1409, 1411, 1413 coupled with a plurality of substance reservoirs 1403, 1405, 1407, each substance controllably and selectively deliverable 1423 to a treatment zone 1421. The conduits 1409, 1411, 1413 are coupled to a single delivery tip 1419 in accordance with the present disclosure via an inline manifold 1417. The delivery device 1401 may also include a sensing region 1415 in accordance with the present disclosure. Such an arrangement may be advantageous to deliver sequences of substances in sufficiently small bolus size to a treatment region 1421.

FIG. 14b shows a non-limiting example of aspects of a delivery device 1431 in accordance with the present disclosure. The delivery device 1431 includes a plurality of conduits 1439, 1441, 1443 coupled with a plurality of substance reservoirs 1433, 1435, 1437, each substance controllably and selectively deliverable 1453 to a treatment zone 1451. The conduits 1439, 1441, 1443 are coupled to a single delivery conduit 1450 in accordance with the present disclosure via an inline manifold 1445. The delivery device 1431 may also include a sensing region 1447 in accordance with the present disclosure. In this non-limiting example, a sequence 1449a,b of the substances may be established in the delivery conduit 1450, such as an ablation substance with spatially altered concentration along the length thereof, a substance with alternating contrast agent concentration, an ablative substance with altered viscosity, etc. Such an arrangement may be advantageous to controllably deliver substances to a treatment zone, to form spatially controlled delivery of substance, to deliver more potent treatment to a center of a treatment zone, to form a skin around a treatment zone, to alter the inflammatory properties along a region of the treatment zone, combinations thereof, or the like.

The structures shown in FIGS. 14a-b may be used for a number of applications including but not limited to delivery of multiple chemical types, staged and/or staggered delivery of multiple chemicals, multi-lumen mated delivery (e.g., lumens mated just at the tip so that multiple chemicals can be selectively delivered to a target site, etc.).

FIGS. 15a-g illustrate aspects of treatments on coronary vessels in accordance with the present disclosure. FIG. 15a shows a coronary vessel 1501 including a lumen 1506, a lumen surface 1502, a media 1504, and adventitia 1505.

FIG. 15b shows a delivery tip 1510 in accordance with the present disclosure engaged with a target region of the adventitia 1505 of the vessel 1501, via the lumen 1506, through the lumen wall 1502, the media 1504, and into the adventitia 1505. A bolus 1512 of a composition in accordance with the present disclosure is delivered into the adventitia 1505 to form a treatment zone (in the non-limiting example shown, the treatment zone being an ablation zone). In the non-limiting example shown, the delivery tip 1510 is equipped with a stop 1513 arranged along the length thereof so as to limit the penetration depth of the tip into the lumen wall 1502 of the vessel 1501 during deployment.

FIG. 15c depicts the vessel 1501 after a plurality of boluses have been deposited into the adventitia 1505 of the vessel so as to form a continuous ablation zone 1515 in accordance with the present disclosure.

In aspects, a sensing system in accordance with the present disclosure may be arranged so as to monitor the treatment process, monitor neural traffic in the vessel 1501 before, during, or after delivery, assist in the orientation of the delivery tip 1510 with the lumen wall 1502, etc.

FIG. 15d illustrates a collection of circumferential treatment rings 1520a-c arranged along the length of a vessel 1519. The rings 1520a-c are formed primarily in the adventitia 1521 of the vessel 1519 and the media 1523 has remained relatively untouched by the treatment. Such an arrangement may be advantageous to perform a neural treatment along the vessel with substantially minimal collateral damage to the vessel wall. In aspects, a sensing system in accordance with the present disclosure may be arranged so as to monitor the treatment process, monitor neural traffic in the vessel 1519 before, during, or after delivery, assist in the orientation of the delivery tip with the lumen wall, etc.

FIG. 15e shows a collection of circumferential ring shaped treatment zones 1520a-c arranged along the length of a vessel 1519.

FIG. 15f shows a helical treatment zone 1525 along the length of a vessel 1524.

FIG. 15g shows a longitudinal treatment zone 1530 along the length of a vessel 1529 coupling a region of well innervated vessel 1531 across a region with aberrant innervation or neural activity 1533 to a different region of the vessel 1529.

The compositions, delivery systems, and methods outlined in the in the present disclosure will be better understood by reference to the following examples and Figures, which are offered by way of illustration and which one of skill in the art will recognize are not meant to be limiting.

Example 1

Control

A composition of ethyl alcohol (purchased from Sigma Aldrich), was mixed with 0.01% wt of a fluorescein fluorescent marker. The composition was mixed until a substantially homogenous distribution of the marker was obtained in the solution. This solution was used as a control in the following tests.

Example 2

A composition in accordance with the present disclosure was fabricated according to the following recipe. Ethyl alcohol and hydroxypropyl cellulose (average molecular weight [Mw] of approximately 1 million) were purchased from Sigma Aldrich. 2 parts of the HPC powder were dispersed into 100 parts of ethyl alcohol and mixed with a high shear mixer at a temperature of approximately 45-50° C. until a substantially homogenous mixture was produced. A fluorescein marker (0.01% by wt) was added to the mixture to assist with visualizing the migration thereof in tissues.

A composition with a low shear rate viscosity of greater than 1000 cps was formed.

The resulting composition was loaded into a 0.5 mL syringe and was delivered to tissues through a 25 gauge needle in the following tests.

Figure 16A:
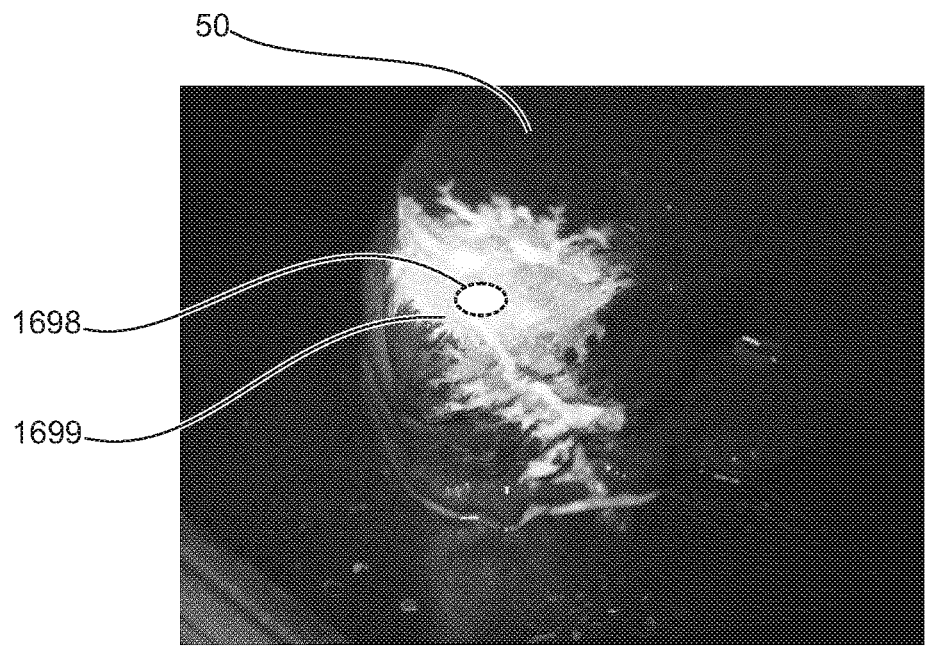
FIGS. 16a-b show an example of tissue ablation with neat ethanol and with a composition in accordance with the present disclosure.
Figure 16B:
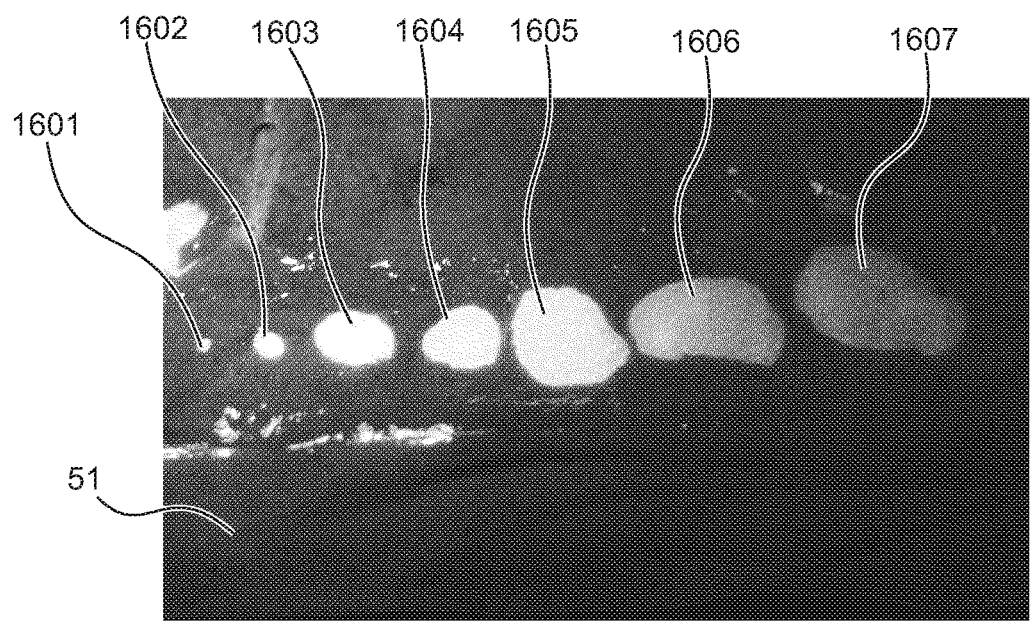

FIGS. 16a-b show an example of tissue ablation with neat ethanol (as formulated in Example 1 CONTROL above) and with a composition (as formulated in Example 2 above) in accordance with the present disclosure. FIG. 16a shows the free surface migration of a 50 µL bolus 1699 of neat ethanol (including a fluorescein fluorescent marker), injected onto a free surface of liver tissue 50. The target ablation zone 1698 is highlighted for reference. As shown in FIG. 16a, the ethanol migrated a substantial distance from the delivery site (measured in excess of 30 mm from the delivery site), with a substantial portion of the bolus flowing away from the delivery site off of the liver tissues 50. Furthermore, histological analysis of the liver tissue 50 demonstrated very little of the tissue was ablated by the ethanol, with only a small grouping of uncontrolled regions around the deposition site being suitably treated by the bolus. In addition, controlled delivery of a specific bolus of ethanol was challenging given the low viscosity thereof.

FIG. 16b shows free surface migration of a range of bolus sizes of a composition in accordance with the present disclosure, as fabricated in Example 2 on a surface of liver tissue 51. The bolus sizes from left to right are 10 µL 1601, 20 µL 1602, 400 µL 1603, 40 µL 1604, 600 µL 1605, 80 µL 1606, and 100 µL 1607. For reference of scale, the 100 µL 1607 bolus has a total width of approximately 12 mm. Histological analysis of the liver sample 51, demonstrated clear, spatially-controlled ablation of tissues under each of the boluses with very clearly defined margins (within 1 mm of the fluorescing margins visible in FIG. 16b).

Figure 17A:
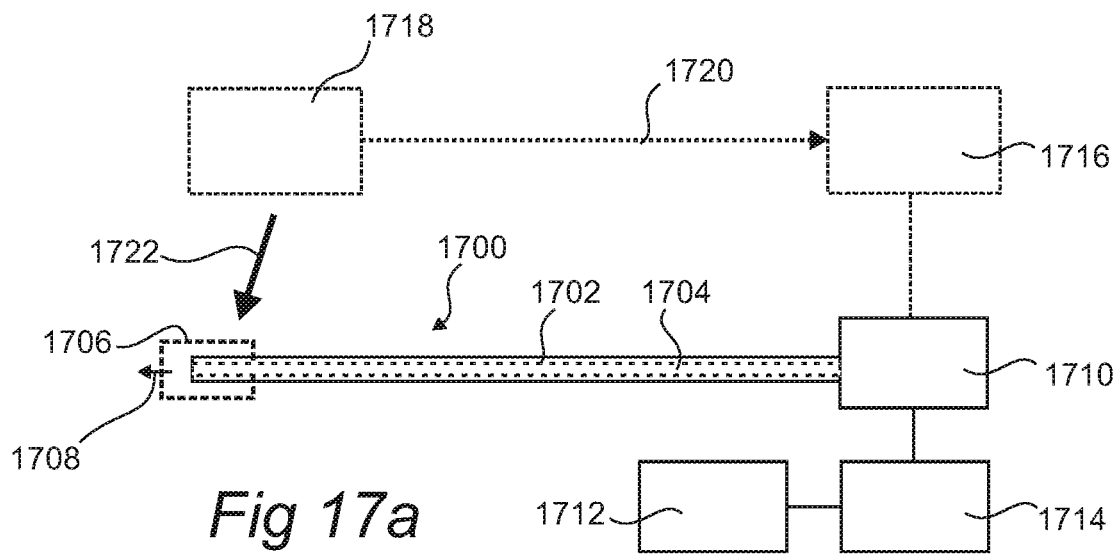
FIGS. 17a-d show schematics of aspects of a delivery system in accordance with the present disclosure.

FIGS. 17a-d show schematics of aspects of a delivery system in accordance with the present disclosure. FIG. 17a shows aspects of a system for performing a procedure in accordance with the present disclosure. The system is shown as configured for interfacing with a surgical site within a body, a subject, a patient, etc. The system includes a delivery tool 1700 in accordance with the present disclosure. The delivery tool 1700 may include one or more lumens 1704 configured to connect a distal tip thereof to a proximal end (e.g., a controller, a connector, a delivery end, etc.), the lumen 1704 shaped and dimensioned such that a composition in accordance with the present disclosure may be delivered 1708 to a target site 1706 in the body. During use, the delivery tool 1700 may be configured to interact with the target site 1706 in accordance with the present disclosure. In aspects, the delivery tool 1700 may be coupled to a connector 1710, the connector providing a mechanical, electrical, fluid, and/or optical interface between the delivery tool 1700 and one or more other modules of the system. In aspects, the delivery tool 1700 may include an embedded local microcircuit (a microcircuit, a switch network, a signal conditioning circuit, etc.) in accordance with the present disclosure. In aspects, the connector 1710 may include a local microcircuit in accordance with the present disclosure.

In aspects, the connector 1710 may be coupled to an operator input device 1714 (e.g., an injector, a foot pedal, an advancing slider, a torqueing mechanism, a recording button, an ablation button, etc.). In aspects, the connector 1710 may be coupled to or include a control unit configured to accept one or more signals from the surgical tool 1700, communicate one or more control signals thereto, send one or more pulsatile and/or radio frequency signals to the microcontroller, record one or more electrophysiological signals from the microsurgical tool, or the like.

In aspects, the control unit 1710 (e.g., coupled to or included in the connector 1710), may be connected to a display 1716 configured to present one or more aspects of the recorded signals obtained at least in part with the surgical tool 1700 to an operator, to present a map, at least partially dependent on the recorded signals, one or more metrics relating to the monitoring, one or more diagnostic test results, one or more stimulator test results, one or more electrophysiological maps, one or more neural structures to be preserved, etc.

In aspects, the connector 1710 may be connected to an injector 1714 (e.g., a manual high pressure injector, a syringe pump, a micro-injector, a power injector, etc.). The injector 1714 coupled to a reservoir 1712, the reservoir 1712 configured to house a composition in accordance with the present disclosure prior to delivery to the target site 1706.

In aspects, the system may include an imaging system 1718, the imaging system may include an ultrasound element, a transducer, a piezoelectric element, an OCT element, a capacitive micromachined ultrasound transducer, a camera, an infrared camera, a near infrared camera, a deep tissue penetrating imaging element, an MRI, a CT system, or the like to image the tissues in the vicinity of the distal tip of the delivery device 1700 during a procedure. Such elements may be advantageous for mapping, defining "keepout" zones, or monitoring tissues before, during or after a surgical procedure, monitoring migration of a composition after injection into the treatment site 1706. Feedback from the elements may be advantageous for determining which nerves to spare and which nerves to treat as part of a procedure.

In aspects, the imaging system 1718 may also be suitable for delivering ultrasound energy to one or more of the target tissues/features, as part of a treatment process (e.g., such as via a HIFU transducer, etc.). In one non-limiting example, the imaging system 1718 may be configured to enable dual function imaging and sonication of a target site 1706 in the body, (e.g., a vessel, innervated tissues, an organ, a ganglion, etc.), or between combinations thereof (i.e., an imaging/sonicating probe located in a first orifice and a guiding element, coupled element, etc. located in a second orifice).

In aspects, the imaging system 1718 may be coupled 1720 to the display 1716 to provide visualization of the target site 1706, monitor migration of a composition near the target site 1706, overlay a physiologic signal over the image of the target site 1706, etc.

In aspects, a procedure in accordance with the present disclosure may include inducing a partial or complete block of a neural signal, and/or receptor, augmentation of the function of a receptor, transmission of a neural signal (i.e., to/from a target organ), a partial and/or substantial neurectomy, peripheral neurectomy, sympathectomy, parasympathectomy, and the like.

In aspects, one or more systems in accordance with the present disclosure may be coupled with one or more imaging modalities including computer assisted imaging computed tomography (CT), magnetic resonance imaging (MRI), positron emission tomography (PET), optical coherence tomography (OCT), magnetoencephalography (MEG), functional MRI, stereotactic surgery, and the like before, during, and/or after a surgical procedure. Such imaging modalities may be included in the imaging system 1718, and may be used to provide visualization 1722 of a target tissue, of inflammation (e.g., inflammation as caused by an associated disease state, as caused by a procedure, etc.), of advancement of one or more aspects of the system towards the target tissue, etc. Use of such imaging modalities may be performed prior to/after surgery and/or intraoperatively.

In aspects, one or more distal tips or delivery elements of the delivery tool 1700 in accordance with the present disclosure may include a fiber optic coupled to a laser (i.e., fiber optic guided radiation to a target tissue), a cryotherapy unit, a heat circulation unit (i.e., a unit for heated wire thermal therapy), an ultrasonic generator, or the like for treatment of target tissue. For purposes of discussion, the majority of non-limiting examples discussed herein are directed to electrical interfacing with tissues, ultrasonic interfacing with tissues, and chemical delivery aspects of such therapies.

A delivery system in accordance with the present disclosure may be configured such that at least a portion thereof may be placed into a lumen (e.g., an artery, a vein, an arteriole, a venule, a duct, a chamber, a pocket, a tubule, a bowel, a urethra, or the like), and/or an organ (e.g., a prostate, a testicle, a kidney, a stomach, a brain, a pancreas, a liver, a lung, or the like) so as to access the neural structure for purposes of diagnosis, and/or treatment of a disease state.

In aspects, the delivery tool 1700 may include an elongate member and one or more probes (e.g., shanks, needles, microneedles, microneedle electrodes, microneedle fluid delivery catheters, anchors, multi-electrode arms, stabilization arms, combinations thereof, or the like) each in accordance with the present disclosure. One or more of the probes may be coupled to the elongate member. In aspects, at least one probe may be configured so as to slide-ably advance from the elongate member into the wall of a lumen adjacent thereto. The probe may be configured to interface with one or more target tissues in the wall, and/or with a volume of tissue externally positioned with respect to the wall. In aspects, the elongate member may be sized and dimensioned to be delivered via a lumen to the vicinity of a target tissue, the probes may then be advanced therefrom, through the wall of the lumen and into the target tissue in order to monitor, treat, diagnose a condition, or the like.

In aspects, the system may include a plurality of probes, the probes oriented so as to protrude from the elongate member during an actuation (i.e., a deployment or retraction of the probes from the elongate member, such actuation may be automatic, semi-automatic, manual, etc.). Each probe may be configured so as to be advance-able into a lumen wall adjacent thereto during a deployment procedure. One or more probes may be configured to communicate (e.g., fluidically communicate, electrically communicate, optically communicate, etc.) with the target tissues, with another device coupled to the body (e.g., an electrode, a surgical tool in accordance with the present disclosure, etc.), and/or between two or more probes.

In aspects, one or more probes may be arranged so as to be advanced, retracted, twisted, and/or actively bent (e.g., in the case of an active material based probe, a micro-wire actuated probe, etc.) either manually by an operator, or via a robotic actuation (e.g., a mechanism, a servo-controlled mechanism, etc.) during a deployment procedure. Such a configuration may be advantageous for assisting with placement of a probe during a procedure, with aligning a probe with a region of target tissue, advancing the probe through a target tissue, precisely placing one or more regions of the probe within a target tissue, etc.

In aspects, one or more probes may include a microneedle electrode, configured such that at least a portion thereof (e.g., a tip, a shank, a region, a plurality of regions, etc.) may be configured so as to facilitate electrical communication with one or more target tissues adjacent thereto, one or more probes, and/or one or more external electrodes as part of a deployment, monitoring, or treating procedure.

In aspects, a probe may include an array of electrodes, configured so as to assist with determination of a local field gradient, configured so as to monitor a plurality of sites along the length of the probe, to provide a configurable electrode arrangement for sensing, stimulation, ablation, etc.

In aspects, one or more electrodes may be arranged with an active area (i.e., area available to electrically interface with adjacent tissues) of less than 10 $mm^2$, less than 1 $mm^2$, less than 0.1 $mm^2$, less than 10,000 $\mu m^2$, less than 1,000$\mu^2$, less than 100 $\mu m^2$, less than 1 $\mu m^2$, etc. Alternatively, one or more electrodes may be configured so as to form electrical impedance in normal saline of greater than 100 ohms ($\Omega$), greater than 1k$\Omega$, greater than 1001a greater than 1M$\Omega$, greater than 10M$\Omega$, greater than 50M$\Omega$, etc.

In aspects, one or more probes may be configured with a characteristic width (i.e., a dimension perpendicular to a length measurement thereof, for example, a diameter), of less than 1 mm, less than 200 $\mu$m, less than 100 $\mu$m, less than 50 $\mu$m, less than 12 $\mu$m, less than 3 $\mu$m, etc. Such characteristic width may vary along the length of the probe. In aspects, one or more probes may be tapered to a fine tip (e.g., a tip with less than 5 $\mu$m radius of curvature, less than 1 $\mu$m radius of curvature, etc.) so as to more easily be advanced through tissues during a procedure.

In aspects, one or more regions of a probe or elongate member in accordance with the present disclosure may be coated with a substance and/or treated so as to be lubricious in the presence of water. Some non-limiting examples of such coatings include a hydrophilic coating, a silicone coating, a PTFE coating, parylene, a ceramic, PEBAX, a hydrogel, etc. Some non-limiting examples of such treatments include vapor deposition of a ceramic, a polymer, an ion treatment process, an electroplating process, dip process, etc. Such coating may provide for easier deployment as part of a surgical procedure in accordance with the present disclosure.

In aspects, one or more probes may include a tip fashioned with a tip electrode (e.g., an exposed region of the probe suitable for electrically interfacing with a surrounding tissue, with one or more probes, an external electrode, etc.). In aspects, the tip electrode may be arranged so as to provide a microscopic interface over a length at an end of the probe less than 150 $\mu$m, less than 50 $\mu$m, less than 20 $\mu$m, less than 10 $\mu$m, less than 1 $\mu$m, and the like. Such a configuration may be suitable for spatially precise monitoring of local field potentials during a procedure (e.g., during monitoring of electrophysiological activity, during a denervation procedure, during placement of the probe, etc.). In aspects, the tip electrode may be arranged so as to provide an intermediately sized interface along the length of the probe, greater than 50 $\mu$m but less than 1 mm, greater than 100 $\mu$m but less than 500 $\mu$m, or the like. Such an arrangement may be suitable for stimulating local tissues, for monitoring overall electrophysiological activity around a volume of tissue, to act as a reference electrode, and the like. In aspects, the tip electrode may be configured along a length of the probe greater than 100 $\mu$m, greater than 500 $\mu$m, greater than 1 mm, greater than 2 mm, and the like. Such an arrangement may be advantageous for providing a sufficiently high current to surrounding tissues in the vicinity of the electrode, for example, during a hyperpolarizing stimulation, during an ablation procedure, to substantially affect tissues in the vicinity of the tip electrode, and the like.

In aspects an electrode in accordance with the present disclosure may be formed from an electrically and/or ionically conductive material. Some non-limiting examples of electrode materials include gold, platinum, platinum iridium, stainless steel, tungsten, iridium, palladium, rhodium, organic conducting polymer modified materials, poly (acetylene)s, poly(pyrrole)s, poly(thiophene)s, poly(terthiophene)s, poly(aniline)s, poly(fluorine)s, poly(3-alkythiophene)s, polytetrathiafulvalenes, polynapthalenes, poly(p-phenylene sulfide), poly(para-phenylenevinylene)s, poly(3,4-ethylenedioxy thiophene) (PEDOT), poly(3,4-ethylenedioxythiophe)/poly(styrenesulfonate)(PEDOT/PSS), polyfuran, polyindole, polycarbazole, nanorods, nanotubules, carbon nanotubes, carbon fibers, combinations thereof, hybridized composites thereof, and the like. In one non-limiting example, an electrode in accordance with the present disclosure may include a PEDOT film hybridized with gold nanoparticles (e.g., gold particles with diameter less than 20 nm, less than 15 nm, etc.). In aspects, one or more electrodes may include a nanomaterial filler or functionalized material for enhancing one or more properties thereof (e.g., active area, conductivity, etc.).

In aspects, an electrode including an organic conducting polymer or a functionalized organic conducting polymer (e.g., via grafting of specie to the backbone thereof, grafting of an organometallic, biomolecule, etc. thereto, and the like) may be configured so as to monitor a local event associated with tissues in the vicinity of the electrode during use. In such a configuration, the electrical conductivity of the organic conducting polymer in contact with the surrounding tissues may change by orders of magnitude in response to pH, local potential changes, concentration of an analyte (e.g., a neurotransmitter, a neuroblocker, a neural agonist, a neural antagonist, an inverse agonist, an enzyme, a protein, oxygen, etc.) during use. Such changes may be advantageously monitored during a surgical procedure, so as to assess placement of the probe, determine progress of an associated treatment, or the like.

In aspects, one or more probes/needles may include a fluid delivery channel for delivery of a fluid (e.g., a medication, a stimulant, a neural agonist, a neural antagonist, an inverse agonist, a neuroblocker, a sclerosing alcohol, a neurotransmitter, a chemical denervation agent, a neurodisruptive agent, a sclerosing agent, phenol, alcohol, guanethidine, an antibody drug conjugate, etc.) for delivery to the target tissues. In one non-limiting example, one or more probes may include a microchannel for delivery of fluid. In an aspect associated with a method for treating a target tissue in accordance with the present disclosure, the system may be configured to deliver a bolus of a denervation agent to the target tissues. In aspects, the fluid may be delivered as part of a surgical procedure (e.g., nerve stimulation, denervation, chemical neurolysis, chemical neurolytic blockade, cryoablation, etc.).

In aspects, a system in accordance with the present disclosure may include means for delivering (e.g., channels, a reservoir, a fluid delivery needle, etc.) a composition in accordance with the present disclosure.

Figure 17B:
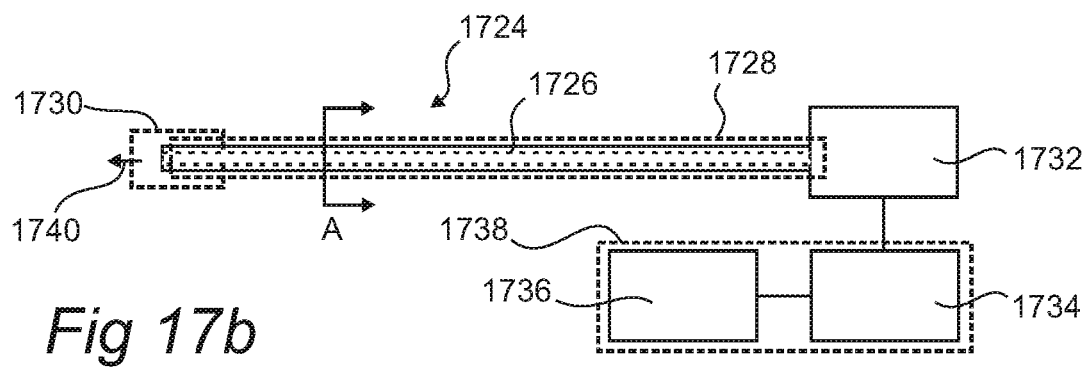

FIG. 17*b* illustrates aspects of a delivery tool 1724 in accordance with the present disclosure. The delivery tool 1724 includes a catheter 1726 including a thermal control element 1728. The thermal control element 1728 is configured to control the temperature of a composition passing through the catheter 1726 towards a target site 1730 in the body. The delivery tool 1724 may include or couple to a connector 1732, an injector 1734, and/or a reservoir 1736 each in accordance with the present disclosure. The delivery system may include an additional thermal control element 1738 coupled to the reservoir 1736 and/or the injector 1734 to maintain a composition therein at a temperature during delivery 1740 of the composition to the target site 1730, during a procedure, prior to delivery 1740, etc.

Figure 17C:
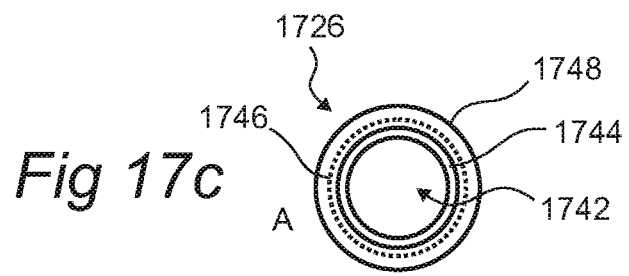

FIG. 17c illustrates a cross section A from FIG. 17b of a catheter 1726. The catheter 1726 is shown with a lumen 1742 running substantially the length thereof, for delivery of a composition there through. A wall of the lumen 1742 may be lubricated, may include a lubricating substance (e.g., a PTFE liner, a silicone oil fluid, a hydrophilic layer, etc.) so as to help with passage of the composition there along during delivery to a target site in a body. The catheter 1726 may include a heater band 1744 to provide a thermal control function along the lumen, the heater band 1744 configured to heat the lumen 1742 so as to maintain a fluid therein at an elevated temperature. In aspects, the heater band 1744 may include a resistive heating element (e.g., a resistive heating coil, etc.), an RF heating element, a fluid transfer jacket, etc.

The catheter 1726 may be constructed by traditional means (e.g., from an extruded tube, layered tubes, braided tube, coiled wire and tube, etc.). In aspects, the catheter 1726 may be constructed in a layer by layer process. The process may include starting with a mandrel, the mandrel shaped so as to form the lumen, optionally a low friction or lubricious sheath placed over the mandrel, a first polymer layer coated onto the mandrel or sheath (e.g., via a solution casting method), the heating element added to the resulting composite (e.g., such as a laser cut hypotube, a resistive coil, reinforcing resistive braid, etc.), one or more additional polymer layers coated onto the heating element and first polymer layer, or one or more additional polymer layers (e.g., one or more insulating layers, etc.), may be coated onto the structure so as to form a thermally insulating layer between the heating element and an outer surface of the catheter.

The catheter 1726 and the heater band 1744 therein may be coupled to a thermal regulating unit 1748, configured so as to control the temperature along the wall of the lumen 1742 during use. In aspects, the lumen 1742 may be maintained at a temperature of 40-50° C., of 43-47° C., etc. In aspects, a phase change composition in accordance with the present disclosure may be delivered through the catheter 1726, the lumen 1742 heated such that the phase change composition maintains a first state (e.g., a substantially low viscosity state), and upon delivery to the target site within a body, the phase change composition transitions to a second state (e.g., a gel state, a substantially high viscosity state, a solid state, etc.).

Figure 17D:
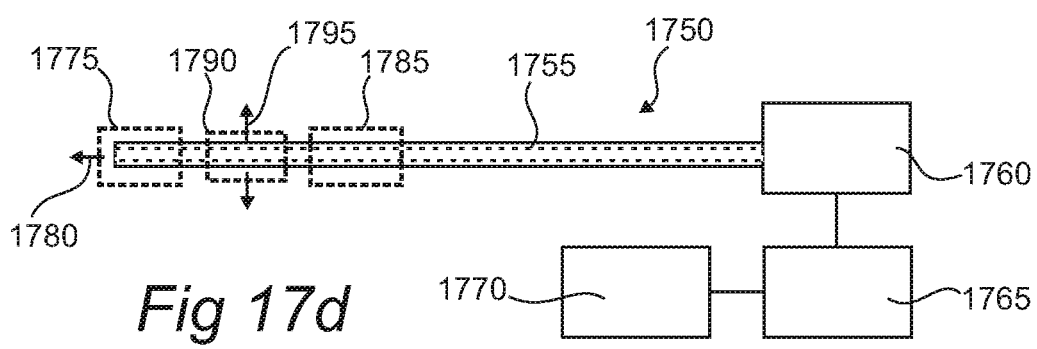

FIG. 17d shows a schematic of aspects of a delivery tool 1750 in accordance with the present disclosure. The delivery tool 1750 may include a lumen 1755 arranged therein so as to couple a connector/controller 1760 to a distal tip for delivery 1780 of a composition in accordance with the present disclosure to a target site in a body. The delivery tool 1750 may include one or more sensing regions 1775, 1785 for monitoring one or more electrophysiological signals, one or more physiologic parameters, or the like. In aspects, the delivery tool 1750 may include one or more ablative zones 1790, the ablative zone 1790 optionally including a biasing function 1795 (e.g., a balloon, a deployable region, a helical region, a shaped region, etc.) configured so as to bias against the walls of a vessel in the body during a procedure so as to deliver energy, a compound, inject a needle into, the wall of the vessel, etc.

In aspects, the delivery tools 1700, 1724, 1750 may be configured to deliver one or more diagnostic or stressing agents into a vessel in the body. Some non-limiting examples of such agents include neuro-stimulants, neuro-blockers, neuro-depressors, diuretics, hormones, steroids, nutrients, enzymes, biomarkers, antibodies, proteins, carbohydrates, analgesic, saline, plasma, combinations thereof or the like. The delivery of a stressing agent may be used in conjunction with the sensing to determine the organ response, a bodily response, etc. to the resulting stress state. Such delivery may be directed into an organ, a portion of an organ, a vessel wall serving an organ, into a ganglion, etc. in order to assess function and/or generate a stress response therefrom.

FIGS. 18a-j show aspects of patterned delivery of a composition in accordance with the present disclosure to a volume of tissue.

Figure 18A:
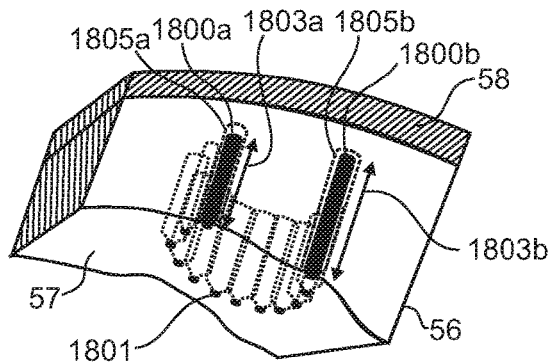
FIGS. 18a-j show aspects of patterned delivery of a composition in accordance with the present disclosure to a volume of tissue.

FIG. 18a illustrates a volume of tissue 56 with an accessible face 57 through which a composition in accordance with the present disclosure has been injected, so as to form a pattern within the volume of tissue 56. The volume of tissue 56 may be associated with an organ tissue, adipose tissue, a vessel, a lumen wall, a muscle, a cardiac muscle, a brain tissue, an artery wall, a bowel wall, a bladder wall, etc. The composition is shown having been injected into the volume of tissue 56 through the accessible face 57 via one or more injection sites 1801, each bolus 1800a,b of the composition optionally shaped in accordance with the present disclosure (i.e., in this non-limiting example, shown as a post or elongated shape). In order to form a macroscopic shape in the volume of tissue 56, the boluses 1800a,b may be formed via one or more injection sites 1801, along a path within the volume of tissue 56, at coordinates within the volume of tissue 56, etc. As shown in FIG. 18a, the boluses 1800a,b are formed as posts, each with a characteristic length 1803a,b and width so as to form a substantially continuous fence around a region within the volume of tissue 56. In aspects, upon delivery to the volume of tissue 56 one or more components of the boluses 1800a,b may migrate into the surrounding tissues, so as to form a zone of effect 1805a,b. In aspects, the zone of effect 1805a,b may be arranged (i.e., based on the migration of the desired component in the composition into the surrounding tissues, based on uptake into the tissues, etc.) such that an essentially continuous "structure" of effected tissues are formed in the volume of tissue 56. In aspects, the zone of effect 1805a,b may be arranged such that isolated regions of tissue are affected by the treatment (i.e., such as around a vessel, within a tumor, around a diseased tissue, etc.).

In aspects, the volume of tissue 56 may include a region 58 which is not meant to be treated (e.g., a region of tissue that is meant to be preserved, a region that is not meant to substantially receive an active agent, etc.). Such a region 58 may be part of an adjacent organ, region of tissue on the existing organ that is functioning, a region that is susceptible to failure, provides a barrier function, etc.

Figure 18B:
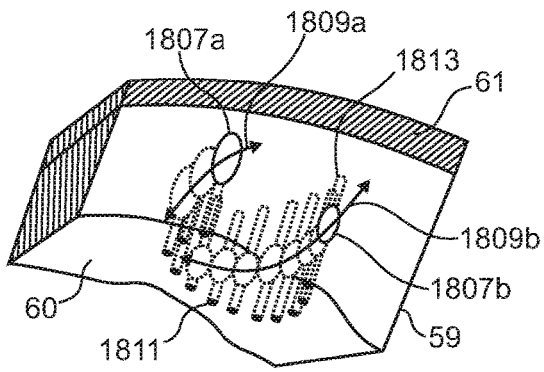

FIG. 18b illustrates a volume of tissue 59 with an accessible face 60 into which an array of boluses 1807a,b have been injected, so as to form one or more paths 1809a,b through the volume of tissue 59, for treatment of the tissues in the immediate vicinity of the path 1809a,b. In FIG. 18b, the pathways 1809a,b are formed through multiple injections and delivery of boluses 1807*a,b* at sites within the volume of tissue 59. The injections were made through injection sites 1811 along the accessible face 60 of the volume of tissue 59. The needle tracks 1813 for the injections are shown for clarity.

In aspects, more complex patterns, multiple paths 1809*a, b*, etc. may be formed through a plurality of injections, such as placement of substantially spherical boluses, at sites in the 3D volume of tissue 59. Such an approach may be a-likened to a raster printed 3D shape, so as to form a barrier around a tumor margin, to follow a 3D pathway through a volume of tissue, etc.

Alternatively, additionally, or in combination, one or more of the paths 1809*a,b* may be formed by passage of a needle through the volume of tissue 59, along a desired trajectory. The boluses 1807*a,b* may be delivered either during insertion, pull back (such as with a delivery system having an end port on the needle for delivery), once the needles are placed (such as from a needle with multiple delivery ports, etc.), etc.

Similar to FIG. 18*a*, in aspects the volume of tissue 59 may include a region 61 which is not meant to be treated (e.g., a region of tissue that is meant to be preserved, a region that is not meant to substantially receive an active agent, etc.). Such a region 61 may be part of an adjacent organ, region of tissue on the existing organ that is functioning, a region that is susceptible to failure, provides a barrier function, etc.

Figure 18C:
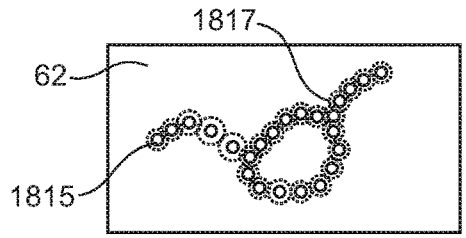

FIG. 18*c* illustrates a treatment pattern formed within a volume of tissue as seen from an accessible surface 62. The pattern is formed through a plurality of injections of boluses 1815, which may migrate locally to form regions of treatment 1817 around the boluses 1815. The pattern may include linear regions (so as to form a fence like barrier in cardiac tissues, so as to follow along a vessel, so as to follow along a neural plexus, etc.), circular regions (so as to isolate a region of tissue from a region around it, to modify a conduction pathway through a volume of tissue, etc.).

Figure 18D:
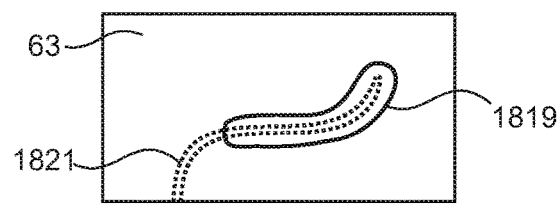

FIG. 18*d* illustrates a treatment pattern formed within a volume of tissue as seen from an accessible surface 63. The pattern is formed by deposition of a bolus 1819 of a composition in accordance with the present disclosure into the tissues along a pathway (e.g., a straight pathway, a curved pathway, a circular pathway, a tortuous pathway, etc.). As shown in FIG. 18*d*, the delivery needle injection pathway 1821 is shown to further highlight the concept of shaping the bolus 1819 to conform to a specific region within the tissues.

Figure 18E:
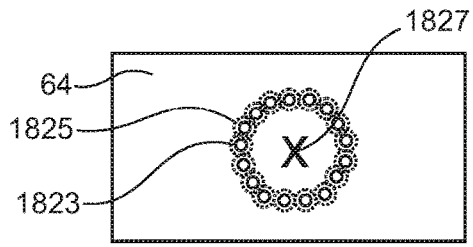

FIG. 18*e* illustrates a treatment pattern formed within a volume of tissue as shown from an accessible surface 64. The treatment pattern is formed during a series of injections 1823 of a composition in accordance with the present disclosure, to form an effective treatment region 1825, in this case the pattern formed in a circular shape so as to isolate a region 1827 of the tissues from the surrounding tissues. Such an approach may be advantageous for altering the conduction of a bioelectrical signal through a muscle in the body, to isolate an asynchronous pacing center from nearby tissues, etc.

Figure 18F:
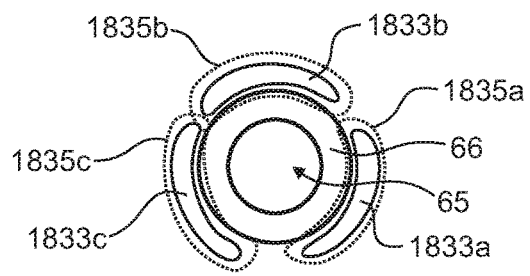

FIG. 18*f* illustrates a treatment pattern formed around a lumen 65 in a body, near to, through, and/or within a wall 66 of the lumen 65. The pattern is shown in a circumferential arrangement around the lumen 65. The boluses 1833*a-c* of one or more compositions in accordance with the present disclosure have been injected into the tissues surrounding the lumen 65, in this case, so as to form a substantially complete ring around the lumen 65. The boluses 1833*a-c* may have been injected through the wall 66 of the lumen 65 (i.e., from within the lumen), from an endoscopic approach (i.e., from outside the lumen 65), etc. One or more components of the composition in the boluses 1833*a-c* may migrate so as to form a treatment zone 1835*a-c* around the lumen 65. Such an approach may be advantageous for substantially forming a ring like treatment zone 1835*a-c* around a lumen 65 in a body.

Figure 18G:
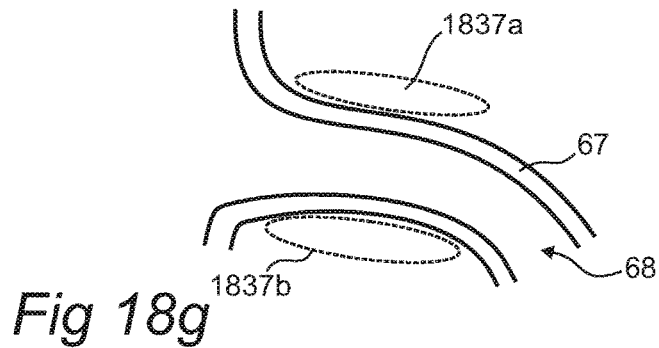

FIG. 18*g* illustrates an axial treatment pattern 1837*a,b* formed along a vessel 67 in a body. The axial treatment pattern 1837*a,b* may be formed through delivery of a composition through the wall of the vessel 67, such as via a delivery system in accordance with the present disclosure placed within a lumen 68 of the vessel 67. Such an axial treatment pattern 1837*a,b* may be formed through multiple delivery of boluses, through a shaped injection needle approach, or the like. Such an approach may be advantageous to limit regrowth of nerves along the walls of the vessel 67 after treatment thereof (i.e., so as to increase the durability of such a treatment).

Figure 18H:
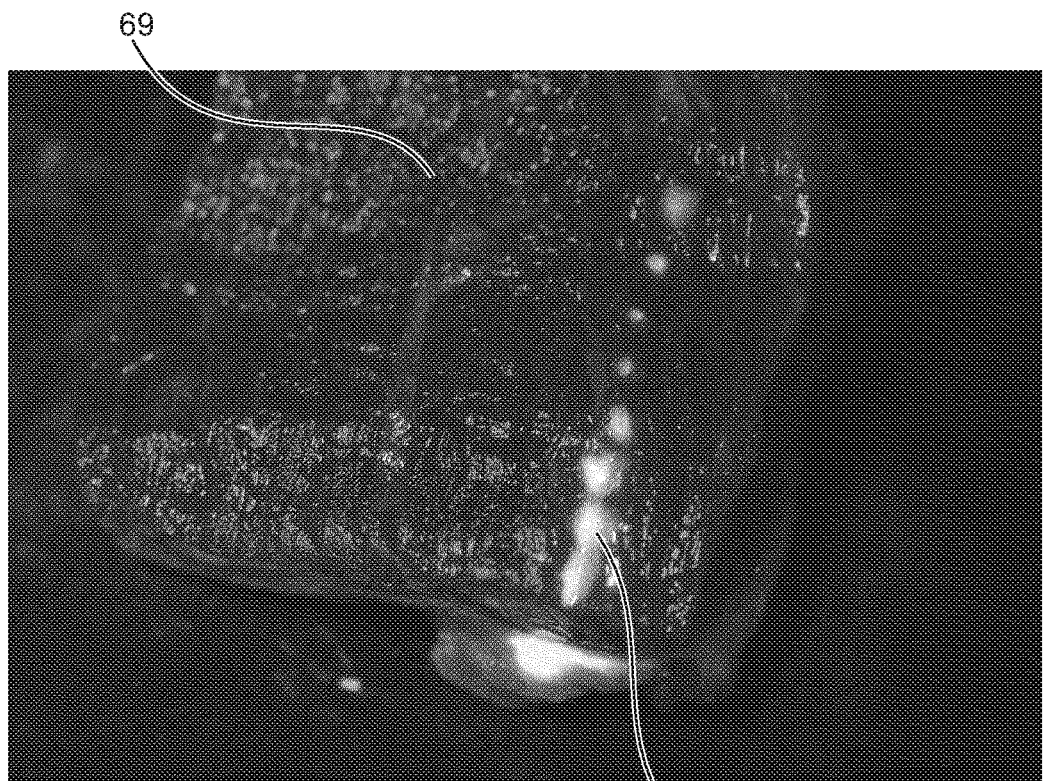

FIG. 18*h* shows a sample of muscle tissue 69 treated with a patterned example of a composition in accordance with the present disclosure. The composition is the same as described in Example 2, and was injected into the muscle tissue so as to form a wall of boluses in accordance with the present disclosure to form a series of boluses 1839. The injections were made through a 25g stainless steel injection needle. The boluses 1839 were formed by simultaneously injecting while retracting the injection needle from the tissues (i.e., so as to form an elongate bolus along the injection pathway). Alternatively, additionally, or in combination other approaches to forming the desired pattern in the tissue 69 may be employed in accordance with the present disclosure.

Figure 18I:
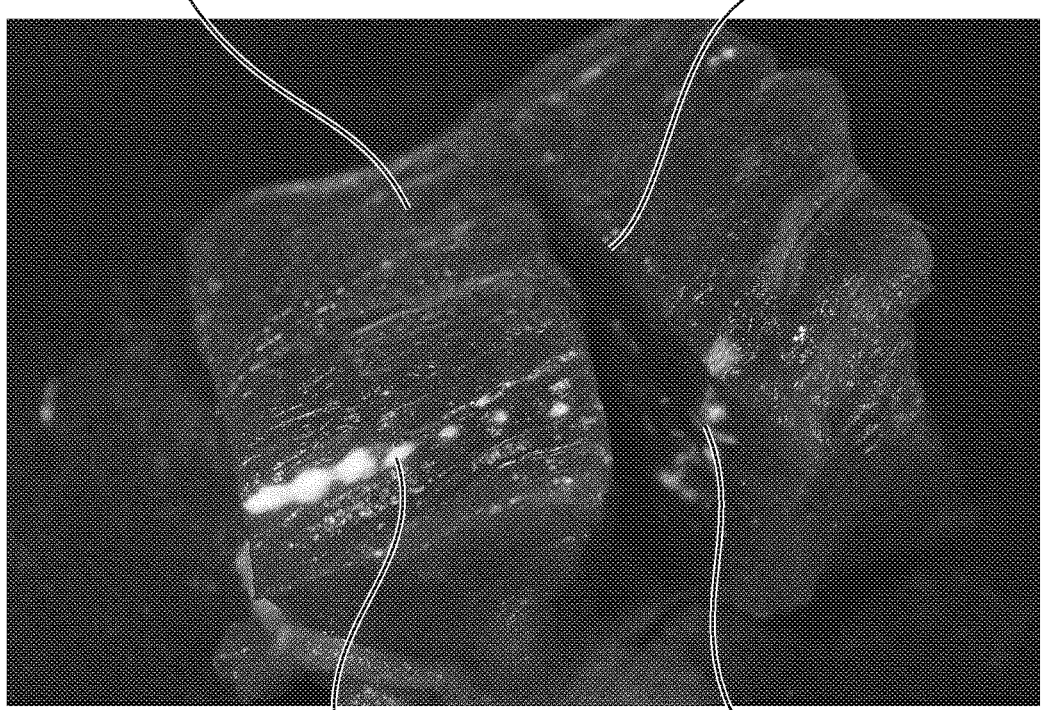

FIG. 18*i* shows the sample of muscle tissue 69 after being treated with a pattern of boluses 1839 of a composition in accordance with the present disclosure. The muscle tissue 69 has been sliced 70 along a trajectory perpendicular to the pattern, so as to assess the width thereof post treatment. The width 1841 of the "wall" pattern can be seen, wherein minimal lateral migration of the boluses 1839 occurred post injection.

Figure 18J:
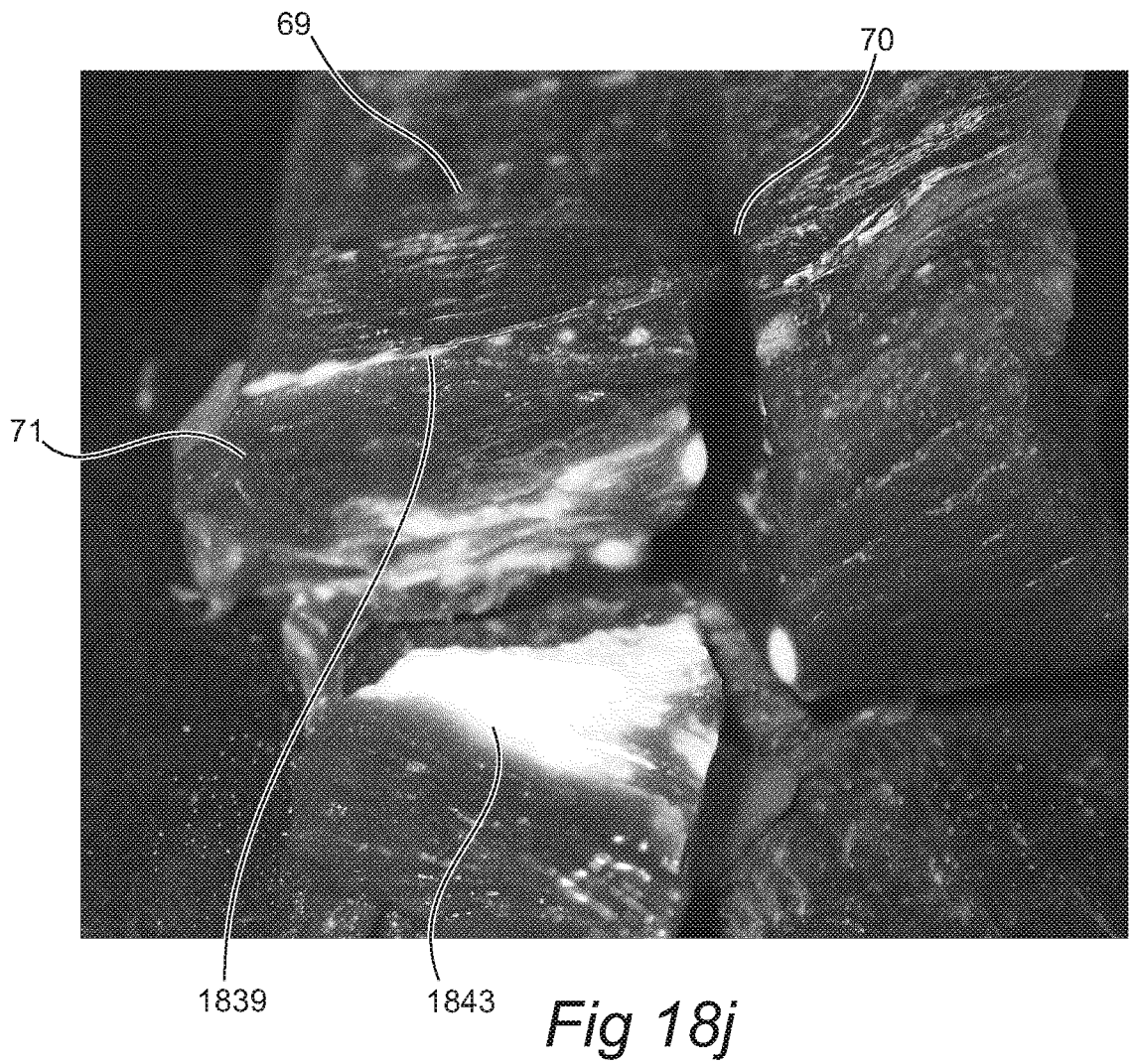

FIG. 18*j* shows the sample of muscle tissue 69 after being sliced 70 along a trajectory perpendicular to the pattern of boluses 1839, and then sliced 71 again along the pattern of boluses 1839. The second slice 71 illustrates how a substantially uniform treatment zone 1843 was formed within the muscle tissue 69 around the pattern. Collectively FIGS. 18*h-j* illustrate how a composition and injection method in accordance with the present disclosure may be used to form a patterned treatment zone within a volume of tissue 69 in a body. Such an approach may be advantageous to target treatment of cardiac muscle regions, or coronary vessels without charring, or scarring the lumen of the chamber or the media of the vessel nearby the treatment regions.

FIGS. 19*a-l* show aspects of delivery tips in accordance with the present disclosure.

FIG. 19*a* shows a needle like delivery tip 1900 in accordance with the present disclosure to deliver a bolus of a composition in accordance with the present disclosure to a target tissue site within a body. The delivery tip 1900 includes a plurality of ports 1906 connected to a lumen within the delivery tip 1900. The ports 1906 may be arranged at one or more sites along the length of the delivery tip 1900 so as to provide a particular shape to the bolus delivery, etc. The ports 1906 may be distributed over the delivery tip 1900, sized, and/or shaped so as to influence the bolus shape over the delivery tip 1900. The delivery tip 1900 is configured to accept the composition through the lumen from a coupled injector 1908 during delivery. During delivery the composition is delivered 1910 to the tissues through the ports 1906. In aspects, the delivery tip 1900 may include one or more sensors 1904, electrodes, or the like to monitor local physiologic activity, monitor the movement or migration of the composition after injection, etc. In this non-limiting example, the sensor 1904 is configured as an electrode, may include one or more exposed regions, each exposed region configured to interact with tissues and measure an electrophysiological signal therefrom. One or more of the sensors 1904 may be configured in accordance with the present disclosure so as to assist in the guidance of the tip, measure local electrophysiological activity, determine bolus margins, determine when the tip is within a target tissue site, etc.

The delivery tip shown in FIG. 19a shows a delivery tip 1900 with a closed end 1902, such that delivery of the bolus is made along the shank of the delivery tip 1900.

FIG. 19b shows the tip from FIG. 19a after delivery 1910, 1912 of a bolus 1914 of a composition in accordance with the present disclosure to a target tissue site surrounding the delivery tip 1900. In this non-limiting example, the ports 1906 are distributed and shaped such that the bolus 1914 is substantially elongate in shape (e.g., sausage like, fence post like, cylindrical in shape, etc.).

FIG. 19c illustrates aspects of a delivery tip 1916 in accordance with the present disclosure with a sharp tip, the sharp tip including a port 1920, the delivery tip 1916 including a lumen 1918 in fluid communication with a proximal end thereof (e.g., a connector, a controller, an injector, etc.).

FIG. 19d illustrates the delivery tip 1916 after delivery 1918 of a bolus 1920 of a composition in accordance with the present disclosure through the delivery tip 1916 to a tissue site in a body. In this non-limiting example, the bolus 1920 forms an essentially spherical shape upon delivery 1918 to the tissues. In aspects, the position of the delivery tip 1916 may be moved 1922 so as to adjust the shape of the bolus 1920 being delivered to the tissues. In aspects, the composition may include a contrast agent, so as to provide imaging of the injection site within the tissues. Movement 1922 of the delivery tip 1916 may be coordinated with the delivery 1918 and the imaging in order to control the shape of the bolus 1920 at the delivery site in the body.

FIG. 19e illustrates a curved delivery tip 1924 in accordance with the present disclosure, configured so as to be advanced 1926 into a volume of tissue in the body, the curvature providing a change in direction of the tip 1924 so as to follow a path that is different than the initial direction of advancement within the tissues. The curved delivery tip 1924 may include a plurality of ports 1928 through which one or more boluses of a composition may be delivered 1930 to the tissues. Such a configuration may be advantageous for forming a linear track of the composition within the tissues in a direction substantially different from the orientation of the delivery tip 1924 to the tissues. Such a configuration may be advantageous for treating a linear track of tissues near to the surface of a volume of tissue, along a surface of a volume of tissue, etc.

FIG. 19f illustrates a delivery tip 1932 in accordance with the present disclosure, the delivery tip 1932 including a deployable delivery member 1934 (e.g., a helically shaped, spiral shaped, circular shaped, elliptically shaped, etc.) configured such that the deployable delivery member 1934 may take on a shape when deployed 1938 from the delivery tip 1932. In aspects, the deployable delivery member 1934 may be shaped such that it can form a shape within a volume of tissue, or upon deployment within a lumen in a body (such that it can be biased against a wall of the lumen after deployment). In aspects, the deployable delivery member 1934 includes a plurality of ports 1936 arranged along the length thereof through which a composition in accordance with the present disclosure may be delivered 1940 there through to a volume of tissue along a surface within a body, etc. Such a configuration may be advantageous to form a shaped delivery element that may be stably biased against a surface. The deployable delivery member 1934 and the ports 1936 arranged thereupon may be arranged such that the delivery 1940 of the composition is substantially directed against a surface or along a side of the shape formed after deployment 1938. Such a configuration may be advantageous to deliver a composition to a surface of a volume of tissue in a body.

FIG. 19g illustrates a curved delivery tip 1942 in accordance with the present disclosure, configured so as to be advanced 1946 into a volume of tissue in the body, the curvature providing a change in direction of the tip 1942 so as to follow a path that is different than the initial direction of advancement within the tissues. The curved delivery tip 1942 may include a plurality of ports 1944 through which one or more boluses of a composition may be delivered 1948 to the tissues. As shown in FIG. 19g the ports 1944 are distributed on the tip 1942 such that the composition would be delivered to a side thereof, such that if the tip 1942 was biased towards a surface, a composition could be delivered thereto and dwell between the biased tip 1942 and the surface so as to treat a region of the surface. Such a configuration may be advantageous for treating a linear track of tissues near to the surface of a volume of tissue, along a surface of a volume of tissue, etc.

FIG. 19h illustrates a profile of ports 1950 arranged along a delivery tip 1952 with varying characteristic width, such that delivery 1956 of a composition therefrom forms an elliptical profile 1954 (e.g., an egg like profile, a top like profile, elliptical lobes, etc.). In aspects, the profile 1954 may take on a lobe like structure (such as pedals on a flower when looking axially down the axis of the delivery tip 1952), etc. The ports 1950 are shaped and arranged such that the larger diameter ports 1950 are situated towards the center of the delivery region (the region around which the composition is delivered), while smaller diameter ports 1950 are located near to the edges of the delivery region, so as to form the desired elliptical profile 1954.

FIG. 19i illustrates a profile of ports 1958 arranged along a delivery tip 1960 with varying characteristic width, such that delivery 1964 of a composition therefrom forms an conical profile 1962 (e.g., an arrowhead-like profile, a pedal like conical profile, etc.). In aspects, the profile 1962 may take on a lobe like structure (such as pedals on a flower when looking axially down the axis of the delivery tip 1960), etc. The ports 1958 are shaped and arranged such that the larger diameter ports 1958 are situated towards one end of the delivery region (the region around which the composition is delivered), while smaller diameter ports 1958 are located near to the other end of the delivery region, so as to form the desired conical profile 1962.

FIG. 19j illustrates a profile of ports 1966 arranged along a delivery tip 1968 with varying characteristic width, such that delivery 1972 of a composition therefrom forms a directed profile 1970a, 1970b (e.g., a profile where the delivery 1972 is asymmetrically directed around the delivery tip 1968 so as to preferentially deliver the composition to a side of the delivery tip 1968). In aspects, the profile 1970a,

1970*b* may take on a lobe like structure (here being a single pedal or lobe to a side of the delivery tip 1968), etc. The ports 1966 are shaped and arranged along a side of the delivery tip 1968 such that the larger diameter ports 1966 are situated towards one end of the delivery region (the region around which the composition is delivered), while smaller diameter ports 1966 are located near to the other end of the delivery region, so as to form the desired asymmetrically directed conical profile 1970*a*, 1970*b*.

FIG. 19*k* illustrates a profile of ports 1976 arranged along a spiral shaped delivery tip 1974 with varying characteristic width, such that delivery 1980 of a composition therefrom forms a toroidal profile 1978 (e.g., a donut like profile, a ring-like profile, shaped so as to isolate a region from the surrounding tissues, etc.). In aspects, the profile 1978 may take on a beaded string like structure (such that individual boluses are arranged along the shape of the profile so as to form an undulating toroidal shape), etc. The ports 1976 may be distributed, shaped, and/or arranged so as to alter the shape of the toroidal profile 1978.

FIG. 19*l* illustrates a profile of ports 1982 arranged along a delivery tip 1984 with varying characteristic width, such that delivery 1988 of a composition therefrom forms a conical profile 1986 (e.g., an arrowhead-like profile, a pedal like conical profile, etc.). In aspects, the profile 1986 may take on a lobe like structure (such as pedals on a flower when looking axially down the axis of the delivery tip 1984), etc. The ports 1982 may be distributed over the delivery tip 1984 such that the density of the ports 1982 is varied along the length thereof. In aspects, the ports 1982 may be arranged such a high density of ports are situated towards one end of the delivery region (the region around which the composition is delivered), while a lower density of ports 1982 are located near to the other end of the delivery region, so as to form the desired conical profile 1986.

In aspects, a delivery system or tool in accordance with the present disclosure may include a plurality of delivery tips each tip configured and arranged so as to contribute to a pattern of a composition in accordance with the present disclosure into a volume of tissue in a body. As such, macro patterns may be formed from a plurality of bolus deliveries, from a plurality of delivery tip deliveries, from delivery tips shaped so as to pass along a pathway through a volume of tissue, combinations thereof, etc.

FIG. 20 shows application of a composition, delivery system, and delivery tools 2000*a,b* each in accordance with the present disclosure to treatment of a carotid body 71 (i.e., a target site near to an access lumen such as a ganglion, a tumor, a sensory body, a node, a lymph node, etc.). The delivery tools 2000*a,b* include one or more needle-like delivery tips 2005*a,b* in accordance with the present disclosure, each delivery tip 2005*a,b* may be tipped with a sensor and/or electrode 2010*a,b* each in accordance with the present disclosure. The delivery tips 2005*a,b* may include a lumen to fluidly couple the distal tip of the delivery tools 2000*a,b* to the proximal end thereof. The lumen may be coupled with one or more ports in accordance with the present disclosure so as to deliver a composition to the carotid body 71 or a site coupled thereto. The delivery tip 2005*a,b* may be advanced 2020*a,b* into the tissues around the carotid bifurcation so as to couple one or more of the sensors and/or electrodes 2010*a,b* with the carotid body 71 or one or more sites thereabout thus forming one or more target tissues, monitoring sites or treatment sites 73*a-d* within or around the carotid body 71. The delivery tools 2000*a,b* may include a jacket to alter the stiffness of one or more segments of the delivery tools 2000*a,b*, to protect the delivery tip 2005*a,b*, one of the sensors 2010*a,b*, etc. In aspects, the delivery tools 2000*a,b* may include one or more stabilizing members, an anchor, a hook, a balloon, or the like, configured so as to stabilize and/or orient one or more regions of delivery tools 2000*a,b* near to the intended treatment site. Once stabilized, the delivery tips 2005*a,b* may be advanced 2020*a,b* towards the carotid body 71 or an associated treatment site 73*a-d*. In aspects, the delivery tools 2000*a,b* or associated delivery tips 2005*a,b* may include one or more radiopaque markers, or may be constructed with one or more radiopaque materials in order to assist a surgeon with visualization of the surgical site during the procedure. In aspects, the stabilizing members may be configured to limit relative motion between the delivery tips 2005*a,b* (e.g., the needles, the electrodes 2010*a,b*, etc.) and the carotid body 71, vessel walls 75, 77, 79, associated treatment/monitoring sites 73*a-d*, etc. during one or more procedures performed thereon.

In aspects, the delivery tools 2000*a,b* may be used to monitor one or more sites 73*a-d* within and around the carotid body 71 to assist in selectively ablating only a region of the carotid body (e.g., an outer layer, a surface, a chemoreceptor, a baroreceptor, etc.). In aspects, the delivery tools 2000*a,b* may be used to both sense and selectively ablate and/or deliver a composition to regions of the carotid body 71 or a site 73*a-d* there about. In such procedures, the sensing may be performed with or without stimulation/stress to determine the ideal locations within the carotid body 71 to perform a neuromodulation, chemical denervation, ablation, delivery of a neural agonist, neural antagonist, etc. Upon determining the ideal locations, an RF current, a microbolus of neurotoxin, etc. may be injected into key sites amongst the monitoring/treatment sites 73*a-d*. Such a procedure may be advantageous for neuromodulating the carotid body 71 while limiting damage to surrounding structures, or to regions of the carotid body 71 that are to be spared in the procedure.

As shown in FIG. 20, the neural body 71 (such as, in this non-limiting example, a carotid body) may be located in the vicinity of a main carotid artery 75, an internal carotid artery 77, or an external carotid artery 79. The delivery tools 2000*a,b* may be configured for placement in a lumen 75, 77, 79 in the vicinity of the neural body 71 (i.e., in this case a carotid body), neurons coupled thereto (in the vicinity of regions 73*a-d*), and/or receptors (i.e., in this case baroreceptors lining wall of the internal carotid artery 77). In aspects, one or more elements of the delivery tools 2000*a,b* may be configured so as to be actuate-ably advanced 2020*a,b* into the wall of the lumen 75, 77, 79, or into contact therewith so as to be advanced towards a target tissue 73*a-d* (e.g., one or more regions of the neural body 71, a region adjacent to the neural body 73*c,d*, nerves and/or nerve plexuses 73*a,b* coupled to the neural body 71, and/or regions including receptors in the vicinity of the neural body 71 and/or the walls of the adjacent lumens 75, 77, 79, etc.

In aspects, one or more of the electrodes 2010*a,b* may be configured to stimulate, and/or treat one or more regions of the carotid body 71, and/or one or more target tissues 73*a-d* as part of a surgical procedure. Additionally, alternatively, or in combination the delivery system may be configured to deliver a stressing agent (e.g., a hormone, a neurotransmitter, nitric oxide, oxygen, carbon dioxide, etc.) directly into the carotid body 71 to assess a change in the neural traffic assessed in the body 71 or within the vicinity of one or more of the target tissues 73*a-d*, assess a change in a body response to the stimulus (e.g., a change in heart rate, respiration, heart rate variability, blood pressure, sPO2, sympathetic outflow, mSNA changes, etc.). The region of treatment as well as the extent of treatment may be monitored and/or controlled by a circuit coupled with one or more electrodes on one or more of the delivery tips 2005a,b.

In aspects, one or more electrodes 2010a,b and/or delivery tips 2005a,b may be configured to monitor, to stimulate, and/or to alter (e.g., deaden or block neural traffic, ablate the nerves, etc.), neurological activity in one or more nerve bundles extending from the neural body 71. Changes in neural traffic after a surgical procedure, in response to a stimulus, or the like may be used to assist in controllably treating one or more regions of target tissue 73c-d in or near the neural body 71, or other target tissues 73a-b in the vicinity thereof.

In aspects, an RF current may be applied through one or more of the electrodes 2010a,b in order to treat the carotid body 71 or a target site 73a-d. The current may be passed between one or more of the electrodes 2010a,b and a remotely located electrode (not explicitly shown) or between two or more of the electrodes 2010a,b. Such a method may be advantageous for selectively controlling the current flow to the regions of the carotid body 71 in need of treatment. In aspects, the remotely located electrode may be a gel electrode placed upon the skin of the body (not explicitly shown), a needle electrode, an electrode placed within a nearby vein, or the like.

In aspects, a composition in accordance with the present disclosure may be injected into the carotid body 71. The composition may be formulated such that the ablation zone around the carotid body 71 is less than 5 mm outside the margin of the carotid body, less than 3 mm, less than 2 mm, less than 1 mm. Such adjustments may be made by altering the percentage of one or more excipients in the composition, adding a diluting agent (e.g., saline, water, etc.) to the composition, etc. In general, the composition may include a contrast agent in accordance with the present disclosure so as to visualize the migration of the composition after injection into the carotid body 71, or one or more treatment sites 73a-d coupled thereto.

In aspects, a method for treating such tissues may include injecting a first bolus of a first composition into or near to the carotid body 71, the first composition having an ablation and/or migration characteristic to treat at least a portion of the carotid body 71. The method including injecting one or more additional boluses of a second composition, the second composition having an ablation and/or migration characteristic suitable for treating another region of the carotid body 71, migrating outwards from the carotid body 71, etc.

In aspects, a method for treating a carotid body 71 may include accessing the arteriole vasculature of the carotid body and injecting a composition in accordance with the present disclosure into the vasculature, so as to fill the carotid body 71 with the composition. After injection, the composition will temporarily occlude blood flow within the carotid body 71 while the ablative component thereof diffuses into the tissues of the organ and completes ablation thereof (e.g., so as to ablate all receptors in the organ, to ablate particular receptor types in the organ, to ablate chemical receptors, to ablate baroreceptors, etc.). Such a method may be advantageous to safely treat the carotid body with minimal collateral damage to surrounding tissues. As the composition may quickly breakdown in the general blood flow, the risks to the subject are minimized, with ablation being very controllably delivered only to the tissues in the carotid body 71 that are intimately served by the vasculature thereof. The delivery tools 2000a,b may be coupled with one or more controllers 2015a,b respectively to manage needle deployment/retraction 2020a,b, coupling of the delivery tips 2005a,b or one or more sensors 2010a,b with external electronics, a polygraph, or the like.

FIGS. 21a-b show aspects of a delivery system in accordance with the present disclosure for treating tissues along a vessel. FIG. 21a shows aspects of a delivery tool 2100 for use in a delivery system in accordance with the present disclosure. The delivery tool 2100 includes a jacket 2105 including a plurality of ports 2110 through which a plurality of delivery tips 2115a,b in accordance with the present disclosure may pass through in order to couple with a local anatomical site of interest, to stabilize the delivery tip, etc. The delivery tips 2115a,b may include one or more electrodes 2120 and/or sensors at the tip thereof in order to interface with the local anatomical site of interest (e.g., to measure local electrophysiological activity, to determine placement of the tip, to determine if the tip has exited the lumen, etc.). In aspects, the delivery tips 2115a,b may include an insulating layer 2125 configured so as to isolated one or more aspects of the delivery tip 2115b from the surroundings. In aspects, the insulating layer 2125 may include a varying thickness, optionally arranged so as to form one or more step transitions along the length of the delivery tip 2115b. Such steps may be advantageous for limiting the depth of penetration of the delivery tip 2115b into the local tissues.

In aspects, the delivery tips 2115a,b may include a lumen through which to deliver 2130 a composition 2135, a chemical substance, a medicament, etc. to the site of interest. The delivery tips 2115a,b may include one or more ports, shaped elements, etc. in accordance with the present disclosure to treat a region of tissues, interact with an adjacent volume of tissue in a particular pattern, etc. In aspects, the delivery tips 2115a,b may be deployed 2140 from the delivery tool 2100 so as to interact with an adjacent volume of tissue.

In aspects, the delivery tips 2115a,b and/or anchors may be slidingly coupled with the jacket 2105 such that they may be advanced 2140 as part of a deployment procedure. In aspects, the delivery tips 2115a,b and/or stabilizing elements may be coupled with a connector, actuator, and/or a controller 2145 generally situated at the proximal end of the delivery tool 2100.

FIG. 21b illustrates aspects of a delivery tool 2150 in accordance with the present disclosure placed within a lumen 74. The delivery tool 2150 may include one or more zones 2155a,b in accordance with the present disclosure. The delivery tool 2150 includes a first sensing zone 2155a located along the length thereof for interfacing with the lumen 74 wall proximally to a treatment site. The delivery tool 2150 includes a second sensing zone 2155b located at the distal tip thereof for interfacing with the lumen 74 distally to a treatment site. The delivery tool 2150 includes one or more microneedle delivery tips 2160, which may be advanced from the body of the delivery tool 2150 and into the wall of the lumen 74 into which it has been placed as part of a procedure. Such needle advancement or retraction 2165 may be coordinated by an operator, a controller 2170, etc. In aspects, the microneedle delivery tips 2160 may provide a means for delivering a composition, a chemical agent 2175 into the tissues surrounding the lumen 74. In aspects, the microneedle delivery tips 2160 may include one or more electrodes 2180 to monitor and/or interface (e.g., stimulate, ablate, etc.) with the local tissues upon deployment therein, to monitor (e.g., via impedance changes, via changes in local electrophysiological signals, etc.) a margin of migration or treatment of a bolus delivered to the tissues. In aspects, the delivery tool 2150 may be configured so as to deliver the microneedle tips 2160 into the adventitia of the lumen 74, or optionally directly into the parenchyma of an organ to be treated. Such a configuration may be advantageous to provide a composition in accordance with the present disclosure, a neurotoxin, a cancer treating agent, a neuroblocking agent, a neurostimulating agent, etc. into the target tissues as part of a treatment procedure in accordance with the present disclosure.

FIGS. 22a-n show aspects of a delivery system and method for treating tissues in a thin walled structure. FIG. 22a shows a thin walled section 81 (e.g., a wall of an atrium, a bowel wall, a bladder wall, an esophagus wall, a membrane, a vaginal wall, a pericardial sac, etc.) and an adjacent structure 82 that is not to be treated (e.g., an esophagus beside an atrial wall, a prostate next to a bladder, a gall bladder next to a duodenum, etc.). The desired treatment zone 2201 is shown substantially within the thin walled section 81.

Figure 22B:
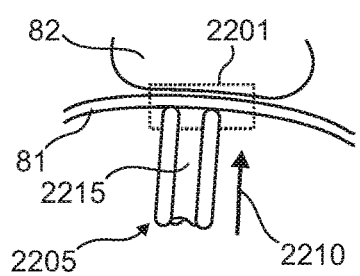

FIG. 22b illustrates aspects of a delivery tool 2205 in accordance with the present disclosure, the delivery tool 2205 biased 2210 against the thin walled section 81 so as to seal a lumen 2215 against the wall and the tip of the delivery tool 2205.

Figure 22C:
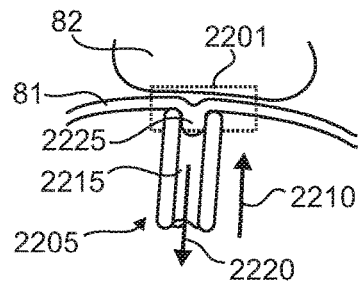

FIG. 22c illustrates application of a vacuum, or suction 2220 to the lumen 2215 of the delivery tool 2205 to draw a section of tissue 2225 into the lumen 2215. Such an approach may be advantageous to confidently capture and retain the tissue segment for subsequent treatment thereof. In aspects, the tip of the delivery tool 2205 may include a plurality of electrodes (not explicitly shown), for passing an RF current through the section of tissue 2225, so as to safely treat it without affecting the adjacent structure 82.

Figure 22D:
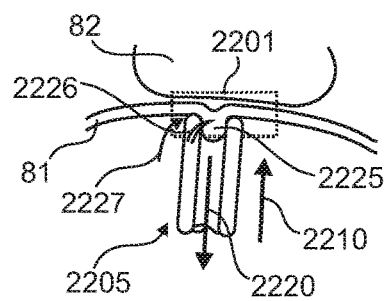

FIG. 22d illustrates the delivery tool 2205, having drawn a section of tissue 2225 into the lumen 2215 thereof, the delivery tool 2205 driving, engaging, or otherwise penetrating 2227 a microneedle delivery tip 2226 in accordance with the present disclosure into the section of tissue 2225, so as to engage therewith.

Figure 22E:
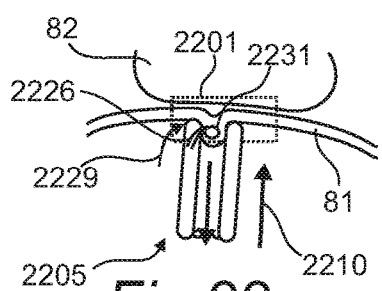

FIG. 22e illustrates delivery 2229 of a bolus 2231 of a composition in accordance with the present disclosure into the section of tissue 2225, the composition retained within the section of tissue 2225 for treatment thereof.

In aspects, the tip of the delivery tool 2205 may include one or more electrodes in accordance with the present disclosure to assess the electrophysiological properties of the tissues, to assess the effect of the bolus on the tissues, etc.

Figure 22F:
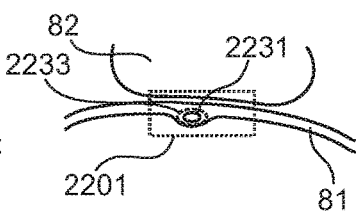

FIG. 22f illustrates the thin walled section 81 after removal of the delivery tool 2205, the bolus 2231 embedded therein, one or more active components of the bolus 2231 diffusing into the tissues to form a treatment zone 2233. The adjacent structure 82 is substantially untreated, unpenetrated, etc. Such an approach may be advantageous for precisely treating thin walls without penetrating them, without affecting adjacent structures 82, etc.

Figure 22G:
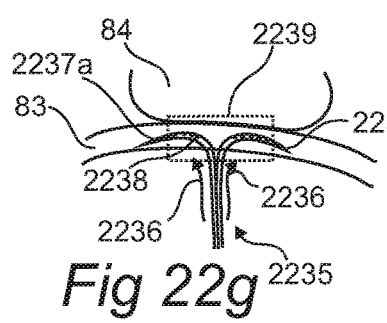

FIG. 22g shows a delivery tool 2235 in accordance with the present disclosure including two delivery tips 2237a,b having been advanced 2236 into a thin walled section 83 without penetrating there through or into an adjacent structure 84. The delivery tips 2237a,b include a plurality of ports 2238 for delivery of a composition there through into the thin walled section 83. The desired treatment zone 2239 is shown substantially within the thin walled section 83.

Figure 22H:
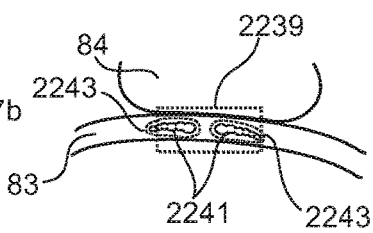

FIG. 22h shows a plurality of boluses 2241 after injection by the delivery tool 2235 of FIG. 22g after the tool has been retracted from the thin walled section 83. One or more active elements of the composition have diffused into the adjacent tissues to form a local treatment zone 2243 within the thin walled section 83 but without substantially affecting the adjacent structure 84. In aspects, the local treatment zone 2243 is the region into which the initial boluses 2241 will migrate after injection into the local tissues. The extent of the local treatment zone 2243 is determined by the properties of the composition delivered, the local tissue properties, and the like.

Figure 22I:
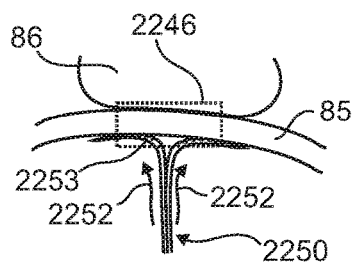

FIG. 22i illustrates a delivery tool 2250 biased 2252 against a thin walled section 85, the delivery tool 2250 including a plurality of ports 2253 arranged thereupon such that the ports 2253 are in intimate contact with the thin walled section 85 upon biasing 2252 the device there against. The thin walled section 85 is near to an adjacent structure 86 for which treatment is not desired (treatment may generally be desired in the treatment zone 2246).

Figure 22J:
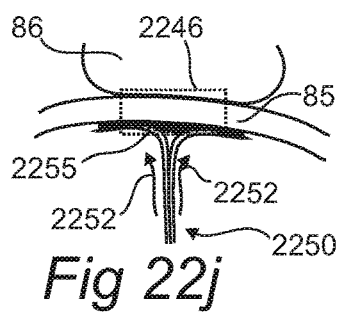
Figure 22L:
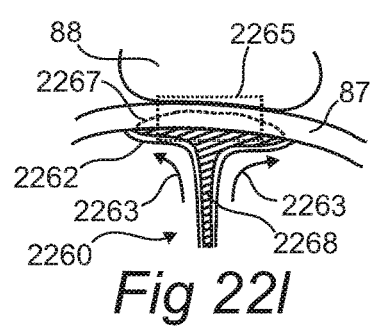
Figure 22M:
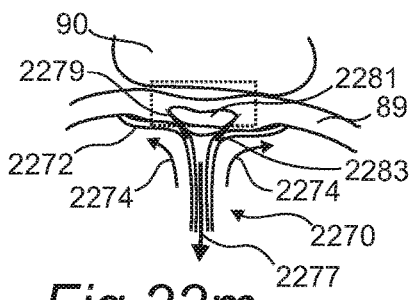

FIG. 22j shows the delivery tool 2250 after delivery of a bolus 2255 of a composition in accordance with the present disclosure to the interface between the ports 2253 and the thin walled section 85. The tool 2250 may be held against the tissues for a period of time, such that the composition may treat the tissues, such that one or more components of the composition may diffuse into the tissues, etc.

Figure 22K:
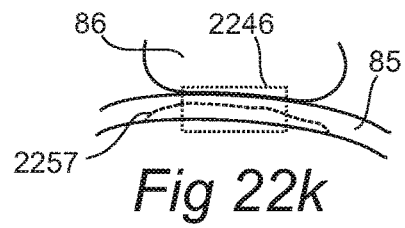
Figure 22N:
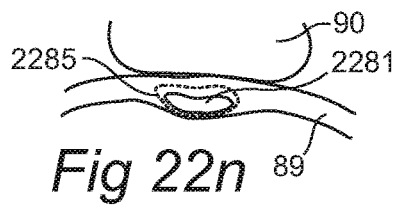

FIG. 22k shows the thin walled section 85 and a treated zone 2257 substantially in the desired treatment zone 2246, having treated the thin walled section 85 without substantially affecting the adjacent structure 86.

FIG. 22l illustrates a delivery tool 2260 with a deployable fixture 2262, the deployable fixture 2262 shaped like an inverted umbrella, a suction cup, etc. the deployable fixture 2262 shown after deployment 2263 within a lumen of a body, the deployable fixture biased against a thin walled section 87. The thin walled section 87 includes a desired treatment zone 2265 substantially residing within the thin walled section 87 and outside of the margins of an adjacent structure 88. The delivery tool 2260 is shown with a bolus 2268 of a composition in accordance with the present disclosure biased against the thin walled structure 87 so as to form a treatment zone 2267 substantially aligned with the desired treatment zone 2265.

FIG. 22m shows a delivery tool 2270 with a deployable fixture 2272 deployed and biased 2274 against a thin walled section 89. The delivery tool 2270 includes a lumen in which a vacuum 2277 has been formed so as to draw a section of the thin walled structure 89 onto one or more delivery tips 2279 in accordance with the present disclosure. After interfacing the delivery tips 2279 with the thin walled structure 89, one or more boluses 2281 of a composition in accordance with the present disclosure may be injected into the section for treatment thereof. In aspects, the delivery tips 2279 or deployable fixture 2272 may include one or more sensors, electrodes, etc. 2283 to record electrophysiological activity, detect contact with the wall, monitor delivery of the boluses 2281 into the thin walled section 89, monitor the resulting treatment process, monitor changes in electrophysiological activity in the adjacent tissues, etc.

FIG. 22n shows the thin walled section 89 and the adjacent structure 90 with the embedded boluses 2281 of composition, the composition forming a treatment zone 2285 substantially within the thin walled section 89.

Some non-limiting examples of agents suitable for performing a stress test (i.e., stressing agents), include a vasodilator, a vasoconstrictor, a neuroblocker, a neurostimulant, a neural antagonist, a neural agonist, an inverse agonist, a diuretic, insulin, glucose, beta-adrenergic receptor antagonist, angiotensin-11 converting enzyme inhibitor, calcium channel blocker, an HMG-CoA reductase inhibitor, digoxin, an anticoagulant, a diuretic, a beta blocker, an ACE inhibitor, a steroid, a combination thereof, or the like.

Sensory fibers tend to run with the SNS but may also run with the PNS (parasympathetic) plexuses although many PNS afferents are used to adjust heart function, and may not likely signal pain directly (i.e. afferent traffic may convey more than simply a local stretch-based pain response).

If sufficient care is not given to limiting medial damage during a procedure, excessive damage to the media of a coronary artery may drive neointimal thickening and stenosis following the procedure. In aspects, ablation modalities such as RF ablation may cause significant trauma to the media during a procedure, and may therefore accelerate restenosis of the vessel after the procedure. The methods provided in accordance with the present disclosure may minimize medial damage and thus provide a means for affecting neural traffic without accelerating restenosis of the vessel.

Generally speaking, the goals of such procedures are: (1) to find suitable target sites, to direct and confirm therapy with sensing devices; (2) to augment neural traffic without damaging the media; and (3) to establish the augmented neural traffic with minimal inflammatory volume.

Embodiments include use of at least one of a composition in accordance with the present disclosure and a delivery system in accordance with the present disclosure to treat a cardiac disease, a cardiac arrhythmia, to isolate a tissue site in a cardiac muscle, to treat a diseased tissue site in an organ, or a combination thereof.

Embodiments also include use of at least one of a composition, a sensing system, or a delivery system each in accordance with the present disclosure to locally identify and/or treat angina, ischemia (acute and chronic), arrhythmias (supraventricular or ventricular), heart failure, heart failure including both systolic and diastolic dysfunction, coronary artery spasm and associated pain, to perform coronary chamber isolation, or a combination thereof.

Embodiments further include use of at least one of a composition, a sensing system, or a delivery system each in accordance with the present disclosure to locally augment heart function, influence cardiac neuro-plastic remodeling, stop neuro-plastic remodeling, breakup one or more inter ganglion connections, or a combination thereof.

Embodiments also include use of at least one of a composition, a sensing system, or a delivery system each in accordance with the present disclosure to locally reduce or eliminate afferent traffic from a region of cardiac tissue, reduce sympathetic innervation to a region of cardiac tissue, alter one or more receptor inputs to a neural network on coupled with cardiac tissue of a subject.

Embodiments further include use of at least one of a composition, a sensing system, and/or delivery system each in accordance with the present disclosure to bridge a denervated region of cardiac tissue, facilitate communicating of a cardiac signal from a first site to a second site in a heart.

Embodiments also include use of at least one of a composition, a sensing system, or a delivery system each in accordance with the present disclosure to map neural traffic over a region of heart muscle, to map the physiologic interconnection between two or more ganglia, locate the source of aberrant neural traffic in a cardiac neural network, and/or treat the heart based upon the map or location.

Embodiments further include use of at least one of a composition, a sensing system, or a delivery system each in accordance with the present disclosure to alter autonomic neural traffic to one or more sites on a heart of a subject or a vascular structure coupled thereto.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A delivery system, comprising:
   a delivery tool comprising an elongate member having a proximal end and a distal end and defining a lumen extending at least partially along a length of the delivery tool;
   one or more deployable elements coupled to the delivery tool and in fluid communication with the lumen, the one or more deployable elements deployable from the delivery tool and configured to at least one of penetrate into or bias against a tissue volume, the one or more deployable elements comprising one or more ports;
   an injector in fluid communication with a reservoir containing a treatment agent, the injector configured to selectively control delivery of the treatment agent to the lumen of the delivery tool for passage through the ports of the one or more deployable elements;
   one or more sensors mounted to at least one of the delivery tool or the one or more deployable elements, the one or more sensing elements configured to sense neural activity within the tissue volume and to generate output signals representative of at least one of physiological data and electrophysiological data of the neural activity within the tissue volume; and
   a controller for receiving the signals from the one or more sensors, the controller configured to control at least one of deployment or operation of the one or more deployable elements based on the output signals generated by the one or more sensors.

2. The delivery system in accordance with claim 1, further comprising a thermal regulating unit in fluid communication with the lumen of the delivery tool, the thermal regulating unit configured to maintain the treatment agent at a predetermined temperature at least one of prior to delivery and during delivery.

3. The delivery system in accordance with claim 2, wherein the thermal regulating unit comprises a heating band mounted to the elongate member and at least partially surrounding the lumen, the heating band configured to maintain the treatment agent at a designated temperature during delivery through the lumen.

4. The delivery system in accordance with claim 1, wherein the one or more ports of the one or more deployable elements are configured and arranged with at least one of a spatially changing density and a spatially changing diameter such that the treatment agent, when delivered from the one or more deployable elements, assumes a desired spatial pattern relative to the tissue volume.

5. The delivery system in accordance with claim 1, wherein the one or more deployable elements comprise one or more needles, the one or more needles configured to penetrate into the tissue volume, the one or more needles comprising the one or more ports.

6. The delivery system in accordance with claim 1, wherein the one or more ports of the one or more deployable elements are arranged such that distribution of the treatment agent from the one or more ports forms a treatment pattern comprising the treatment agent, the treatment pattern substantially in the shape of a cylinder, a sphere, an ellipsoid, a torus, a tear drop, or a cone, when delivered to the tissue volume.

7. The delivery system in accordance with claim 1, further comprising a balloon coupled to the delivery tool, the balloon configured to expand to interface with the tissue volume.

8. The delivery system in accordance with claim 1 wherein the one or more deployable elements comprise one or more energy delivery elements configured to deliver energy to the tissue volume.

9. The delivery system in accordance with claim 1, wherein the one or more sensors are configured to at least one of: monitor and determine regions of abnormal electrophysiological activity; determine a direction of nerve traffic along nerves in or adjacent the tissue volume; determine sympathetic neural activity in or adjacent the tissue volume; determine types of nerves in or adjacent the tissue volume; determine effectiveness of at least one of the delivered energy and the delivered treatment agent; and determine response of nerve traffic to a stress test performed on a subject.

10. The delivery system in accordance with claim 1, further comprising a tissue suction element, coupled to the delivery tool, the suction element configured to draw tissue adjacent the tissue volume against or within the lumen of the delivery tool.

11. The delivery system in accordance with claim 1, wherein the one or more deployable elements comprise one or more needles.

12. The delivery system in accordance with claim 11, wherein at least some of the one or more sensors are integrated into the one or more needles.

13. The delivery system in accordance with claim 11, wherein the one or more needles comprise electrodes.

14. The system in accordance with claim 11, wherein at least a first needle of the one or more needles comprises a needle stop, the needle stop configured to limit entry of the first needle into the tissue volume, a location of the needle stop being adjustable along the first needle.

15. The system in accordance with claim 11, wherein the controller is configured to control deployment and retraction of the one or more deployable elements relative to the delivery tool based on the output signals generated by the one or more sensors.

16. The delivery system in accordance with claim 1, wherein the one or more sensors are arranged to define at least first and second sensor zones, the first zone disposed proximal of the one or more deployable elements and the second zone disposed distal of the one or more deployable elements.

17. The delivery system in accordance with claim 1, wherein the at least one or more sensors are mounted to the delivery tool.

18. The delivery system in accordance with claim 1, wherein the one or more deployable elements comprise electrodes configured to at least one of stimulate or ablate the tissue volume.

19. The delivery system in accordance with claim 1, wherein the one or more deployable elements comprise pedals, the pedals configured to bias against the tissue volume upon deployment from the delivery tool.

20. The delivery system in accordance with claim 19, wherein the pedals comprise the one or more sensors.

21. The system in accordance with claim 1, wherein the injector is configured to adjust a volume of the treatment agent in response to one of detected pressure and flow characteristics of the delivered treatment agent.

22. The system in accordance with claim 1, wherein the one or more sensors are configured to sense a change in neural activity adjacent the tissue volume responsive to the treatment agent.

23. The system in accordance with claim 1, further comprising a source of the treatment agent, the treatment agent comprising at least one of a substance, a composition, a neurotoxin, a cancer treating agent, a neuroblocking agent or a neurostimulating agent.

* * * * *